(12) United States Patent
Higgs et al.

(10) Patent No.: US 9,493,570 B2
(45) Date of Patent: Nov. 15, 2016

(54) FIXED DOSAGE REGIMENS FOR ANTI-TYPE I INTERFERON RECEPTOR (IFNAR) ANTIBODIES

(71) Applicant: MedImmune, LLC, Gaithersburg, MD (US)

(72) Inventors: Brandon Higgs, Gaithersburg, MD (US); Yihong Yao, Gaithersburg, MD (US); Bing Wang, Gaithersburg, MD (US); Lorin Roskos, Gaithersburg, MD (US); Linda Chang, Gaithersburg, MD (US)

(73) Assignee: MedImmune, LLC, Gaithersburg, MD (US)

( * ) Notice: Subject to any disclaimer, the term of this patent is extended or adjusted under 35 U.S.C. 154(b) by 0 days.

(21) Appl. No.: 14/407,156

(22) PCT Filed: Jun. 12, 2013

(86) PCT No.: PCT/US2013/045327
§ 371 (c)(1),
(2) Date: Dec. 11, 2014

(87) PCT Pub. No.: WO2013/188494
PCT Pub. Date: Dec. 19, 2013

(65) Prior Publication Data
US 2015/0158949 A1 Jun. 11, 2015

Related U.S. Application Data

(60) Provisional application No. 61/659,138, filed on Jun. 13, 2012.

(51) Int. Cl.
*C07K 16/28* (2006.01)
*A61K 39/395* (2006.01)
*A61K 38/00* (2006.01)
*C12Q 1/68* (2006.01)
*G06F 19/00* (2011.01)
*G06N 7/00* (2006.01)
*A61K 39/00* (2006.01)

(52) U.S. Cl.
CPC ......... *C07K 16/2866* (2013.01); *C12Q 1/6883* (2013.01); *G06F 19/345* (2013.01); *G06N 7/005* (2013.01); *A61K 38/00* (2013.01); *A61K 39/00* (2013.01); *A61K 2039/505* (2013.01); *A61K 2039/54* (2013.01); *A61K 2039/545* (2013.01); *C07K 2317/21* (2013.01); *C07K 2317/76* (2013.01); *C07K 2317/77* (2013.01); *C07K 2317/90* (2013.01); *C07K 2317/94* (2013.01); *C12Q 2600/106* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 2008/0113011 A1 | 5/2008 | Quay et al. | |
| 2009/0186021 A1* | 7/2009 | Dingivan | A61K 39/39541 424/133.1 |
| 2011/0008365 A1* | 1/2011 | Coyle | C07K 16/2866 424/158.1 |
| 2011/0159513 A1 | 6/2011 | Schoeberl et al. | |
| 2011/0183866 A1 | 7/2011 | Clarke et al. | |
| 2011/0250168 A1 | 10/2011 | Nauwynck et al. | |
| 2011/0287022 A1* | 11/2011 | Yao | C07K 16/249 424/158.1 |

FOREIGN PATENT DOCUMENTS

| | | |
|---|---|---|
| WO | WO 2008070137 A1 | 12/2008 |
| WO | WO 2011028933 A1 | 10/2011 |

OTHER PUBLICATIONS

Goldberg, A., et al., "A Phase 1 Multicenter, Open-Label Study of MEDI-546, a Human Anti-Type 1 Interferon Receptor Monoclonal Antibody, in Adults with Scleroderma," 2012 ACR/ARHP Annual Meeting, Abstract No. 692 (2012).

Goldberg, A., et al., "Dose-escalation of human anti-interferon-αreceptor monoclonal antibody MEDI-546 in subjects with systemic sclerosis: a phase 1, multicenter, open label study," Arthritis Research & Therapy, 16(1): R57 (2014).

Higgs, B.W., et al., "Patients with systemic lupus erythematosus, myositis, rheumatoid arthritis and scleroderma share activation of a common type I interferon pathway," Annals of the Rheumatic Diseases, 70: 2029-2036 (2011).

Merrill, J., et al., "Safety public and clinical activity of sifalimumab, a fully human anti-interferon α monoclonal antibody, in systemic lupus erythematosus: a phase 1, multicentre, double-blind randomised study," Annals of the Rheumatic Diseases, 70(11): 1905-1913 (2011).

Wang, B., et al., "Pharmacogenomics and Translational Simulations to Bridge Indications for an Anti-Interferon-α Receptor Antibody," Clinical Pharmacology & Therapeutics, 93(6): 483-492 (2013).

Supplementary European Search Report completed on Dec. 5, 2015, in corresponding European Patent Application No. EP13803921.

\* cited by examiner

*Primary Examiner* — Christine J Saoud
*Assistant Examiner* — Jegatheesan Seharaseyon

(57) ABSTRACT

The disclosure provides methods for treating a subject having a type I IFN-mediated disease or disorder comprising administration of a fixed does of an anti-interferon alpha receptor antibody. The disclosure also provides methods for suppressing a type I interferon (IFN) gene signature (GS) in a subject. In addition, the disclosure provides methods of prognosing or monitoring disease progression in a subject having a type I IFN-mediated disease or disorder, methods of predicting a dosage regimen, methods of identifying a candidate therapeutic agent, methods of identifying a patient as a candidate for a therapeutic agent, and methods of designating a personalized therapy.

1 Claim, 22 Drawing Sheets

(t=0 min)

(t=40 min)

Figure 1:
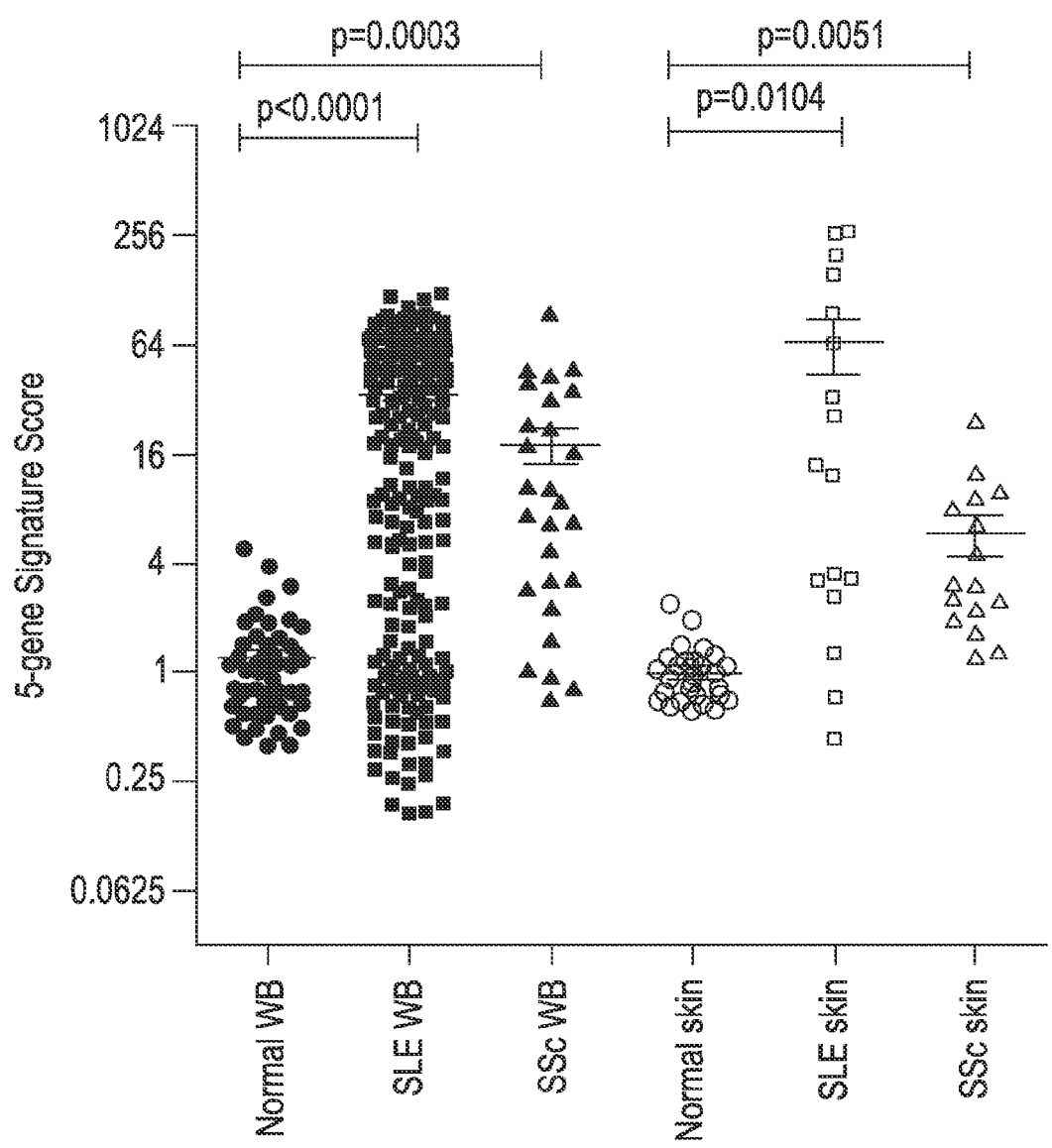

FIG. 5A
PK  SD 1.0 mg/kg SID 9
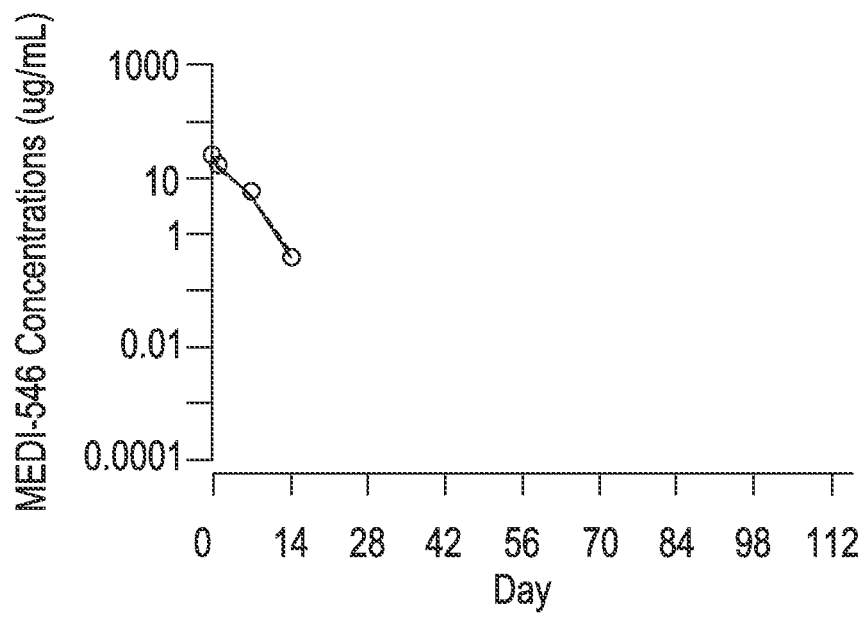
SD 10.0 mg/kg SID 14
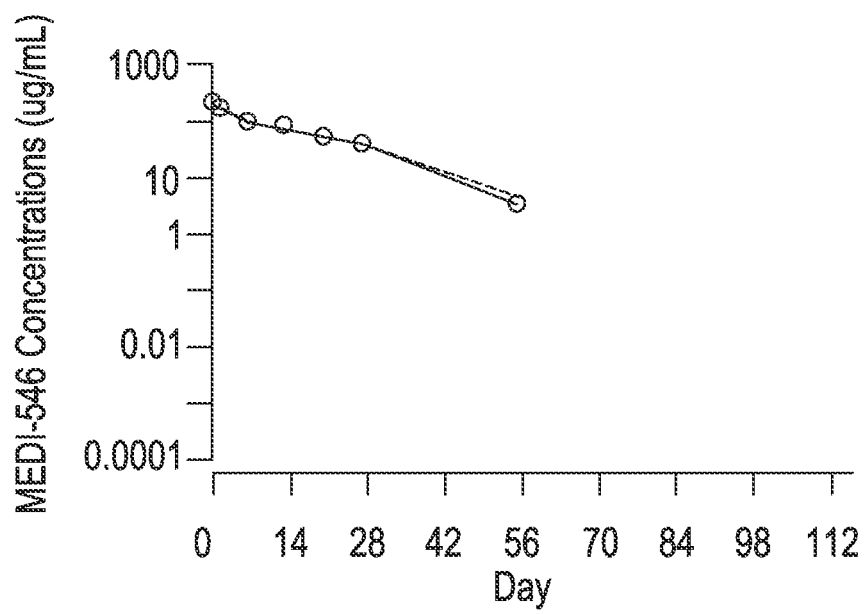

FIG. 5B
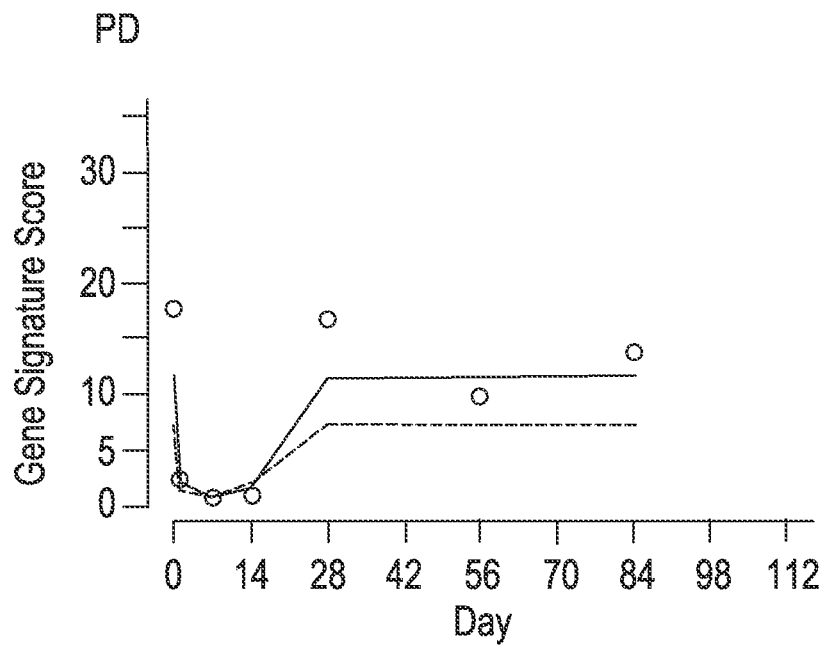
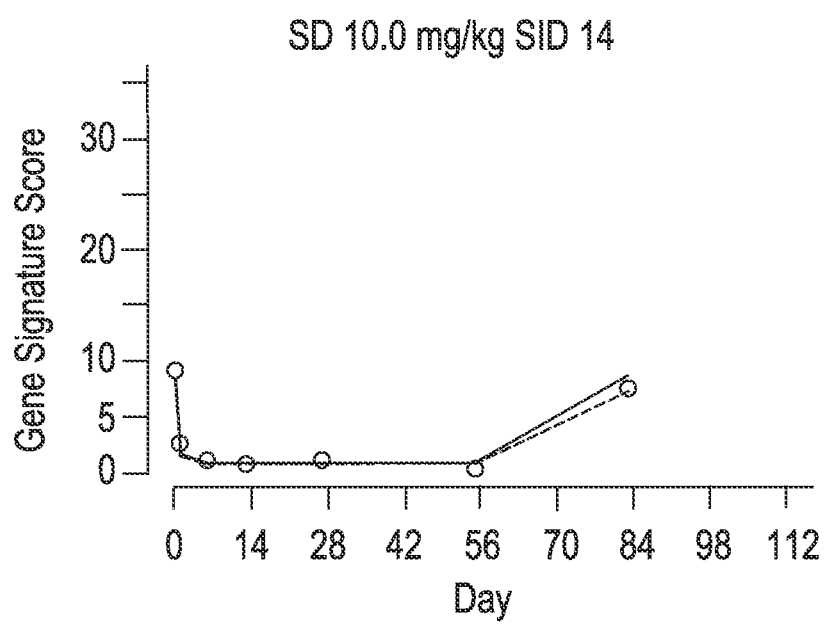

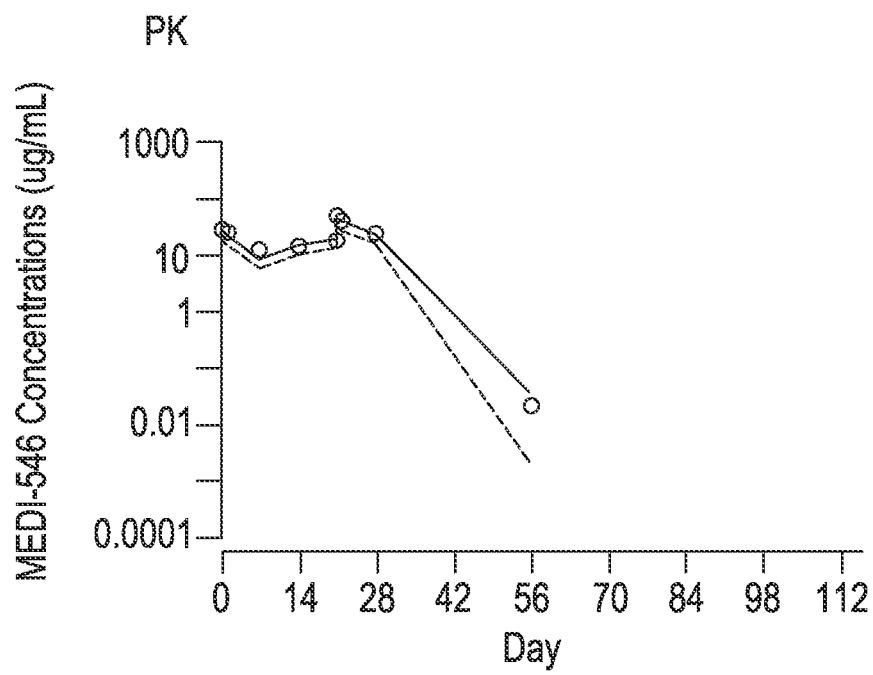
FIG. 5C
MD 1.0 mg/kg SID 24
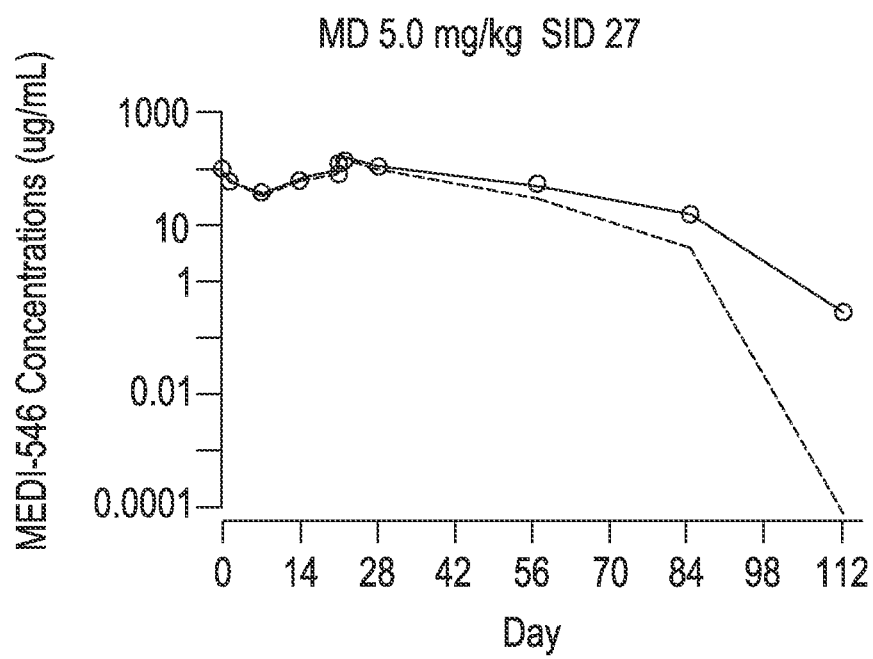
MD 5.0 mg/kg SID 27

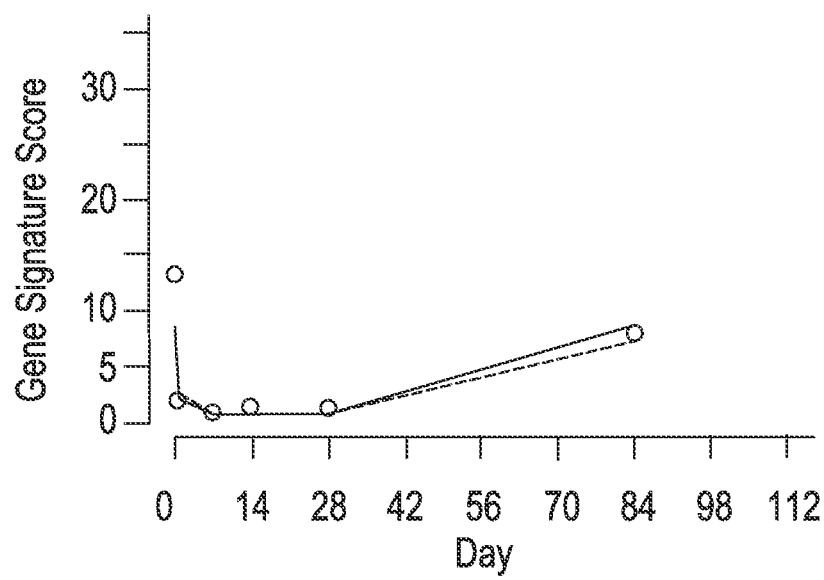
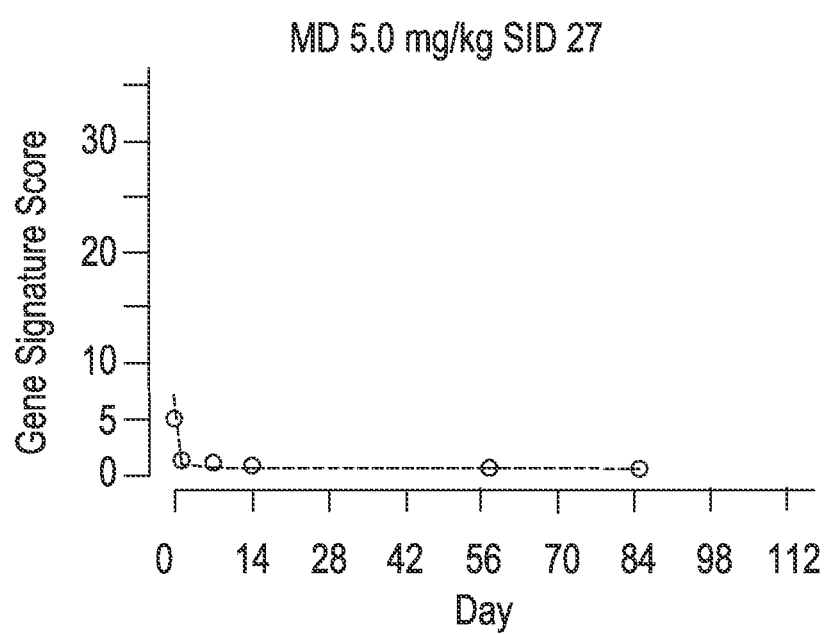
FIG. 5D

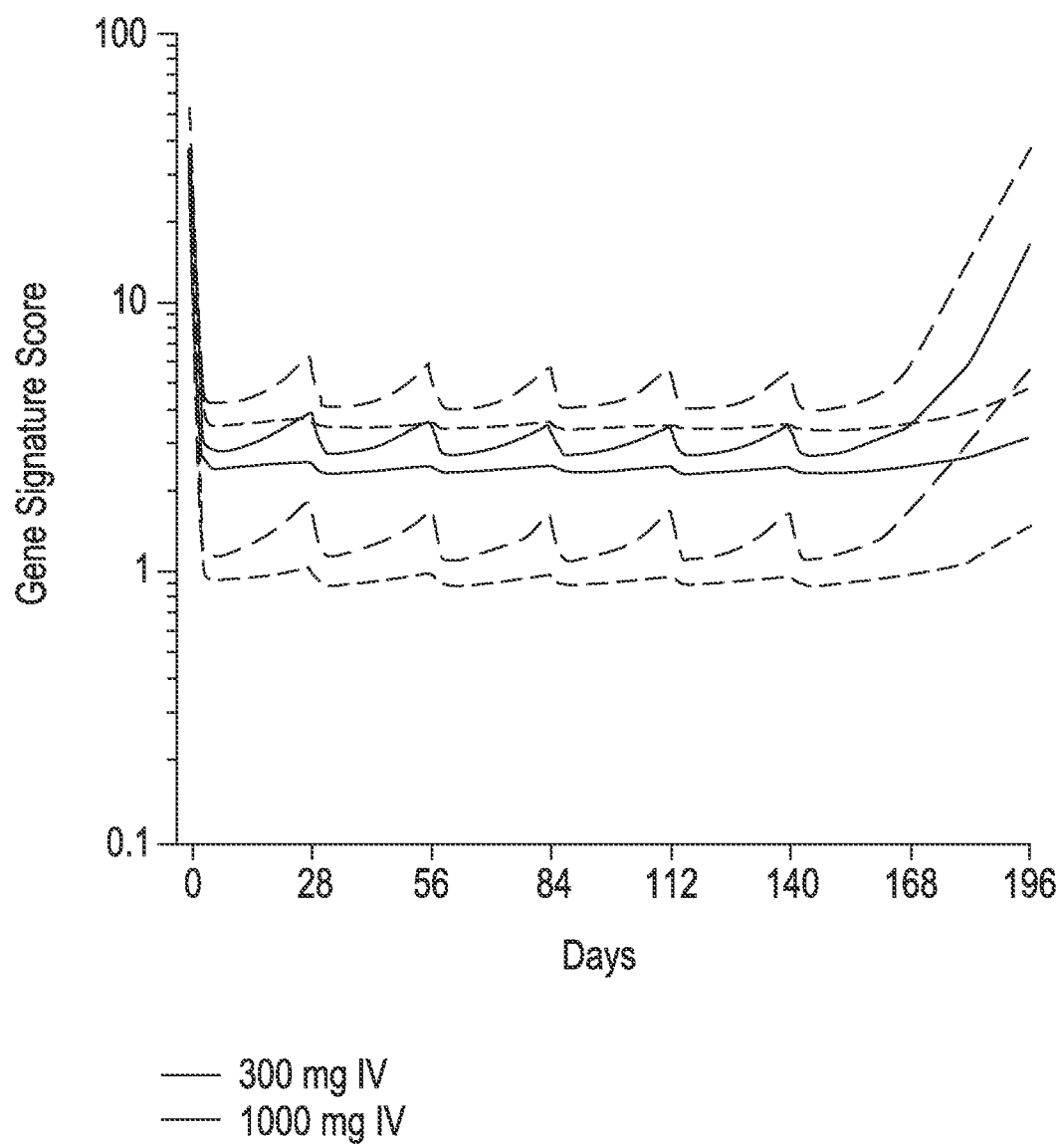

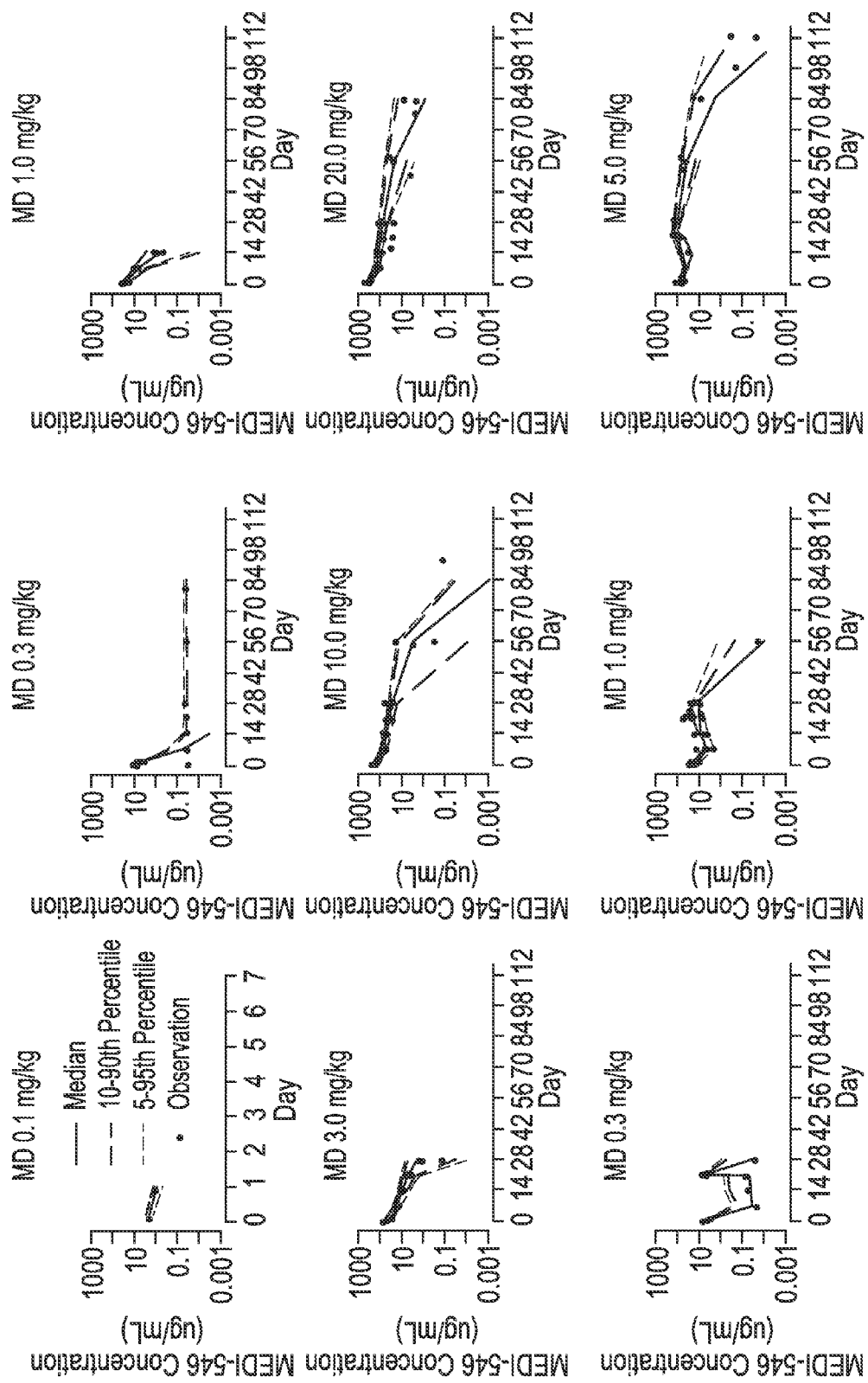

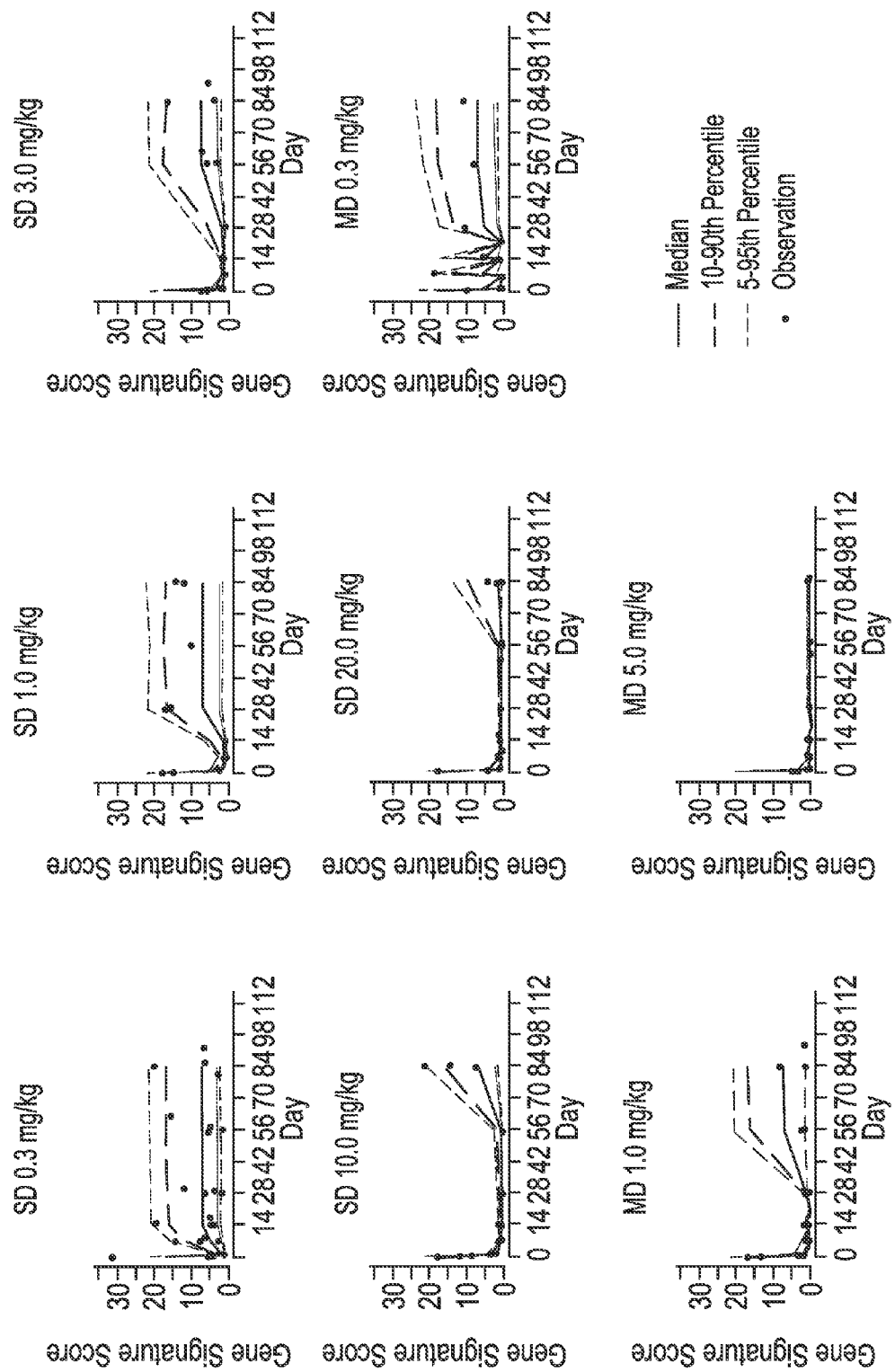

Baseline

Postdose (Day 7 or Day 28)

FIXED DOSAGE REGIMENS FOR ANTI-TYPE I INTERFERON RECEPTOR (IFNAR) ANTIBODIES

CROSS-REFERENCE TO RELATED APPLICATIONS

This application is a U.S. National Stage application of International Application No. PCT/US2013/045327, filed on Jun. 12, 2013, said International Application No. PCT/US2013/045327 claims benefit under 35 U.S.C. §119(e) of the U.S. Provisional Application No. 61/659,138, filed on Jun. 13, 2012. Each of the above listed applications is incorporated by reference herein in its entirety for all purposes.

REFERENCE TO THE SEQUENCE LISTING

This application incorporates by reference a Sequence Listing submitted with this application as text file entitled IFNAR-310US1_Sequence, created on Nov. 24, 2014, and having a size of 88 kilobytes.

BACKGROUND OF THE DISCLOSURE

1. Field of the Disclosure

The present disclosure provides methods for the treatment of autoimmune diseases such as systemic lupus erythematosus, scleroderma, lupus nephritis, and myositis with fixed doses of anti-interferon receptor antibodies.

2. Background Art

Type I interferons (IFNs) are a family of cytokines including 14 IFN-α subtypes, IFN-β, -ω, and -κ, all of which are involved in antiviral or antitumor function. A potential role for type I IFNs in the disease pathogenesis of several autoimmune disorders including systemic sclerosis (SSc, scleroderma), systemic lupus erythematous (SLE), primary Sjögren's, rheumatoid arthritis, as well as myositis.

SLE is a chronic rheumatic disease characterized by autoreactive antibodies targeting a variety of self-antigens resulting in inflammation, tissue and organ damage. The role of type I IFNs has been implicated in the development of SLE. SSc is a rheumatic disease of the connective tissue, affecting multiple systems including skin, muscle, and internal organs. Like SLE, increased type I IFN activity plays a role in the pathogenesis of SSc, as confirmed by the overexpression of type I IFN-inducible genes and the enrichment of plasmacytoid dendritic cells in skin and/or blood of SSc patients (Fleming et al., PLoS One 3:e1452 (2008); Coelho et al., Arch. Dermatol. Res. 299:259-262 (2007); Tan et al., Rheumatology (Oxford) 45:694-702 (2006); Duan et al., Arthritis Rheum. 58:1465-1474 (2008)). These observations along with other data including animal model studies have suggested type I IFN signaling as a viable therapeutic target in both SLE and SSc (Tan et al., Rheumatology (Oxford) 45:694-702 (2006); 28. Crow, Rheum. Dis. Clin. North Am. 36:173-186 (2010); York et al., Arthritis Rheum. 56:1010-1020 (2007)).

Type I IFNs in serum or plasma are not easily measured. On the other hand, type I IFN inducible genes can be conveniently measured improved sensitivity and specificity (Bengtsson et al., Lupus 9:664-671 (2000); Dall'era et al., Ann. Rheum. Dis. 64:1692-1697 (2005); Kirou et al., Arthritis Rheum. 50:3958-3967 (2004)). Several well defined type I IFN signatures have been used to correlate type I IFN activity with SLE or SSc disease pathogenesis (Eloranta et al., Ann. Rheum. Dis. 69:1396-1402 (2010)), disease activity (Bilgic et al., Arthritis Rheum. 60:3436-3446 (2009)), as well as assessing the drug-target interaction (i.e., pharmacodynamics, PD) of an anti-IFN-α therapy in SLE (Yao et al., Arthritis Rheum. 60:1785-1796 (2009); Yao et al., Hum. Genomics Proteomics 2009:374312 (2009); Yao et al., Arthritis Res. Ther. 12 (Suppl 1):S6 (2010)). The development of a type I IFN signature to identify subpopulations showing both activation and concordance of the type I IFN pathway between the peripheral blood and disease-affected tissues in both SLE and SSc (Higgs et al., Ann. Rheum. Dis. 70:2029-2036 (2011)) has demonstrated the potential utility of using a type I IFN signature as a PD marker in both diseases.

The clinical development of a new drug is a lengthy and costly process with low odds of success, and contrary to common impression, the clinical development of biotherapeutics, especially monoclonal antibodies, is not quicker or cheaper than small molecule drugs (DiMasi et al., Clin. Pharmacol. Ther. 87:272-277 (2010)). The early clinical development of biotherapeutics, in particular Phase 1 is much lengthier than for small molecules. Absent definitive efficacy signal from early phase studies in patients, a sensitive, disease-relevant and robust biomarker can greatly aid the interpretation of clinical results.

Type I IFN-mediated diseases such as SLE present diverse disease manifestations and highly variable disease progression, flares and remissions. Due to this heterogeneity, it is crucial to identify patients with similar pathway activation parameters to designate the most appropriate therapies for the different patient subsets. To expedite the clinical development and improve the odds of success, a relevant, sensitive and robust set of PD markers that can be easily tracked or monitored in patients is of great value for dose finding at the early clinical development stage. Methods of applying this set of PD markers would be highly valuable tools to account for differences in target expression and pathway activation in different diseases, and to facilitate bridging between clinical trials in different indications.

BRIEF SUMMARY OF THE DISCLOSURE

The present disclosure provides method for treating a subject having a type I IFN-mediated disease or disorder comprising administration of a fixed dose of an anti-interferon alpha receptor antibody. The disclosure also provides methods for suppressing a type I interferon (IFN) gene signature (GS) in a subject. In addition, the disclosure provides methods of prognosing and monitoring disease progression in a subject having a type I IFN-mediated disease or disorder, methods of predicting a dosage regimen, methods of identifying a candidate therapeutic agent, methods of identifying a patient as a candidate for a therapeutic agent, and methods of designing a personalized therapy. Also disclosed are dosage regimens and personalized therapies selected according to these methods.

In some aspects, the present disclosure provides a method of treating a patient having a type I IFN-mediated disease or disorder comprising (a) measuring a type I Interferon Gene Signature (type I IFN GS) score in a sample taken from a patient having a type I IFN-mediated disease or disorder, relative to a baseline type I IFN GS score; and (b) administering to the patient a fixed dose of an antibody or antigen-binding fragment thereof that modulates type I IFN activity if the patient's type I IFN GS score is elevated; wherein the fixed dose of the antibody or fragment thereof effectively treats the disease or disorder.

In other aspects, the present disclosure provides a method of treating a patient having a type I IFN-mediated disease or disorder comprising (a) administering to a patient having a type I IFN-mediated disease or disorder a fixed dose of an antibody or antigen-binding fragment thereof that modulates type I IFN activity; (b) measuring the patient's type I IFN GS score relative to a baseline type I IFN GS score; and (c) increasing the amount or frequency of subsequent fixed doses if the patient's type I IFN GS score is elevated; wherein suppression of the type I IFN GS of the patient is indicative of treatment efficacy.

In certain aspects, the present disclosure provides a method of treating a patient having a type I IFN-mediated disease or disorder comprising (a) submitting a sample taken from a patient with a type I IFN-mediated disease or disorder for measurement of a type I IFN GS score; (b) determining from the results of the measurement whether the patient's type I IFN GS score is elevated relative to a baseline type I IFN GS score; and, (c) administering to the patient a fixed dose of an antibody or antigen-binding fragment thereof that modulates type I IFN activity if the patient's type I IFN GS score is elevated; wherein the fixed dose of the antibody or fragment thereof effectively treats the disease or disorder.

In some aspects, the present disclosure provides a method of treating a patient having a type I IFN-mediated disease or disorder comprising (a) administering to a patient having a type I IFN-mediated disease or disorder a fixed dose of an antibody or antigen-binding fragment thereof that modulates type I IFN activity; (b) submitting a sample taken from the patient for measurement of a type I IFN GS score; (c) determining from the results of the measurement whether the patient's type I IFN GS score is elevated relative to a baseline type I IFN GS score; and, (d) increasing the amount or frequency of subsequent fixed doses if the patient's type I IFN GS score is elevated; wherein suppression of the type I IFN GS of the patient is indicative of treatment efficacy.

In other aspects, the present disclosure provides a method of treating a patient having a type I IFN-mediated disease or disorder comprising (a) submitting a sample taken from a patient with a type I IFN-mediated disease or disorder for measurement of a type I IFN GS score and comparison to a baseline type I IFN GS score; and (b) administering to the patient a fixed dose of an antibody or antigen-binding fragment thereof that modulates type I IFN activity if the patient's type I IFN GS score is elevated; wherein the fixed dose of the antibody or fragment thereof effectively treats the disease or disorder.

In certain aspects, the present disclosure provides a method of treating a patient having a type I IFN-mediated disease or disorder comprising (a) administering to a patient having a type I IFN-mediated disease or disorder a fixed dose of an antibody or antigen-binding fragment thereof that modulates type I IFN activity; (b) submitting a sample taken from the patient for measurement of a type I IFN GS score and comparison to a baseline type I IFN GS score; and (c) increasing the amount or frequency of subsequent fixed doses if the patient's type I IFN GS score is elevated; wherein suppression of the type I IFN GS of the patient is indicative of treatment efficacy.

In some aspects, the present disclosure provides a method of treating a patient having a type I IFN-mediated disease or disorder comprising (a) measuring a type I IFN GS score from a sample taken from a patient having a type I IFN-mediated disease or disorder; (b) determining whether the patient's type I IFN GS score is elevated relative to a baseline type I IFN GS score; (c) instructing a healthcare provider to administer a fixed dose of an antibody or antigen-binding fragment thereof that modulates type I IFN activity if the patient's type I IFN GS score is elevated; wherein the fixed dose of the antibody or fragment thereof effectively treats the disease or disorder.

In other aspects, the present disclosure provides a method of treating a patient having a type I IFN-mediated disease or disorder comprising (a) obtaining a sample from a patient having a type I IFN-mediated disease or disorder, where the patent has received a fixed dose of an antibody or antigen-binding fragment thereof that modulates type I IFN activity; (b) measuring a type I IFN GS score from the sample; (c) determining whether the patient's type I IFN GS score is elevated relative to a baseline type I IFN GS score; (d) instructing a healthcare provider to increase the amount or frequency of subsequent fixed doses if the patient's type I IFN GS score is elevated; wherein suppression of the type I IFN GS of the patient is indicative of treatment efficacy.

In certain aspects, the present disclosure provides a method of suppressing an type I IFN GS in a patient comprising (a) measuring the type I IFN GS score in a sample taken from a patient having a type I IFN-mediated disease or disorder, relative to a baseline type I IFN GS score; and (b) administering to the patient a fixed dose of an antibody or antigen-binding fragment thereof that modulates type I IFN activity if the patient's type I IFN GS score is elevated; wherein the administration of the antibody or antigen-binding fragment thereof suppresses the type I IFN GS of the patient.

In some aspects, the present disclosure provides a method of suppressing a type I IFN GS in a patient comprising (a) administering to a patient having a type I IFN-mediated disease or disorder a fixed dose of an antibody or antigen-binding fragment thereof that modulates type I IFN activity; (b) measuring the patient's type I IFN GS score relative to a baseline type I IFN GS score; and (c) increasing the amount or frequency of subsequent fixed doses if the patient's type I IFN GS score is elevated; wherein the administration of the antibody or antigen-binding fragment thereof suppresses the type I IFN GS of the patient.

In other aspects, the present disclosure provides a method of suppressing a type I IFN GS in a patient comprising (a) submitting a sample taken from a patient with a type I IFN-mediated disease or disorder for measurement of a type I IFN GS score; (b) determining from the results of the measurement whether the patient's type I IFN GS score is elevated relative to a baseline type I IFN GS score; and, (c) administering to the patient a fixed dose of an antibody or antigen-binding fragment thereof that modulates type I IFN activity if the patient's type I IFN GS score is elevated; wherein the administration of the antibody or antigen-binding fragment thereof suppresses the type I IFN GS of the patient.

In certain aspects, the present disclosure provides a method of suppressing a type I IFN GS in a patient comprising (a) administering to a patient having a type I IFN-mediated disease or disorder a fixed dose of an antibody or antigen-binding fragment thereof that modulates type I IFN activity; (b) submitting a sample taken from the patient for measurement of a type I IFN GS score; (c) determining from the results of the measurement whether the patient's type I IFN GS score is elevated relative to a baseline type I IFN GS score; and, (d) increasing the amount or frequency of subsequent fixed doses if the patient's type I IFN GS score is elevated; wherein the administration of the antibody or antigen-binding fragment thereof suppresses the type I IFN GS of the patient.

In some aspects, the present disclosure provides a method of suppressing a type I IFN GS in a patient comprising (a) submitting a sample taken from a patient with a type I IFN-mediated disease or disorder for measurement of a type I IFN GS score and comparison to a baseline type I IFN GS score; and (b) administering to the patient a fixed dose of an antibody or antigen-binding fragment thereof that modulates type I IFN activity if the patient's type I IFN GS score is elevated; wherein the administration of the antibody or antigen-binding fragment thereof suppresses the type I IFN GS of the patient.

In other aspects, the present disclosure provides a method of suppressing a type I IFN GS in a patient comprising (a) administering to a patient having a type I IFN-mediated disease or disorder a fixed dose of an antibody or antigen-binding fragment thereof that modulates type I IFN activity; (b) submitting a sample taken from the patient for measurement of a type I IFN GS score and comparison to a baseline type I IFN GS score; and (c) increasing the amount or frequency of subsequent fixed doses if the patient's type I IFN GS score is elevated; wherein the administration of the antibody or antigen-binding fragment thereof suppresses the type I IFN GS of the patient.

In certain aspects, the present disclosure provides a method of suppressing a type I IFN GS in a patient comprising (a) measuring a type I IFN GS score from a sample taken from a patient having a type I IFN-mediated disease or disorder; (b) determining whether the patient's type I IFN GS score is elevated relative to a baseline type I IFN GS score; (c) instructing a healthcare provider to administer a fixed dose of an antibody or antigen-binding fragment thereof that modulates type I IFN activity if the patient's type I IFN GS score is elevated; wherein the administration of the antibody or antigen-binding fragment thereof suppresses the type I IFN GS of the patient.

In some aspects, the present disclosure provides a method of suppressing a type I IFN GS in a patient comprising (a) obtaining a sample from a patient having a type I IFN-mediated disease or disorder, where the patent has received a fixed dose of an antibody or antigen-binding fragment thereof that modulates type I IFN activity; (b) measuring a type I IFN GS score from the sample; (c) determining whether the patient's type I IFN GS score is elevated relative to a baseline type I IFN GS score; (d) instructing a healthcare provider to increase the amount or frequency of subsequent fixed doses if the patient's type I IFN GS score is elevated; wherein the administration of the antibody or antigen-binding fragment thereof suppresses the type I IFN GS of the patient.

In other aspects, the present disclosure provides a method of monitoring therapeutic efficacy of a fixed dose of an antibody or antigen-binding fragment thereof that modulates type I IFN activity in a patient having a type I IFN-mediated disease or disorder comprising (a) measuring a first type I IFN GS score in a sample taken from a patient having a type I IFN-mediated disease or disorder; (b) administering to the patient a fixed dose of an antibody or antigen-binding fragment thereof that modulates type I IFN activity; (c) measuring a second type I IFN GS score in a sample taken from the patient following antibody administration; and (d) comparing the second type I IFN GS score to the first type I IFN GS score; wherein a decrease between the first and second type I IFN GS scores indicates efficacy or good prognosis.

In certain aspects, the present disclosure provides a method of monitoring therapeutic efficacy of a fixed dose of an antibody or antigen-binding fragment thereof that modulates type I IFN activity in a patient having a type I IFN-mediated disease or disorder comprising (a) submitting a sample taken from a patient with a type I IFN-mediated disease or disorder for measurement of a first type I IFN GS score; (b) administering to the patient a fixed dose of an antibody or antigen-binding fragment thereof that modulates type I IFN activity; (c) submitting a sample taken from a patient with a type I IFN-mediated disease or disorder for measurement of a second type I IFN GS score; and (d) comparing the second type I IFN GS score to the first typ I IFN GS score; wherein a decrease between the first and second type I IFN GS scores indicates efficacy or good prognosis.

In some aspects, the present disclosure provides a method of monitoring therapeutic efficacy of a fixed dose of an antibody or antigen-binding fragment thereof that modulates type I IFN activity in a patient having a type I IFN-mediated disease or disorder comprising (a) measuring a first type I IFN GS score from a sample taken from a patient having a type I IFN-mediated disease or disorder; (b) instructing a healthcare provider to administer a fixed dose of an antibody or antigen-binding fragment thereof that modulates type I IFN activity; (c) measuring a second type I IFN GS score in a sample taken from the patient following antibody administration; and (d) comparing the second type I IFN GS score to the first type I IFN GS score; wherein a decrease between the first and second type I IFN GS scores indicates efficacy or good prognosis.

In other aspects, the method of treating a patient having a type I IFN-mediated disease or disorder, and the method of suppressing a type I IFN GS in a patient further comprise measuring the patient's type I IFN GS score relative to a baseline type I IFN GS score, relative to the patient's earlier IFN GS score, or both, after the administration of the fixed dose. In some aspects, the method of treating a patient having a type I IFN-mediated disease or disorder, and the method of suppressing a type I IFN GS in a patient further comprise measuring the patient's type I IFN GS score relative to a baseline type I IFN GS score, relative to the patient's earlier type I IFN GS score, or both, after the administration of a subsequent fixed dose.

In certain aspects, the method of treating a patient having a type I IFN-mediated disease or disorder, and the method of suppressing a type I IFN GS in a patient further comprise submitting a sample from the patient for measurement of the patient's type I IFN GS score relative to a baseline type I IFN GS score, relative to the patient's earlier type I IFN GS score, or both, after the administration of the fixed dose. In some aspects, the method of treating a patient having a type I IFN-mediated disease or disorder, and the method of suppressing a type I IFN GS in a patient further comprise submitting a sample from the patient for measurement of the patient's type I IFN GS score relative to a baseline type I IFN GS score, relative to the patient's earlier type I IFN GS score, or both, after the administration of a subsequent fixed dose.

In some aspects, the method of treating a patient having a type I IFN-mediated disease or disorder, and the method of suppressing a type I IFN GS in a patient further comprise increasing the amount or frequency of subsequent fixed doses if the patent's type I IFN GS score remains elevated. In other aspects, the method of treating a patient having a type I IFN-mediated disease or disorder, and the method of suppressing a type I IFN GS in a patient further comprise instructing a healthcare provider to increase the amount or frequency of subsequent fixed doses if the patent's type I IFN GS score remains elevated. In yet other aspects, the method of treating a patient having a type I IFN-mediated disease or disorder, and the method of suppressing a type I IFN GS in a patient further comprise increasing the amount or frequency of subsequent fixed doses if the patent's type I IFN GS score remains elevated.

The present disclosure also provides a method of treating a patient having a type I IFN-mediated disease or disorder comprising administering a fixed dose of an antibody or antigen-binding fragment thereof that modulates type I IFN activity, wherein the fixed dose is effective to treat the disorder.

In some aspects, the type I IFN activity is IFN-alpha activity. In some aspects, the type I IFN GS comprises up-regulated expression or activity of at least 4 pharmacodynamic (PD) marker genes selected from the group consisting of IF16, RSAD2, IF144, IF144L, IF127, MX1, IFIT1, HERC5, ISG15, LAMP3, OAS3, OAS1, EPST1, IFIT3, LY6E, OAS2, PLSCR1, SIGLEC1, USP18, RTP4, and DNAPTP6. In other aspects, the type I IFN GS comprises up-regulated expression or activity of genes IF127, IF144, IF144L, and RSAD2. In some aspects, the type I IFN GS further comprises up-regulated expression or activity of gene IF16.

In some aspects, the antibody or antigen-binding fragment thereof that modulates type I IFN activity specifically binds to an IFN receptor. In other aspects, the IFN receptor is an IFN alpha receptor. In some aspects, the IFN alpha receptor is IFNAR1. In other aspects, the antibody or antigen binding fragment thereof specifically binds to subunit 1 of IFNAR1. In some aspects, the antibody or antigen-binding fragment thereof is monoclonal. In other aspects, the antibody or antigen-binding fragment thereof comprises an immunoglobulin IgG Fc region. In specific aspects, the antibody is MEDI-546 or an antigen-binding fragment thereof. In some aspects, the antibody or antigen-binding fragment thereof suppresses the type I IFN GS in disease tissue.

In some aspects, the fixed dose ranges from about 300 mg to about 1000 mg. In other aspects, the fixed dosage is lower than about 300 mg. In other aspects, the fixed dose is about 100 mg. In certain aspects, the fixed dose is selected from the group consisting of about 300 mg, about 400 mg, about 500 mg, about 600 mg, about 700 mg, about 800 mg, about 900 mg and about 1000 mg.

In some aspects, the disease tissue is skin. In some aspects, the antibody or antigen-binding fragment thereof suppresses the type I IFN GS in peripheral blood. In other aspects, the suppression is full suppression. In certain aspects, the suppression is partial suppression.

In some aspects, the antibody or antigen-binding fragment thereof is administered in two or more doses. In some aspects, the therapeutic agent is administered monthly. In some aspects, the therapeutic agent is administered intravenously, intramuscularly, subcutaneously, or a combination thereof. In some aspects, the disease is an autoimmune disease. In some aspects, the autoimmune disease is systemic lupus erythematosus (SLE), scleroderma (SSc), myositis, or lupus nephritis.

In some aspects, the antibody or antigen-binding fragment thereof suppresses the type I IFN GS by at least 10%, at least 20%, at least 30% or at least 40% as compared to the type I IFN GS of the subject prior to the administration of the fixed dose of the antibody or antigen-binding fragment thereof. In some aspects, the therapeutic agent suppresses the type I IFN GS by at least 10%, at least 20%, at least 30% or at least 40% as compared to the average type I IFN GS signature in a population.

The present disclosure also provides a kit for detecting a type I IFN genetic signature (IFN GS) common to two diseases whose pathogeneses are mediated by type I IFN comprising a set of diagnostic assays capable of measuring differentially regulated pharmacodynamic (PD) marker genes in a patient sample, wherein the type I IFN GS is suppressed by the administration of a fixed dose of an antibody or antigen-binding fragment thereof that modulates type I IFN activity. In some aspects, the type I IFN GS comprises up-regulated expression or activity of at least four PD marker genes selected from the group consisting of IF16, RSAD2, IF144, IF144L, IF127, MX1, IFIT1, HERC5, ISG15, LAMP3, OAS3, OAS1, EPST1, IFIT3, LY6E, OAS2, PLSCR1, SIGLEC1, USP18, RTP4, and DNAPTP6. In other aspects, the type I IFN GS comprises up-regulated expression or activity of at least five of the PD marker genes. In some aspects, the type I IFN GS comprises up-regulated expression or activity of genes IF127, IF144, IF144L, and RSAD2. In some aspects, the type I IFN GS further comprises up-regulated expression or activity of gene IF16. In some aspects, the patient sample is blood or a fraction thereof, muscle, skin, or a combination thereof. In other aspects, the diagnostic assays comprise nucleic acid probes which hybridize to mRNA in the patient sample.

The present disclosure also provides a computer-implemented method for predicting an optimal dosage regimen with an antibody or antigen-binding fragment thereof that modulates type I IFN activity. This method comprises (a) inputting PK/PD data from a second type I IFN-mediated disease or disorder into a computer system comprising a pharmacokinetic-pharmacodynamic (PK/PD) stochastic model based on PK/PD data corresponding a first type I IFN-mediated disease or disorder, wherein the inputted PK/PD data from the second type I IFN-mediated disease or disorder is used to adjust the PK/PD stochastic model; (b) applying the adjusted PK/PD stochastic model to the inputted PK/PD data from the second type I IFN-mediated disease or disorder; and, (c) identifying an optimal dosage of the antibody or antigen-binding fragment thereof that modulates type I IFN activity for the second type I IFN-mediated disease or disorder from the output of the adjusted PK/PD stochastic model.

The present disclosure also provides a computer-implemented method of identifying an antibody or antigen-binding fragment thereof that modulates type I IFN activity as a candidate therapeutic agent for treating a type I IFN-mediated disease or disorder. This method comprises (a) inputting PD/PK data from a second type I IFN-mediated disease or disorder into a computer system comprising a PK/PD stochastic model based on PK/PD values corresponding a first type I IFN-mediated disease or disorder, wherein the inputted PD/PK data from the second type I IFN-mediated disease or disorder is used to adjust the PK/PD stochastic model; (b) applying the adjusted PK/PD stochastic model to the inputted data from the second type I IFN-mediated disease or disorder; and, (c) identifying an antibody or antigen-binding fragment thereof that modulates type I IFN activity as a candidate therapeutic agent for treating the second type I IFN-mediated disease or disorder from the output of the adjusted PK/PD stochastic model.

The present disclosure also provides a computer-implemented method of identifying a patient as a candidate for therapy with an antibody or antigen-binding fragment thereof that modulates type I IFN activity. This method comprises (a) inputting PD/PK data from a second type I IFN-mediated disease or disorder into a computer system comprising a PK/PD stochastic model based on PK/PD data corresponding a first type I IFN-mediated disease or disorder, wherein the inputted PD/PK data from the second type I IFN-mediated disease is used to adjust the PK/PD stochastic model; applying the adjusted PK/PD stochastic model to the inputted PD/PK data from the second type I IFN-mediated disease or disorder; and, identifying a patient with the second disease as a candidate for therapy with an antibody or antigen-binding fragment thereof that modulates type I IFN activity for the second type I IFN-mediated disease from the output of the adjusted PK/PD stochastic model.

The present disclosure also provides a computer-implemented method of designing a personalized therapy for treating a type I IFN-mediated disease or disorder with an antibody or antigen binding fragment thereof that modulates type I IFN activity. This method comprises (a) inputting PD/PK data from a second type I IFN-mediated disease or disorder into a computer system comprising a PK/PD stochastic model based on PK/PD data corresponding a first type I IFN-mediated disease or disorder, wherein the inputted data from the second type I IFN-mediated disease or disorder is used to adjust the PK/PD stochastic model; (b) applying the adjusted PK/PD stochastic model to the inputted PD/PK data from the second type I IFN-mediated disease or disorder; and, (c) identifying a personalized therapy for treating a type I IFN-mediated disease or disorder with an antibody or antigen binding fragment thereof that modulates type I IFN activity for the second type I IFN-mediated disease or disorder from the output of the adjusted PK/PD stochastic model.

In some aspects, the type I IFN activity in the computer-implemented method is IFN-α activity. In some aspects, the first and second type I IFN-mediated disease or disorder in the computer-implemented method share a common type I IFN GS. In some aspects, the type I IFN GS in the computer-implemented method is differentially regulated.

In some aspects, the type I IFN GS in the computer-implemented method comprises up-regulated expression or activity of at least 4 PD marker genes selected from the group consisting of IF16, RSAD2, IF144, IF144L, IF127, MX1, IFIT1, HERC5, ISG15, LAMP3, OAS3, OAS1, EPST1, IFIT3, LY6E, OAS2, PLSCR1, SIGLEC1, USP18, RTP4, and DNAPTP6. In some aspects, the type I IFN GS in the computer-implemented method comprises up-regulated expression or activity of at least 5 PD marker genes selected from the group consisting of IF16, RSAD2, IF144, IF144L, IF127, MX1, IFIT1, HERC5, ISG15, LAMP3, OAS3, OAS1, EPST1, IFIT3, LY6E, OAS2, PLSCR1, SIGLEC1, USP18, RTP4, and DNAPTP6. In some aspects, the type I IFN GS in the computer-implemented method comprises up-regulated expression or activity of genes IF127, IF144, IF144L, and RSAD2. In some aspects, the type I IFN GS in the computer-implemented method further comprises up-regulated expression or activity of gene IF16.

In some aspects, the antibody or antigen binding fragment thereof in the computer-implemented method specifically binds to an IFN receptor. In other aspects, the IFN receptor in the computer-implemented method is an IFN alpha receptor. In other aspects, the IFN alpha receptor in the computer-implemented method is IFNAR1. In other aspects, the antibody or antigen binding fragment thereof in the computer-implemented method specifically binds to subunit 1 of IFNAR1. In other aspects, the antibody or antigen binding fragment thereof in the computer-implemented method is monoclonal.

In some aspects, the antibody or antigen binding fragment thereof in the computer-implemented method comprises an immunoglobulin IgG Fc region. In other aspects, the antibody in the computer-implemented method is MEDI-546. In some aspects, the first and the second type I IFN-mediated disease or disorder in the computer-implemented method are autoimmune diseases. In some other aspects, the autoimmune diseases in the computer-implemented method are rheumatic diseases. In some aspects, the rheumatic diseases in the computer-implemented method are selected from the group consisting of systemic lupus erythematosus (SLE), scleroderma (SSc), myositis, and lupus nephritis.

In some aspects, the first type I IFN-mediated disease or disorder in the computer-implemented method is SSc and the second type I IFN-mediated disease or disorder is SLE. In some aspects, the first type I IFN-mediated disease or disorder in the computer-implemented method is SSc and the second type I IFN-mediated disease or disorder is myositis. In some aspects, the first type I IFN-mediated disease or disorder in the computer-implemented method is SSc and the second type I IFN-mediated disease or disorder is lupus nephritis.

In other aspects, the PK/PD data in the computer-implemented method corresponding to the first or second type I IFN-mediated disease or disorder comprises binding affinity data. In some aspects, the binding affinity data in the computer-implemented method corresponds to the binding of an antibody or antigen binding fragment thereof to an IFN receptor. In other aspects, the antibody or antigen binding fragment thereof in the computer-implemented method is MEDI-546. In some aspects, the IFN receptor in the computer-implemented method is IFNAR1.

In some aspects, the PK/PD data corresponding the first or second type I IFN-mediated disease or disorder in the computer-implemented method comprises kinetics data. In other aspects, the kinetics data corresponds to internalization kinetics of an antigen-antibody complex by cells. In some aspects, the antigen in the computer-implemented method is IFNAR1. In other aspects, the antibody in the computer-implemented method is MEDI-546. In some aspects, the cells in the computer-implemented method are THP-1 cells.

In some aspects, the PK/PD data corresponding to the first or second type I IFN-mediated disease or disorder in the computer-implemented method comprises type I IFN GS suppression data. In some aspects, the type I IFN GS suppression in the computer-implemented method is full suppression. In some aspects, the type I IFN GS suppression in the computer-implemented method is partial suppression. In some aspects, the type I IFN GS in the computer-implemented method comprises up-regulated expression or activity of genes IF127, IF144, IF144L, RSAD2, and IF16.

In some aspects, the PK/PD stochastic model comprises two compartments. In some aspects, the two compartments in the PK/PD stochastic model are a central compartment and a peripheral compartment. In some aspects, the PK/PD stochastic model further comprises a skin compartment. In some aspects, the PK/PD stochastic model comprises two elimination pathways. In some aspects, the two elimination pathways are a clearance pathway and a target-mediated disposition pathway. In one specific aspect, the clearance pathway in the PK/PD stochastic model is a reticuloendothelial system pathway.

The present disclosure also provides a computer-readable medium containing program instructions for predicting an optimal dosage regimen with an antibody or antigen-binding fragment thereof that modulates type I IFN activity, wherein execution of the program instructions by one or more processors of a computer system causes the one or more processors to carry out the steps of (a) processing inputted PK/PD data from a second type I IFN-mediated disease or disorder; (b) adjusting a PK/PD stochastic model based on PK/PD data corresponding a first type I IFN-mediated disease or disorder with the processed PK/PD data from the second type I IFN-mediated disease or disorder; and, (c) executing a stochastic simulation applying the adjusted PK/PD stochastic model to the inputted PK/PD data from the second type I IFN-mediated disease or disorder; wherein the output of the simulation identifies an optimal dosage of the antibody or antigen-binding fragment thereof that modulates type I IFN activity in the second type I IFN-mediated disease or disorder.

The present disclosure also provides a computer-readable medium containing program instructions for identifying an antibody or antigen-binding fragment thereof that modulates type I IFN activity as a candidate therapeutic agent for treating a type I IFN-mediated disease or disorder, wherein execution of the program instructions by one or more processors of a computer system causes the one or more processors to carry out the steps of (a) processing inputted PK/PD data from a second type I IFN-mediated disease or disorder; (b) adjusting a PK/PD stochastic model based on PK/PD data corresponding a first type I IFN-mediated disease or disorder with the processed PK/PD data from the second type I IFN-mediated disease or disorder; and, (c) executing a stochastic simulation applying the adjusted PK/PD stochastic model to the inputted PK/PD data from the second type I IFN-mediated disease or disorder; wherein the output of the simulation identifies an antibody or antigen-binding fragment thereof that modulates type I IFN activity as a candidate therapeutic agent for treating the second type I IFN-mediated disease or disorder.

The present disclosure also provides a computer-readable medium containing program instructions for identifying a patient as a candidate for therapy with an antibody or antigen-binding fragment thereof that modulates type I IFN activity, wherein execution of the program instructions by one or more processors of a computer system causes the one or more processors to carry out the steps of (a) processing inputted PK/PD data from a second type I IFN-mediated disease or disorder; (b) adjusting a PK/PD stochastic model based on PK/PD data corresponding a first type I IFN-mediated disease or disorder with the processed PK/PD data from the second type I IFN-mediated disease or disorder; and, (c) executing a stochastic simulation applying the adjusted PK/PD stochastic model to the inputted PK/PD data from the second type I IFN-mediated disease or disorder; wherein the output of the simulation identifies a patient with the second type I IFN-mediated disease as a candidate for therapy with an antibody or antigen-binding fragment thereof that modulates type I IFN activity.

The present disclosure also provides a computer-readable medium containing program instructions for designing a personalized therapy for treating a type I IFN-mediated disease or disorder with an antibody or antigen binding fragment thereof that modulates type I IFN activity, wherein execution of the program instructions by one or more processors of a computer system causes the one or more processors to carry out the steps of (a) processing inputted PK/PD data from a second type I IFN-mediated disease or disorder; (b) adjusting a PK/PD stochastic model based on PK/PD data corresponding a first type I IFN-mediated disease or disorder with the processed PK/PD data from the second type I IFN-mediated disease or disorder; and, (c) executing a stochastic simulation applying the adjusted PK/PD stochastic model to the inputted PK/PD data from the second type I IFN-mediated disease or disorder; wherein the output of the simulation identifies a personalized therapy for treating the second type I IFN-mediated disease or disorder with an antibody or antigen binding fragment thereof that modulates type I IFN activity. In some aspects of the computer-readable medium, the type I IFN activity is IFN-$\alpha$ activity. In other aspects of the computer-readable medium, the first and second type I IFN-mediated disease or disorder share a common IFN GS. In some aspects of the computer-readable medium, the type I IFN GS is differentially regulated.

In some aspects of the computer-readable medium, the type I IFN GS comprises up-regulated expression or activity of at least 4 PD marker genes selected from the group consisting of IFI6, RSAD2, IFI44, IFI44L, IFI27, MX1, IFIT1, HERC5, ISG15, LAMP3, OAS3, OAS1, EPSTI1, IFIT3, LY6E, OAS2, PLSCR1, SIGLEC1, USP18, RTP4, and DNAPTP6. In some aspects of the computer-readable medium, the type I IFN GS comprises up-regulated expression or activity of at least 5 PD marker genes selected from the group consisting of IFI6, RSAD2, IFI44, IFI44L, IFI27, MX1, IFIT1, HERC5, ISG15, LAMP3, OAS3, OAS1, EPSTI1, IFIT3, LY6E, OAS2, PLSCR1, SIGLEC1, USP18, RTP4, and DNAPTP6. In some aspects of the computer-readable medium, the type I IFN GS comprises up-regulated expression or activity of genes IFI27, IFI44, IFI44L, and RSAD2. In some aspects of the computer-readable medium, the type I IFN GS further comprises up-regulated expression or activity of gene IFI6.

In some aspects of the computer-readable medium, the antibody or antigen binding fragment thereof specifically binds to an IFN receptor. In some aspects of the computer-readable medium, the IFN receptor is an IFN alpha receptor. In some aspects of the computer-readable medium, the IFN alpha receptor is IFNAR1. In some aspects of the computer-readable medium, the antibody or antigen binding fragment thereof specifically binds to subunit 1 of IFNAR1. In some aspects of the computer-readable medium, the antibody or antigen binding fragment thereof is monoclonal. In some aspects of the computer-readable medium, the antibody or antigen binding fragment thereof comprises an immunoglobulin IgG Fc region. In some aspects of the computer-readable medium, the antibody is MEDI-546.

In some aspects of the computer-readable medium, the first and the second type I IFN-mediated disease or disorder are autoimmune diseases. In some aspects of the computer-readable medium, the autoimmune diseases are rheumatic diseases. In some aspects of the computer-readable medium, the rheumatic diseases are selected from the group consisting of systemic lupus erythematosus (SLE), scleroderma (SSc), myositis, and lupus nephritis. In some aspects of the computer-readable medium, the first type I IFN-mediated disease or disorder is SSc and the second type I IFN-mediated disease or disorder is SLE. In some aspects of the computer-readable medium, the first type I IFN-mediated disease or disorder is SSc and the second type I IFN-mediated disease or disorder is myositis. In some aspects of the computer-readable medium, the first type I IFN-mediated disease or disorder is SSc and the second type I IFN-mediated disease or disorder is lupus nephritis.

In some aspects of the computer-readable medium, the PK/PD data corresponding to the first or second type I IFN-mediated disease or disorder comprise binding affinity data. In some aspects of the computer-readable medium, the binding affinity data corresponds to the binding of an antibody or antigen binding fragment thereof to an IFN receptor. In some aspects of the computer-readable medium, the antibody or antigen binding fragment thereof is MEDI-546. In some aspects of the computer-readable medium, the IFN receptor is IFNAR1.

In some aspects of the computer-readable medium, the PK/PD data corresponding the first or second type I IFN-mediated disease or disorder comprise kinetics data. In some aspects of the computer-readable medium, the kinetics data is corresponds to internalization kinetics of an antigen-antibody complex by cells. In some aspects of the computer-readable medium, the antigen is IFNAR1. In some aspects of the computer-readable medium, the antibody is MEDI-546. In some aspects of the computer-readable medium, the cells are THP-1 cells.

In some aspects of the computer-readable medium, the PK/PD data corresponding the first or second type I IFN-mediated disease or disorder comprise type I IFN GS suppression data. In some aspects of the computer-readable medium, the type I IFN GS suppression is full suppression. In some aspects of the computer-readable medium, the type I IFN GS suppression is partial suppression. In some aspects of the computer-readable medium, the IFN GS comprises up-regulated expression or activity of genes IF127, IF144, IF144L, RSAD2, and IF16.

In some aspects of the computer-readable medium, the PK/PD stochastic model comprises two compartments. In some aspects of the computer-readable medium, the two compartments in the PK/PD stochastic model are a central compartment and a peripheral compartment. In some aspects of the computer-readable medium, the PK/PD stochastic model further comprises a skin compartment. In some aspects of the computer-readable medium, the PK/PD stochastic model comprises two elimination pathways. In some aspects of the computer-readable medium, the two elimination pathways in the PK/PD stochastic model are a clearance pathway and a target-mediated disposition pathway. In some aspects of the computer-readable medium, the clearance pathway in the PK/PD stochastic model is a reticuloendothelial system pathway.

BRIEF DESCRIPTION OF THE DRAWINGS/FIGURES

FIG. 1 shows baseline type I IFN Gene Signature (type I IFN GS) scores for SLE (whole blood, WB: 262, skin: 17), SSc (whole blood, WB: 28, skin: 16), and healthy control patients (whole blood, WB: 54, skin: 30) in both blood and skin specimens. Horizontal summary lines indicate the mean and standard error for each distribution of type I IFN GS scores.

Figure 2A:
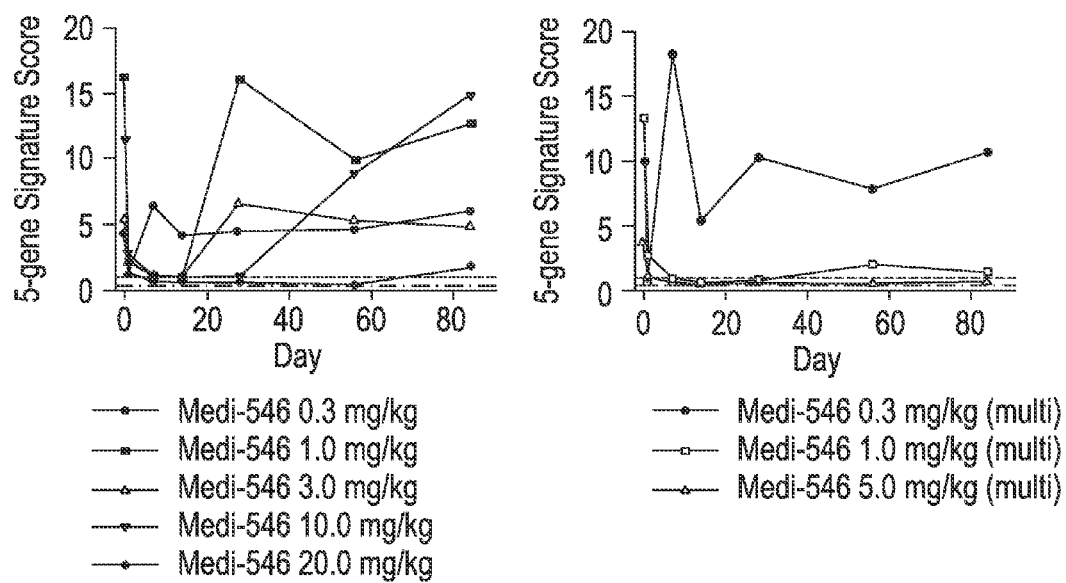
Figure 2B:
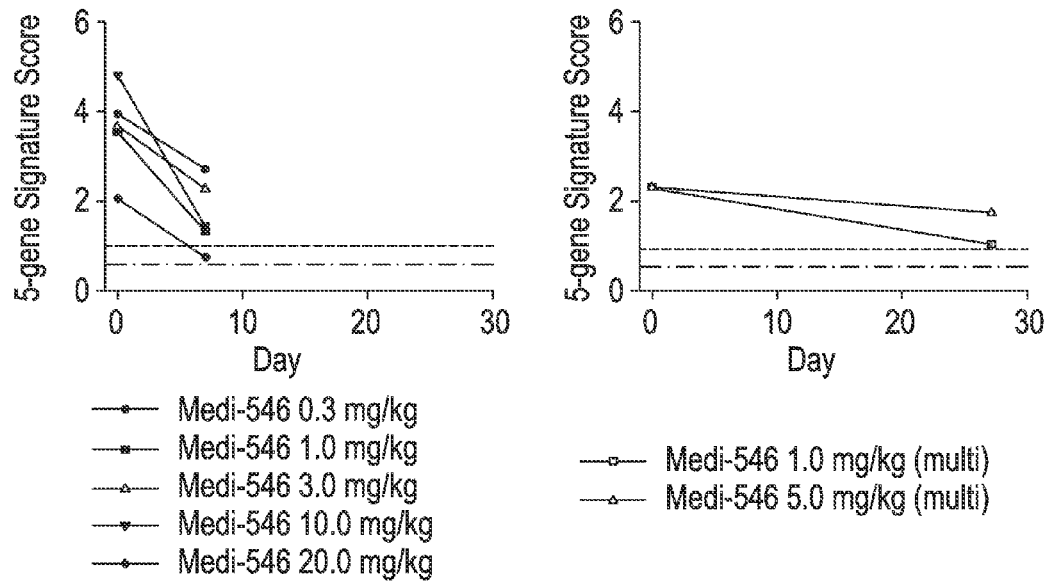
Figure 2C:
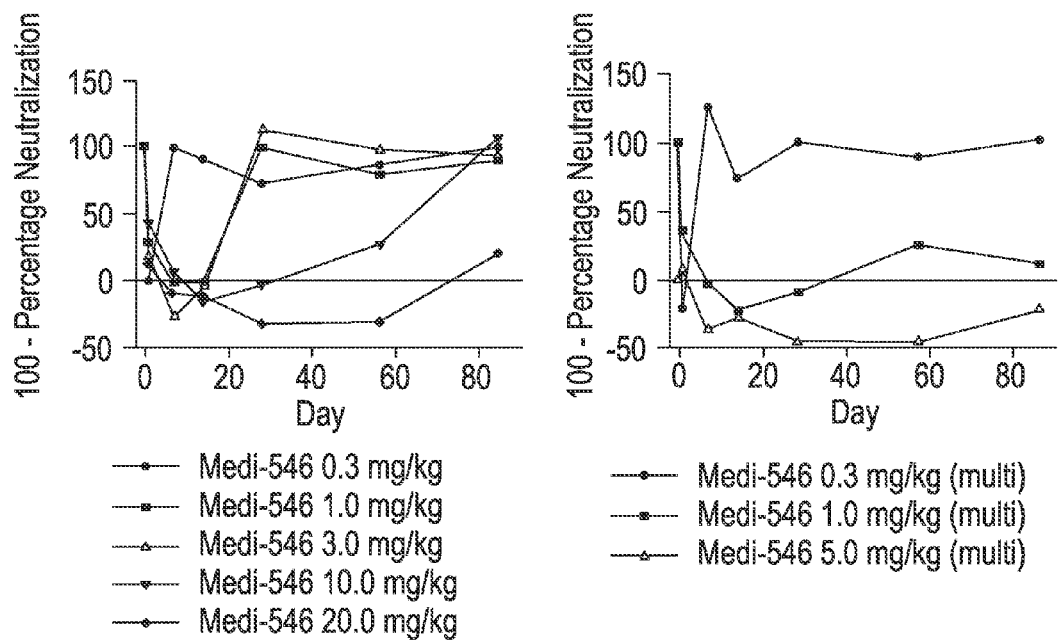
Figure 2D:
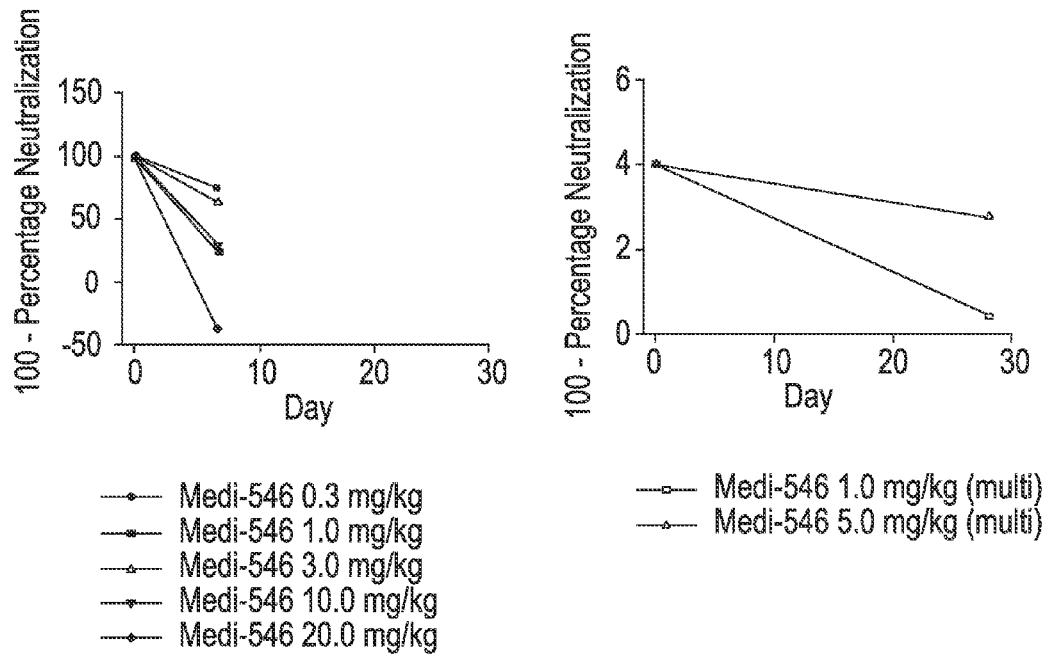

FIGS. 2A to 2D shows median type I IFN GS profiles (FIG. 2A and FIG. 2B) and percent remaining type I IFN GS (FIG. 2C and FIG. 2D) in diffuse SSc patients following single or multiple IV administrations of MEDI-546 in whole blood specimens (FIG. A and FIG. 2C) or skin specimens (FIG. 2B and FIG. 2D) from MI-CP180 trial. For each pair of plots, the single and multiple dose treatment cohorts have been separated into their respective graph. X-axis represents time from the start of the study in days, where day 0 is pre treatment. Target modulation for each dose cohort is reported as a percentage from starting values of 100%, so each point post treatment for each cohort indicates the median percentage of remaining GS. Only baseline positive $GS_0$ score SSc patients were plotted. The minimum and average GS score among the pool of normal healthy controls are shown as the black dashed line and grey dashed line respectively (FIG. 2A and FIG. 2B).

Figure 3A:
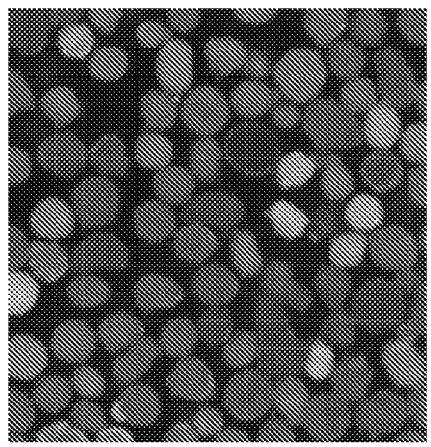
Figure 3B:
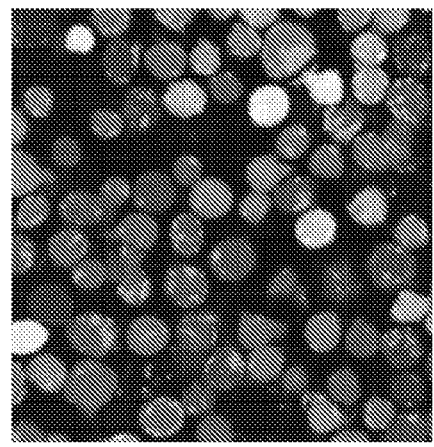
Figure 3C:
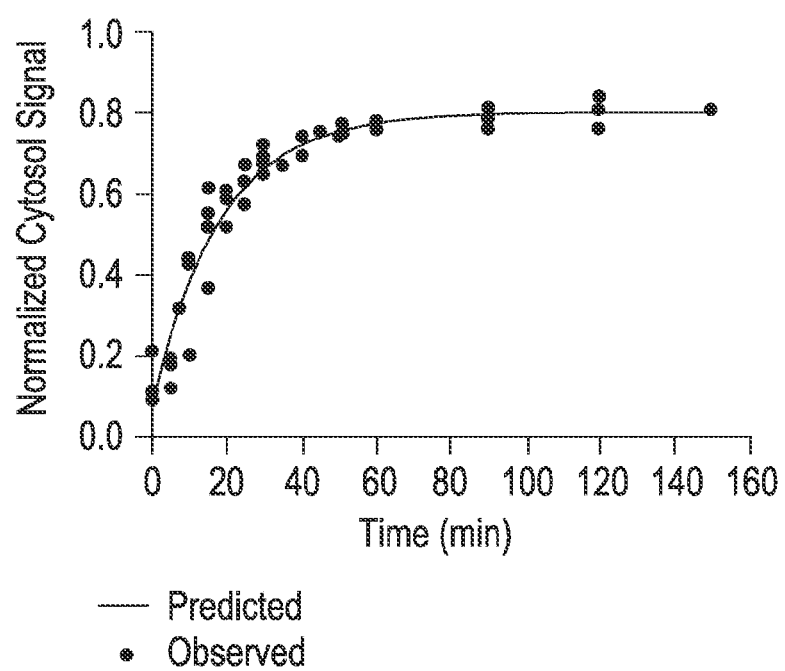

FIG. 3 shows the measurement of MEDI-546 internalization rate in THP-1 cells by confocal fluorescence imaging studies. Cells were stained with CFSE (cytosol) and MEDI-546-Alexa647. Internalization was initiated by transferring cells from ice to 37° C. Overlays of CFSE and MEDI-546-Alexa647 fluorescent images are shown before (FIG. 3A) and 40 min after the start of internalization (FIG. 3B). MEDI-546-Alexa647 fluorescence signals in cytoplasm were normalized to total fluorescence and plotted versus time (FIG. 3C). Each data point represents the average of triplicates in an experiment. The graph combined data obtained from four independent experiments.

Figure 4:
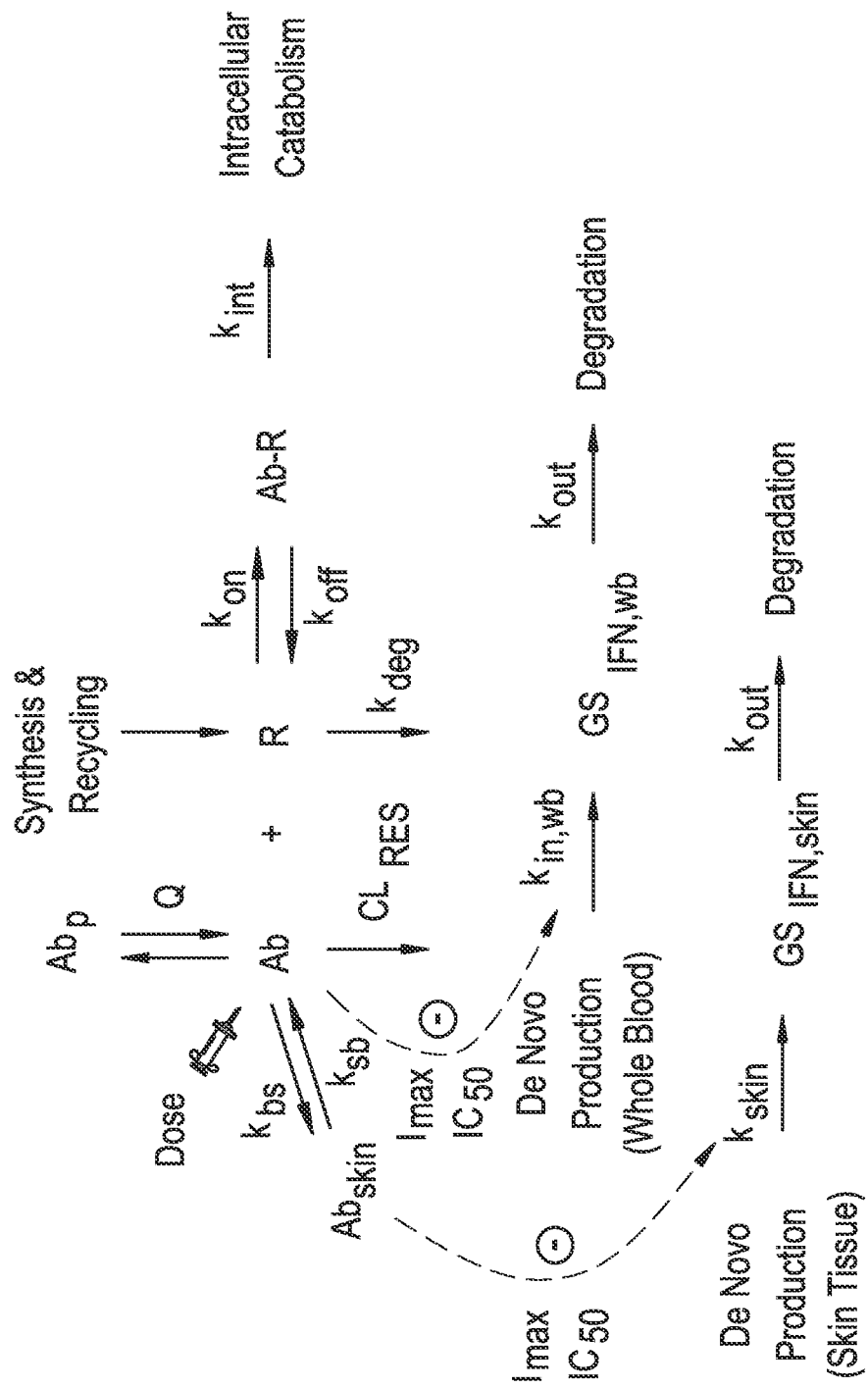

FIG. 4 shows the MEDI-546 PK-PD model structure. Ab, $Ab_p$ and $Ab_{skin}$ are MEDI-546 in the central, peripheral and skin compartments, respectively. Q is the inter-compartmental clearance. The partitioning of MEDI-546 from blood (serum) to skin is represented by $k_{bs}$ and $k_{sb}$. $CL_{RES}$ represents the clearance by the reticuloendothelial system. MEDI-546 (Ab) binds to IFNAR1 (R) and the complex (Ab.R) is subsequently internalized and degraded inside the cells. $GS_{IFN,wb}$ and $GS_{IFN,skin}$ represent type I IFN GS in the whole blood and skin, respectively. $I_{max}$ is the maximum fractional extent of inhibition of type I IFN GS production by MEDI-546, and $IC_{50}$ is potency (MEDI-546 concentration corresponding to half maximum inhibition of type I IFN GS production). $k_{in}$ and $k_{out}$ are the production rate and elimination rate constant of IFN genes. The inclusion of the skin compartment is for simulation purpose only. There is no MEDI-546 mass loss from the central compartment due to the partitioning to the skin tissues.

FIGS. 5A to 5D show representative individual MEDI-546 PK and type I IFN GS profiles in diffuse SSc patients from the MI-CP180 clinical trial. FIGS. 5A and 5B correspond to PK and PD of single-dose phase, respectively. FIGS. 5C and 5D correspond to PK and PD of multiple-dose phase, respectively. Two patients were selected for each dose phase, one from a lower dose group and the other from a high dose group. Patients in the multiple-dose cohorts received four weekly intravenous administrations of MEDI-546; the last dose was given on Day 28. Open circles represent observed serum concentration of MEDI-546 or type I GS in peripheral blood. Grey lines are the population predictions while the black lines are individual predictions by the population PK-PD model. SD: single dose regimen, MD: multiple dose regimen, SID: subject ID.

Figure 6A:
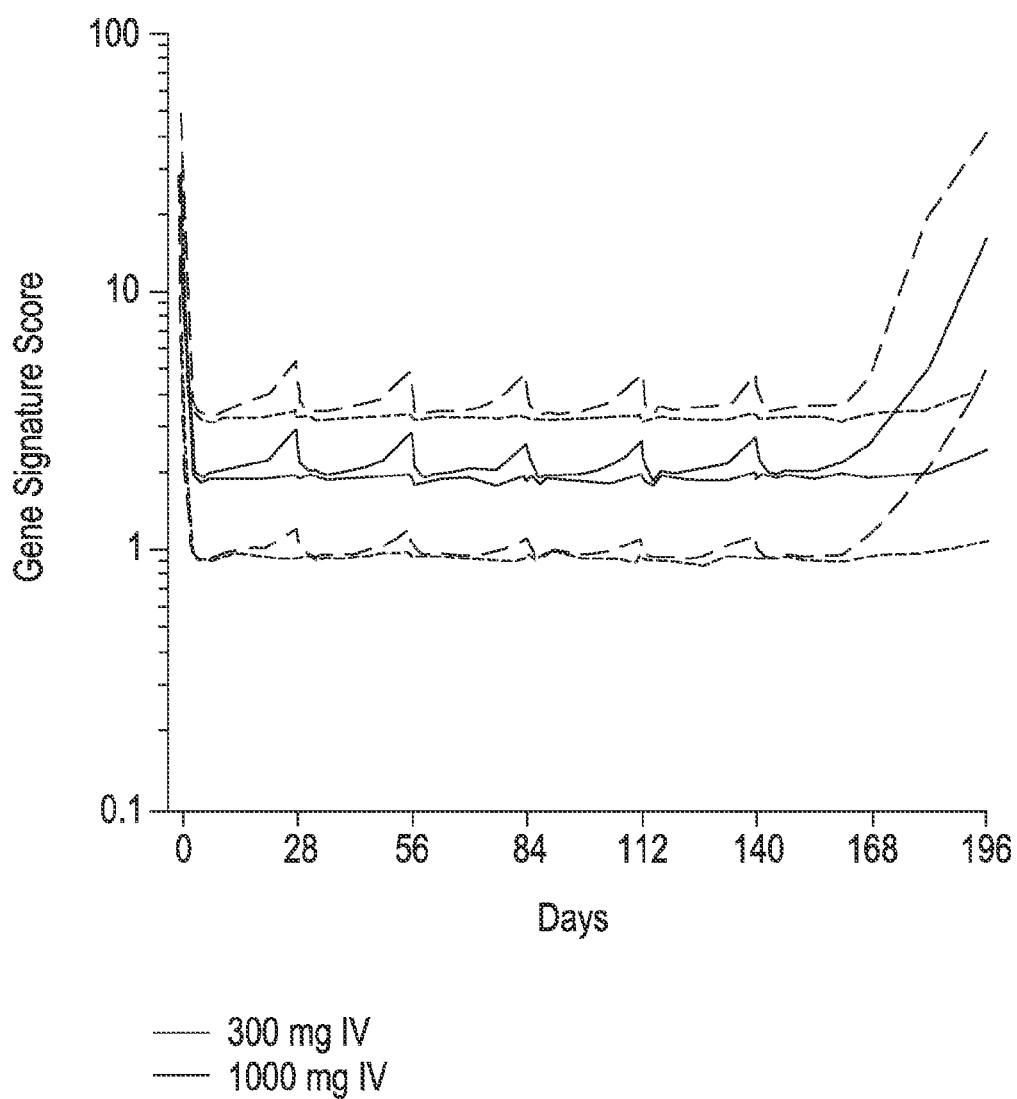

FIGS. 6A and 6B show simulated type I IFN GS profiles in peripheral blood (FIG. 6A) and skin tissue (FIG. 6B) of SLE patients upon multiple IV administrations of MEDI-546 (fixed dose) once every four weeks. The solid lines represent the medians of 1,000 simulated profiles while dotted lines represent the lower or upper quartiles. The observed upper boundary (mean+2 standard deviations) of the type I IFN GS in the blood and skin of healthy donors were 2.9 and 1.8, respectively.

Figure 7:
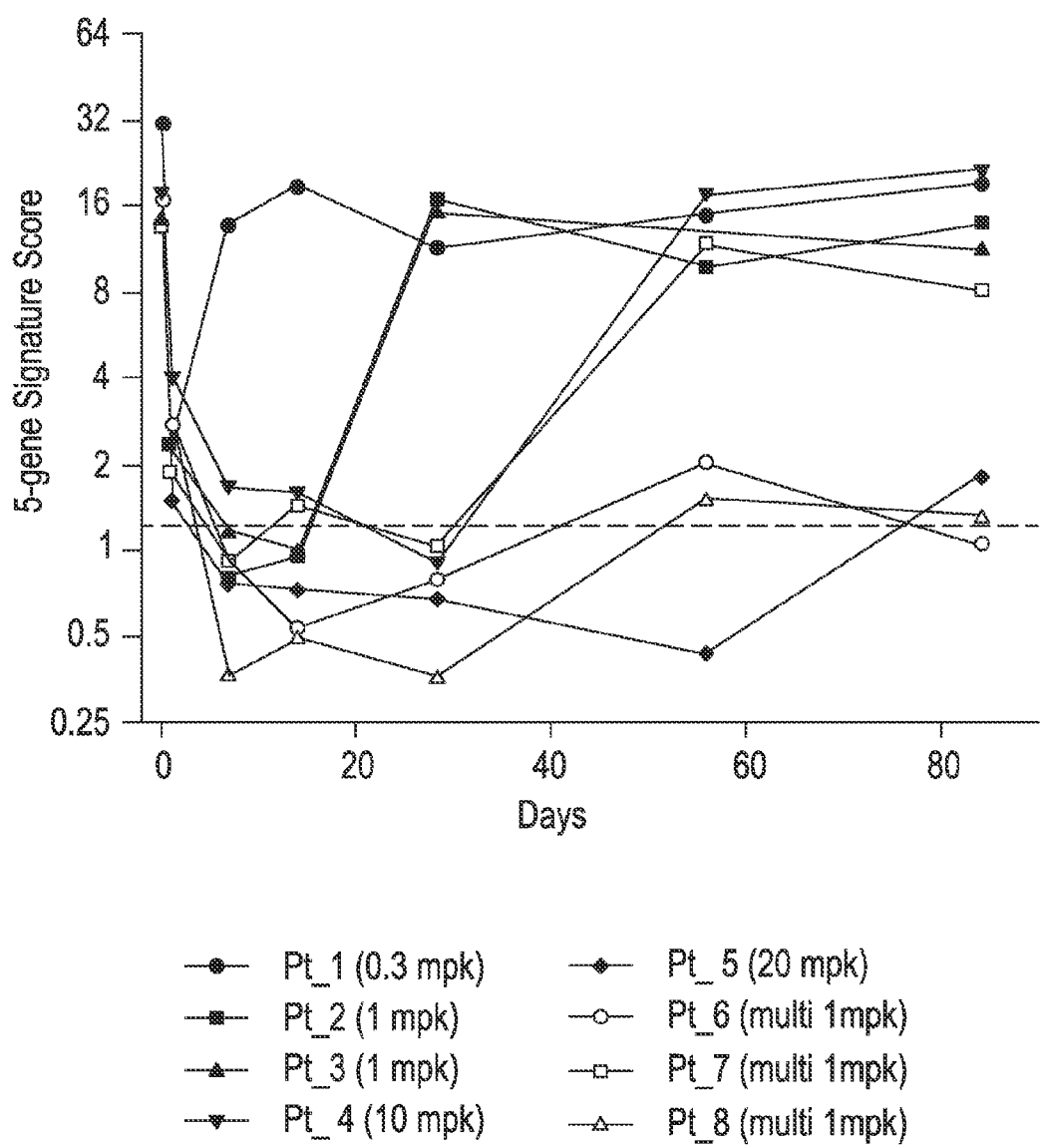

FIG. 7 shows the target modulation profiles in the blood of seven SSc patients with baseline $GS_0>13$ from the MI-CP180 clinical trial. Black and grey lines represent single dose (0.3, 1, 10 or 20 mg/kg) or multiple dose (1 mg/kg) regimens respectively; the grey dashed line represents the average value of type I IFN GS score (1.1) of the pool of normal healthy controls. Mpk=mg/kg.

Figure 8A:
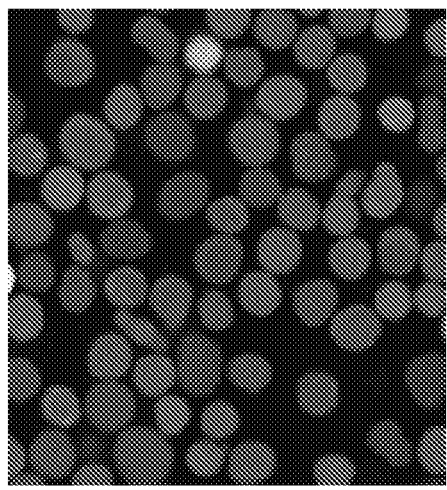
Figure 8B:
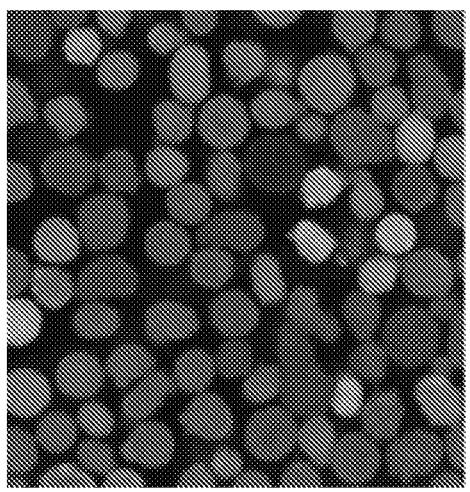

FIG. 8 shows the specific binding of MEDI-546 to THP-1 cells. Cells were stained with CFSE (cytosol) and either IgG-Alexa647 (A) or MEDI-546-Alexa647 (B). Overlays of CFSE and Alexa647 fluorescent images are shown from a representative experiment.

Figure 9A:
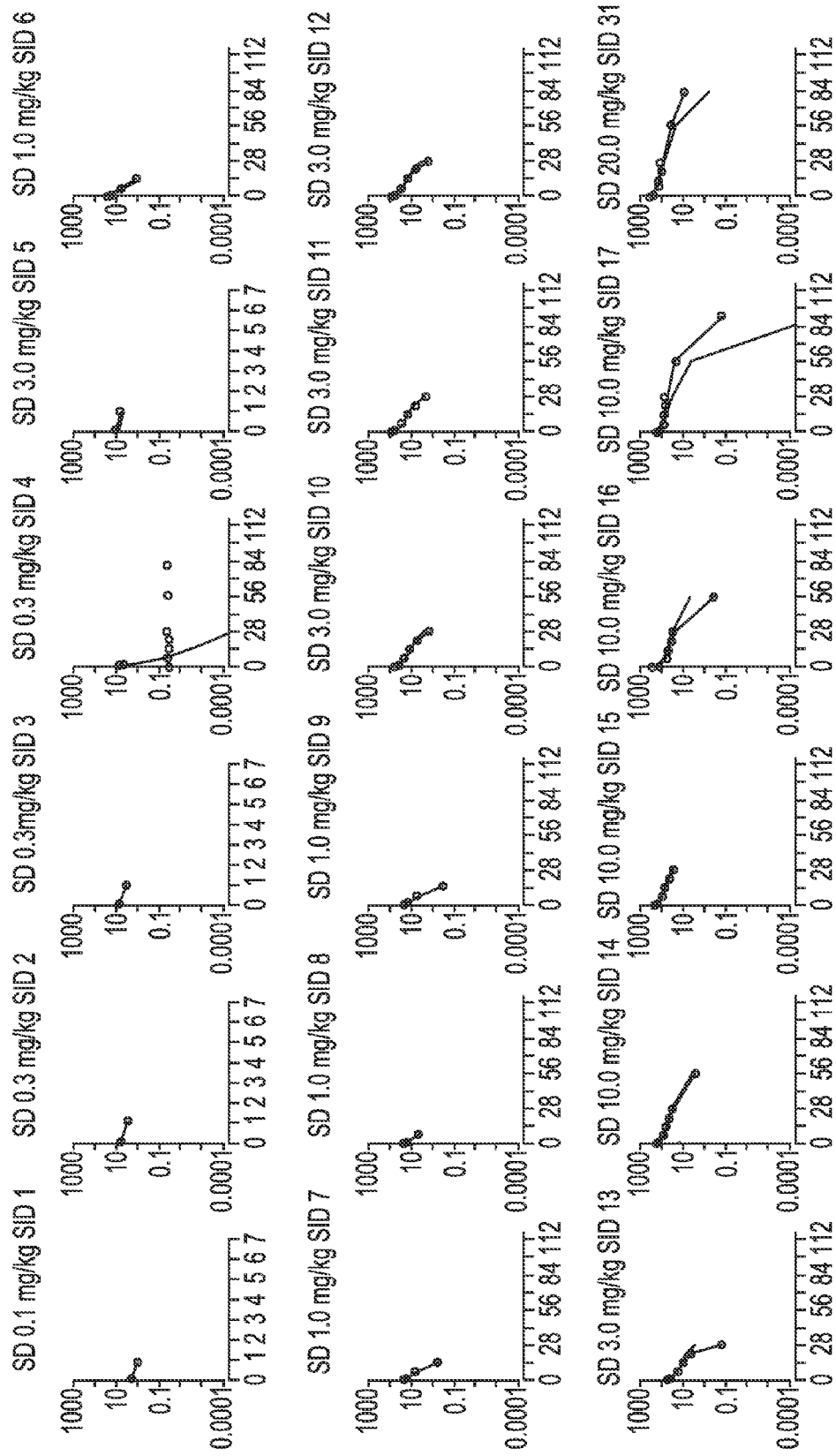
Figure 9B:
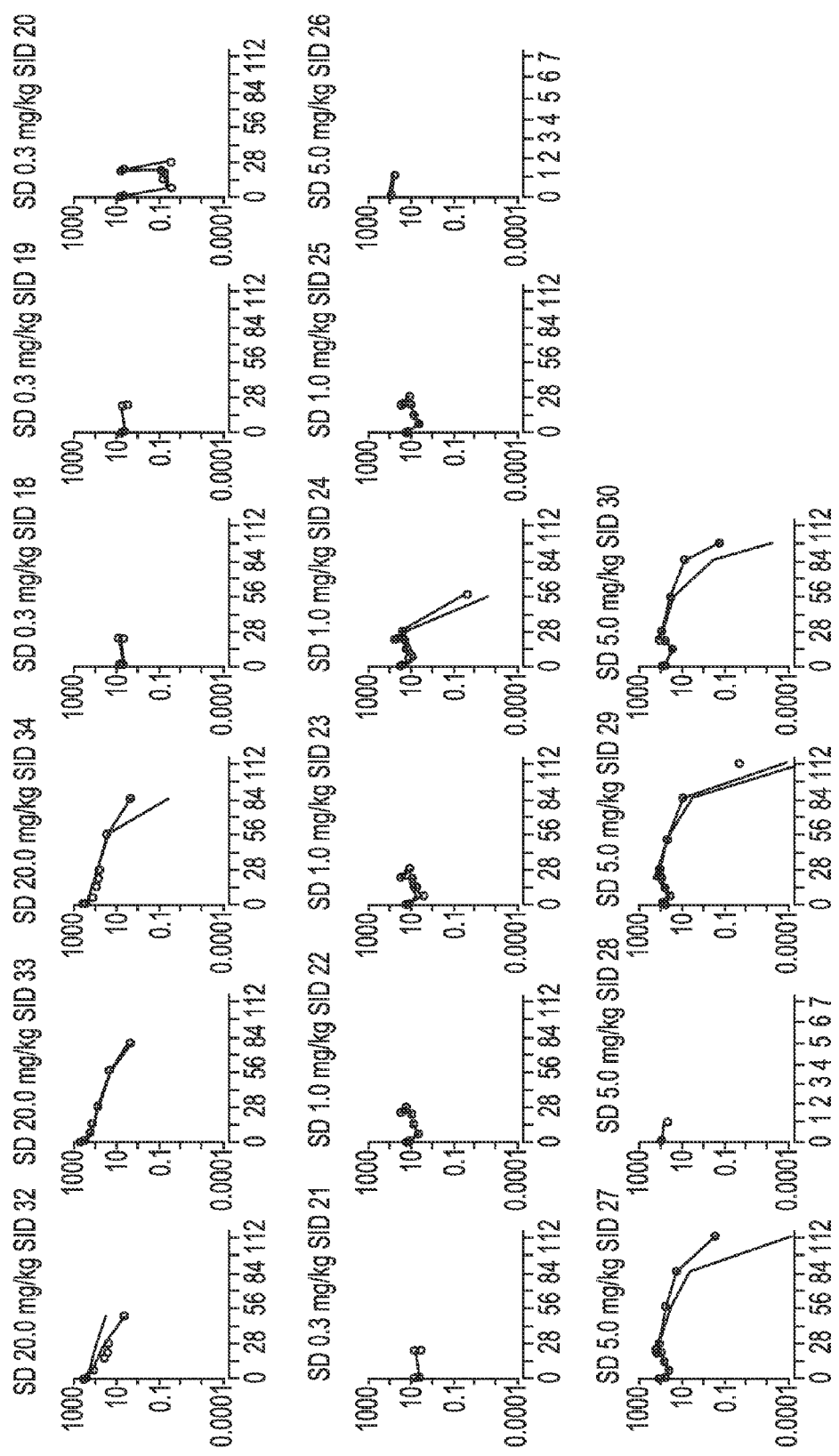

FIGS. 9A and 9B show observed and model-predicted MEDI-546 PK profiles in diffuse SSc patients. Patients enrolled in the multiple-dose cohorts received four weekly IV administrations of MEDI-546. Symbols represent observed values. The grey solid lines are the population predictions and the black solid lines are the individual predictions. SD: single-dose, MD: multiple-dose, SID: subject ID. X-axes represent days. Y-axes represent MEDI-546 concentrations (μg/mL).

Figure 10A:
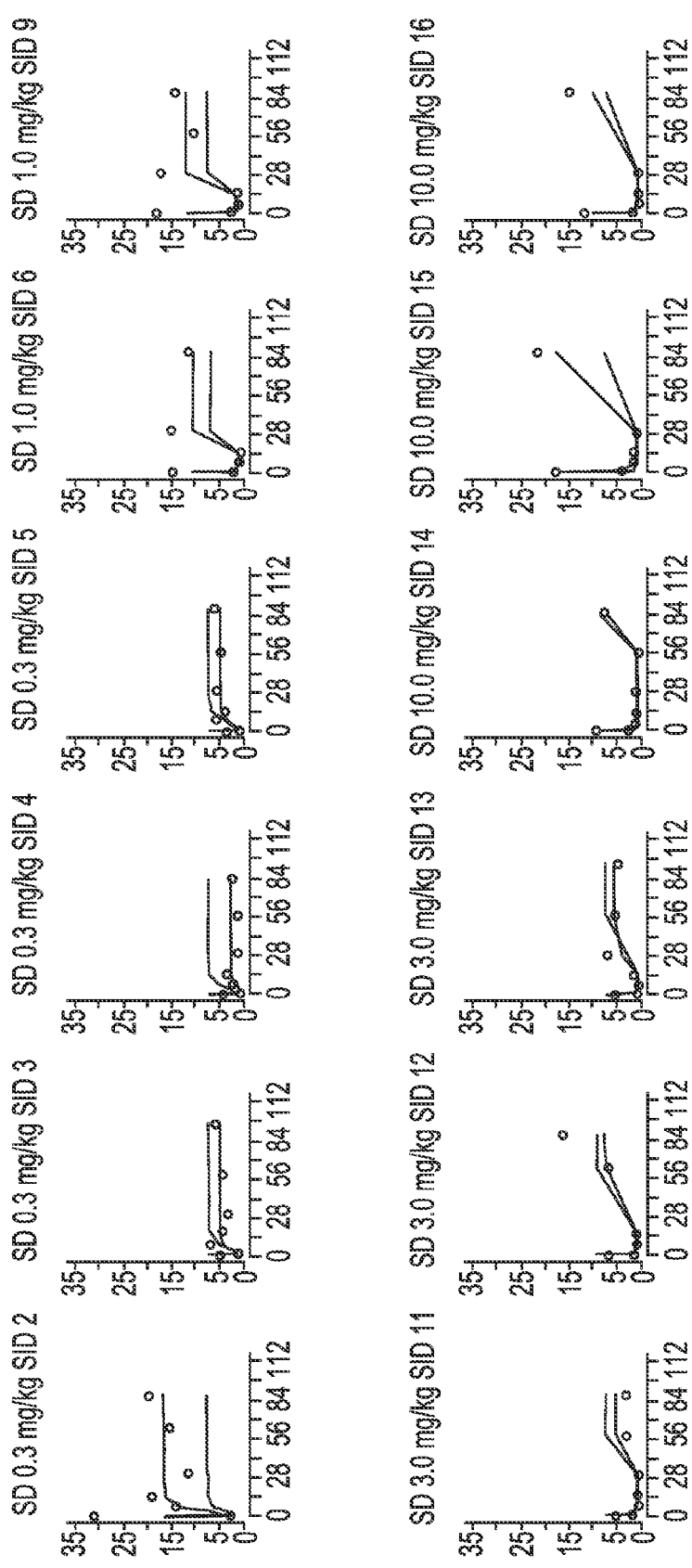
Figure 10B:
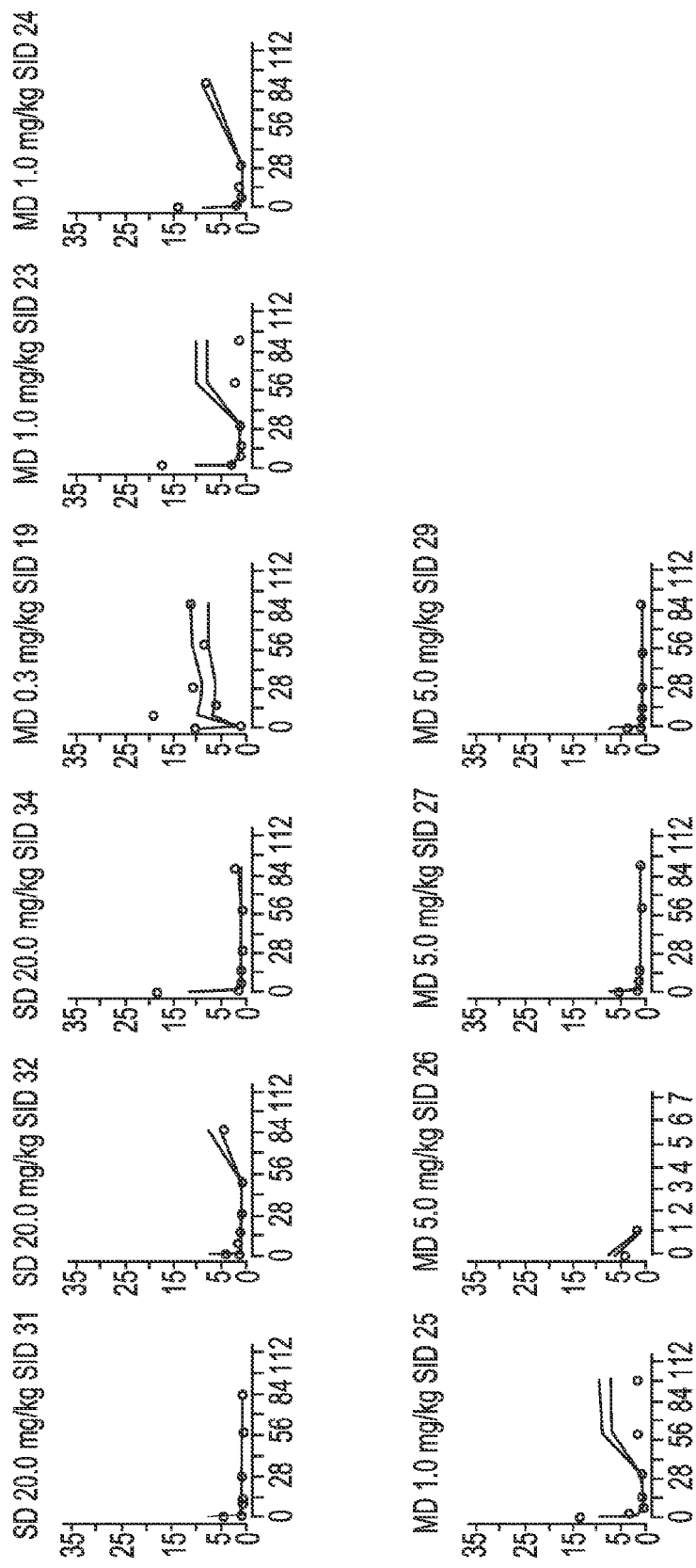

FIGS. 10A and 10B show observed and model-predicted blood type I IFN GS profiles in diffuse SSc patients. Patients enrolled in the multiple-dose cohorts received four weekly IV administrations of MEDI-546. Symbols represent observed values. The grey solid lines are the population predictions and the black solid lines are the individual predictions. SD: single-dose, MD: multiple-dose, SID: subject ID. X-axes represent days. Y-axes represent type I IFN GS scores.

Figure 11A:
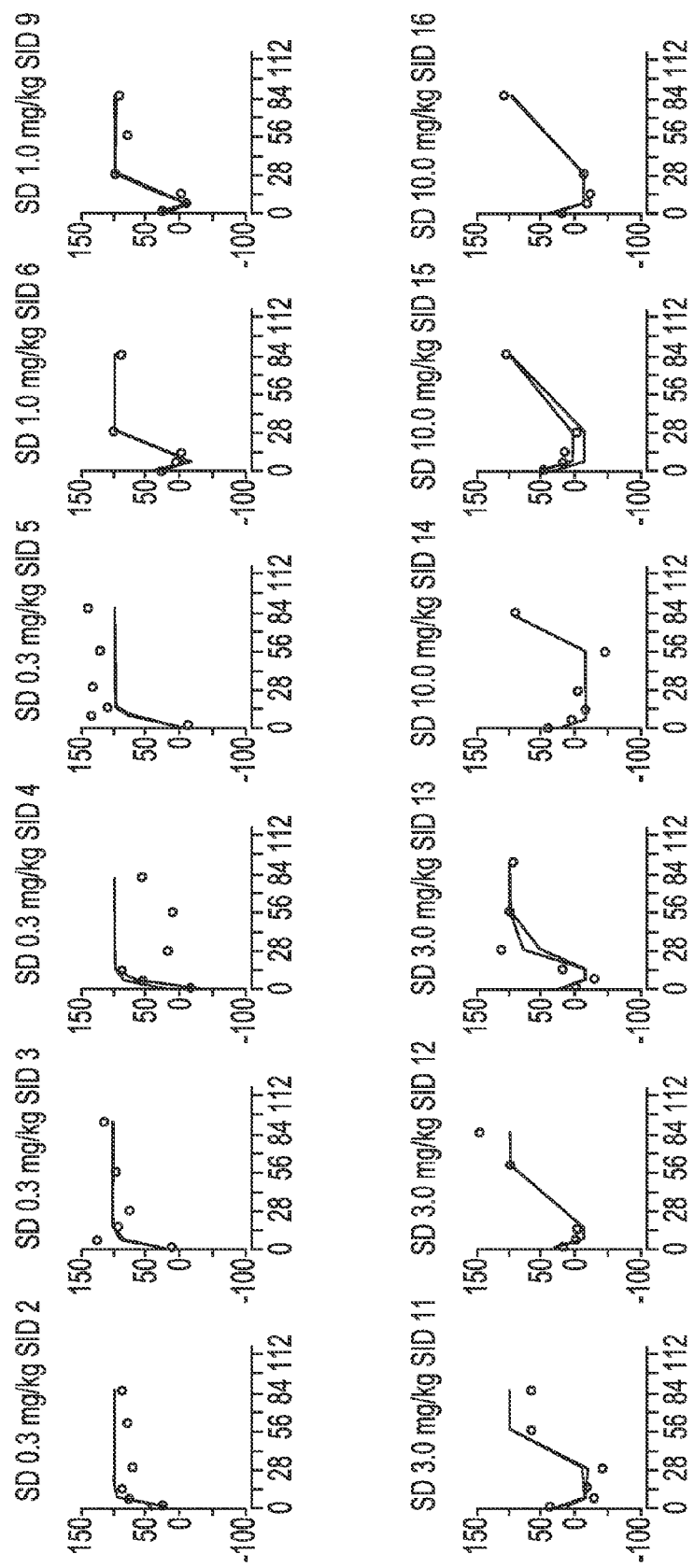
Figure 11B:
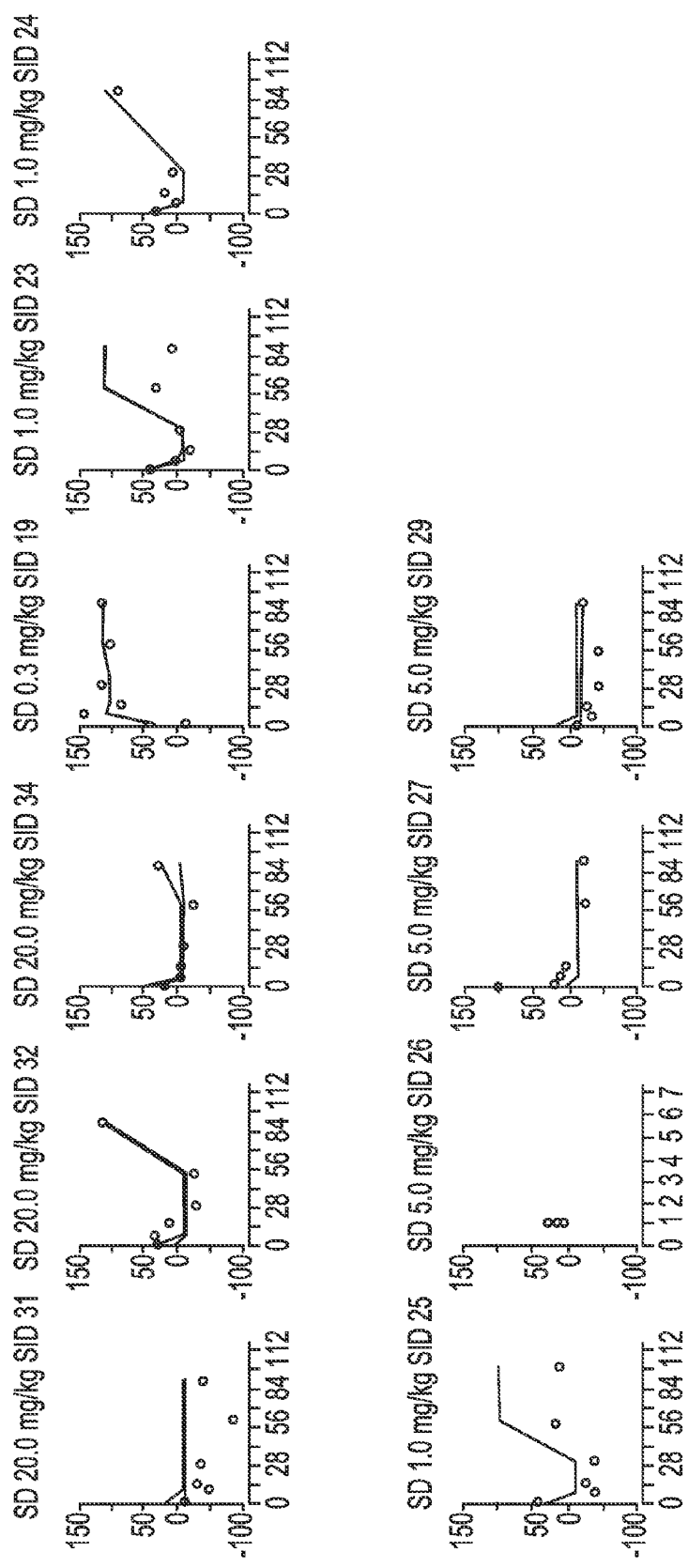

FIGS. 11A and 11B show observed and model-predicted Target Modulation in peripheral blood from diffuse SSc patients. Patients enrolled in the multiple-dose cohorts received four weekly IV administrations of MEDI-546. Symbols represent observed values. The grey solid lines are the population predictions and the black solid lines are the individual predictions. SD: single-dose, MD: multiple-dose, SID: subject ID. X-axes represent days. Y-axes represent (100%–Target Modulation) (%).

FIG. 12 shows visual predictive checks of MEDI-546 PK profiles in adult SSc patients. Symbols represent observed serum concentrations of MEDI-546. The solid lines are medians of 1,000 simulated replicates. The dashed lines represent 5th/95th or 10th/90th percentiles from 1,000 simulations using the population PK-PD model.

FIG. 13 shows visual predictive checks of type I IFN GS responses in adult SSc patients following MEDI-546 administration. Symbols represent observed type I IFN GS in peripheral blood. The solid lines are medians of 1,000 simulated replicates. The dashed lines represent 5th/95th or 10th/90th percentiles from 1,000 simulations using the population PK-PD model.

Figure 14A:
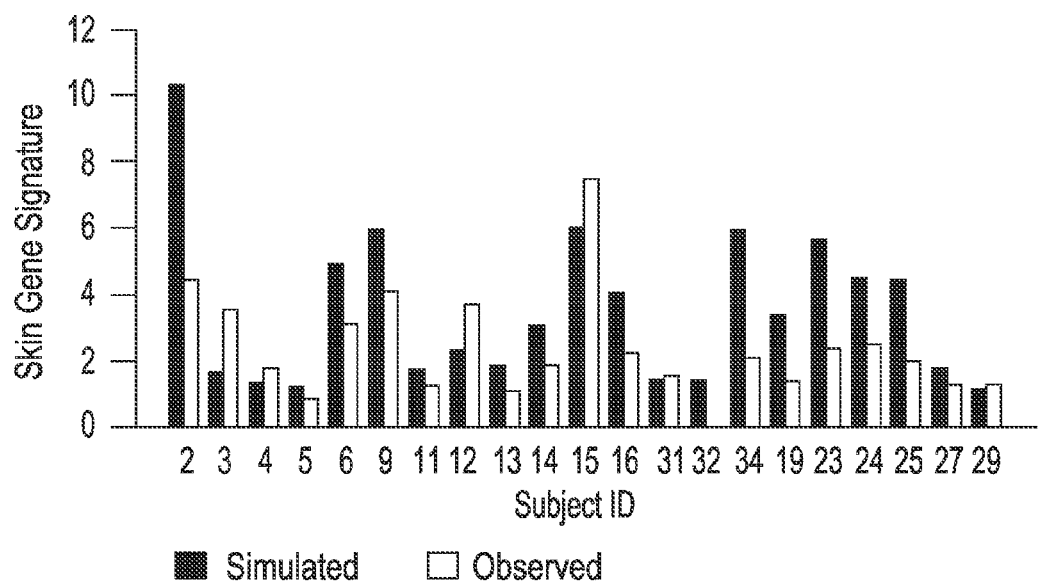
Figure 14B:
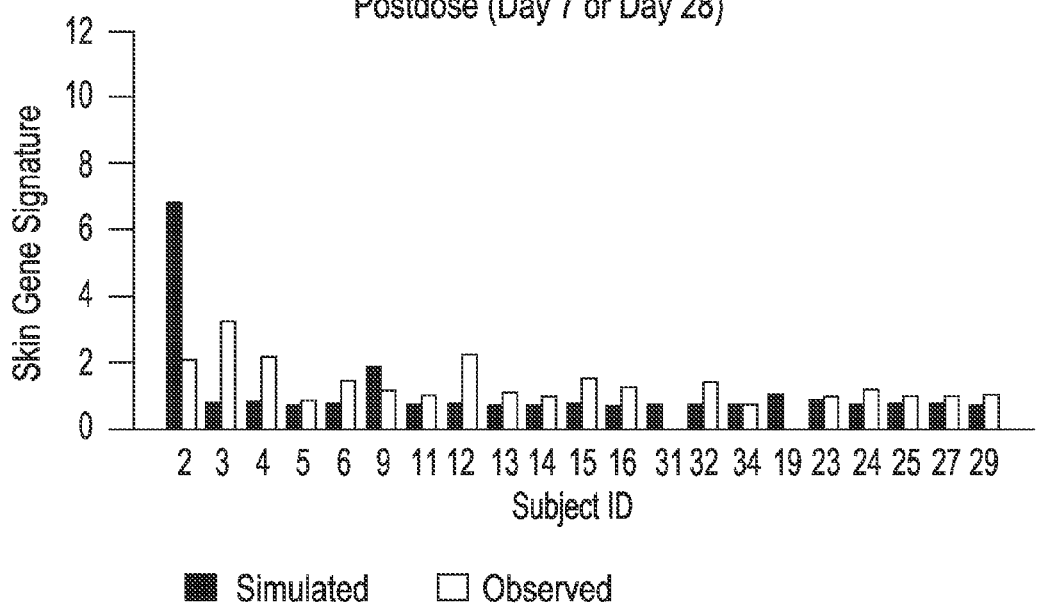

FIG. 14 shows observed and simulated type I IFN GS scores in skin tissues from SSc patients enrolled in the FTIH study for MEDI-546. Baseline (FIG. 14A) and post-dose scores (FIG. 14B) are shown. The skin type I IFN GS data were not modeled (no curve-fitting was performed).

DETAILED DESCRIPTION OF THE INVENTION

The present disclosure provides methods of identifying, diagnosing, treating and monitoring disease progression in patients. MEDI-546 (see U.S. 2011-0059078, herein incorporated by reference in its entirety), a fully human IgG$_1$ kappa monoclonal antibody directed against subunit 1 of IFNAR1 that blocks all type I IFNs, was tested in a first-time-in-human trial (FTIH) in diffuse systemic sclerosis (SSc). A type I IFN Gene Signature (type I IFN GS) shared by systemic lupus erythematous (SLE) and SSc was developed to evaluate the pharmacodynamics, and potentially to predict clinical benefit of MEDI-546.

DEFINITIONS

It must be noted that, as used in this specification and the appended claims, the singular forms "a", "an" and "the" include plural referents unless the context clearly dictates otherwise. The terms "a" (or "an"), as well as the terms "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

It is understood that wherever embodiments are described herein with the language "comprising," otherwise analogous embodiments described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Unless otherwise indicated, amino acid sequences are written left to right in amino to carboxy orientation. The headings provided herein are not limitations of the various aspects or embodiments of the disclosure, which can be had by reference to the specification as a whole. Accordingly, the terms defined immediately below are more fully defined by reference to the specification in its entirety. Amino acids are referred to herein by either their commonly known three letter symbols or by the one-letter symbols recommended by the IUPAC-IUB Biochemical Nomenclature Commission. Nucleotides, likewise, are referred to by their commonly accepted single-letter codes.

As used herein, the term "autoimmune disease" refers to a disorder, disease state or condition associated with the formation of autoantibodies reactive with the patient's own cells to form antigen-antibody complexes. The term "autoimmune disease" includes conditions such as, e.g., systemic lupus erythematosus, as well as those disorders which are triggered by a specific external agent, e.g., acute rheumatic fever. Examples of autoimmune disorders include, but are not limited to, autoimmune hemolytic anemia, autoimmune hepatitis, Berger's disease, chronic fatigue syndrome, Crohn's disease, dermatomyositis, fibromyalgia, Graves' disease, Hashimoto's thyroiditis, idiopathic thrombocytopenia purpura, lichen planus, multiple sclerosis, myasthenia gravis, psoriasis, rheumatic fever, rheumatoid arthritis, scleroderma, Sjogren's syndrome, systemic lupus erythematosus, type 1 diabetes, ulcerative colitis, and vitiligo. In specific aspects, the autoimmune disease is systemic lupus erythematosus (SLE), scleroderma (SSc), myositis, or lupus nephritis.

The terms "Interferon alpha receptor-1," "IFNAR1," and "IFNAR" are used interchangeably, and include variants, isoforms, species homologs of human IFNAR1, and analogs having at least one common epitope with IFNAR1. See, e.g., de Weerd et al., J. Biol. Chem. 282:20053-20057 (2007).

Accordingly, human antibodies specific for human IFNAR1, in certain cases, cross-react with IFNAR1 from species other than human, or other proteins which are structurally related to human IFNAR1 (e.g., human IFNAR1 homologs). In other cases, the antibodies can be completely specific for human IFNAR1 and not exhibit species or other types of cross-reactivity. The complete eDNA sequence of human IFNAR1 has the Genbank accession number NM_000629.

The terms "type I interferon" or "type I IFN" as used herein refer to members of the type I interferon family of molecules that are ligands for IFNAR1 (i.e., members of the type I interferon family of molecules that are capable of binding IFNAR1). Examples of type I interferon ligands are interferon alpha 1, 2a, 2b, 4, 5, 6, 7, S, 10, 14, 16, 17, 21, interferon beta and interferon omega.

The term "type I IFN-mediated disease or disorder" refers to any type I IFN or IFNα inducible disease, disorder, or condition that exhibits a type I IFN PD marker expression profile or gene signature (type I IFN GS). A PD marker expression profile and a gene signature will be understood to be equivalent. These diseases, disorders, or conditions include those with an autoimmune component such as systemic lupus erythematosus (SLE), scleroderma, lupus nephritis, o myositis. A type I IFN-mediated disease or disorder can be treated by administering a small molecule or a biological agent, e.g., an antibody or an antigen binding fragment thereof. If the therapeutic agent is a biological agent, it may be an antibody specific for any subtype(s) of type I IFN or IFNα. For instance, the antibody may be specific for any one of IFNα1, IFNα2, IFNα4, IFNα5, IFNα6, IFNα7, IFNα8, IFNα10, IFNα14, IFNα 17, IFNα21, IFNβ, or IFNω. Alternatively, the antibody may be specific for any two, any three, any four, any five, any six, any seven, any eight, any nine, any ten, any eleven, any twelve type I IFN of IFNα subtypes. If the antibody is specific for more than one type I IFN subtype, the antibody may be specific for IFNα1, IFNα2, IFN α4, IFNα5, IFNα8, IFNα10, and IFNα21; or it may be specific for IFNα1, IFNα2, IFNα4, IFNα5, IFNα8, and IFNα10; or it may be specific for IFNα1, IFNα2, IFNα4, IFNα5, IFNα8, and IFNα21; or it may be specific for IFNα1, IFNα2, IFNα4, IFNα5, IFNα10, and IFNα21. A therapeutic agent that modulates IFNα activity may neutralize IFNα activity. A type I IFN-mediated disease or disorder can also be treated with antibodies specific for a type I IFN receptor, e.g., IFNAR1. In some aspects, anti-IFNAR1 antibodies can cross-react with IFNAR1 from species other than human. In other aspects, the anti-IFNAR1 antibodies can be specific for IFNAR1 only and not exhibit species or other types of cross-reactivity. In some aspects, the anti-IFNAR1 antibodies exhibit reduced binding affinities for FC ligands and have reduced or ablated effector function (ADCC and/or CDC), reduced or ablated binding to Fc ligands, or reduced or ablated toxicities as compared to an unmodified antibody.

The term "MEDI-546" refers to an Fc-modified version of the anti-IFNAR 9D4 antibody described in U.S. Pat. No. 7,662,381. The sequence of MEDI-546 is described in U.S. 2011-0059078. MEDI-546 comprises a combination of three mutations: L234F, L235E, and P331S, wherein the numbering is according to the EU index as set forth in Kabat, introduced into the lower hinge and CH2 domain of human IgG1, which cause a decrease in their binding to human FcγRI (CD64), FcγRIIA (CD32A), FcγRIII (CD16) and C1q. See, e.g., US 2011/0059078 and Oganesyan et al. Acta Crystallographica D 64:700-704 (2008), which are hereby incorporated by reference in their entireties. The VH and Vk sequences of MEDI-546 are shown in TABLE 1.

TABLE 1

| | |
|---|---|
| MEDI-546 VH (SEQ ID NO: 1) | EVQLVQSGAEVKKPGESLKISCKGSGYIFTNYWIAWVRQMPGKCLESMGI IYPGDSDIRYSPSFQGQVTISADKSITTAYLQWSSLKASDTAMYYCARHD IEGFDYWGRGTLVTVSS |
| MEDI-546 VK (SEQ ID NO: 2) | EIVLTQSPGTLSLSPGERATLSCRASQSVSSSFFAWYQQKPGQAPRLLIY GASSRATGIPDRLSGSGSGTDFTLTITRLEPEDFAVYYCQQYDSSAITFG QGTRLEIK |

The term "antibody or antigen-binding fragment thereof that modulates type I IFN activity" refers to an antibody (see infra) in its broadest sense capable of modulating type I IFN activity in a patient. The term "modulating" as used herein includes the inhibition or suppression of a type I IFN activity as well as the induction or enhancement of a type I IFN activity. In specific aspects, the type I IFN activity is IFNα activity. In some aspects, the suppression of a type IFN GS is a suppression of a type I IFN activity. In some aspects, the antibody or antigen-binding fragment thereof is monoclonal. In specific aspects, the antibody or antigen-binding fragment thereof that modulates type I IFN activity specifically binds to a type I IFN receptor such as IFNAR1. In some specific aspects, the antibody or antigen-binding fragment thereof specifically binds to subunit 1 of IFNAR1.

The term "antibody" is used herein in its broadest sense and includes, e.g., monoclonal antibodies, polyclonal antibodies, multivalent antibodies, multispecific antibodies, chimeric antibodies, and humanized antibodies. The term "antibody" includes whole antibodies. The term "antibody" also refers to a protein comprising at least two immunoglobulin heavy (H) chains and two immunoglobulin light (L) chains inter-connected by disulfide bonds, or an antigen binding portion thereof. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system.

The term "antigen-binding fragment" refers to one or more fragments of an antibody that retain the ability to specifically bind to an antigen (e.g., IFNAR). It has been shown that the antigen-binding function of an antibody can be performed by fragments of a full-length antibody. Examples of binding fragments encompassed within the term "antigen-binding fragment" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding fragment" of an antibody. These antibody fragments are obtained using conventional techniques known to those with skill in the art, and the fragments are screened for utility in the same manner as are intact antibodies.

An "isolated antibody," as used herein, is intended to refer to an antibody that is substantially free of other antibodies having different antigenic specificities (e.g., an isolated antibody that specifically binds IFNAR is substantially free of antibodies that specifically bind antigens other than IFNAR). An isolated antibody that specifically binds IFNAR can, however, have cross-reactivity to other antigens, such as IFNAR molecules from other species. Moreover, an isolated antibody can be substantially free of other cellular material and/or chemicals.

The term "monoclonal antibody" as used herein refer to a preparation of antibody molecules of single molecular composition. A monoclonal antibody displays a single binding specificity and affinity for a particular epitope.

The term "human antibody", as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the disclosure can include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "human monoclonal antibody" refers to antibodies displaying a single binding specificity which have variable regions in which both the framework and CDR regions are derived from human germline immunoglobulin sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

The term "recombinant human antibody", as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The term "antibody" as used herein also includes "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al, *Proc. Natl. Acad. Sci. USA* 81:6851-6855 (1984)).

Basic antibody structures in vertebrate systems are relatively well understood. See, e.g., Harlow et al. (1988) Antibodies: A Laboratory Manual (2nd ed.; Cold Spring Harbor Laboratory Press).

In the case where there are two or more definitions of a term that is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al. (1983) U.S. Dept. of Health and Human Services, "Sequences of Proteins of Immunological Interest" and by Chothia and Lesk, *J. Mol. Biol.* 196:901-917 (1987), which are incorporated herein by reference, where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues that encompass the CDRs as defined by each of the above cited references are set forth below in TABLE 2 as a comparison. The exact residue numbers that encompass a particular CDR will vary depending on the sequence and size of the CDR. Those skilled in the art can routinely determine which residues comprise a particular CDR given the variable region amino acid sequence of the antibody.

TABLE 2

CDR Definitions[1]

|         | Kabat  | Chothia |
|---------|--------|---------|
| VH CDR1 | 31-35  | 26-32   |
| VH CDR2 | 50-65  | 52-58   |
| VH CDR3 | 95-102 | 95-102  |
| VL CDR1 | 24-34  | 26-32   |
| VL CDR2 | 50-56  | 50-52   |
| VL CDR3 | 89-97  | 91-96   |

[1]Numbering of all CDR definitions in Table 1 is according to the numbering conventions set forth by Kabat et al. (see below).

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al. (1983) U.S. Dept. of Health and Human Services, "Sequence of Proteins of Immunological Interest." Unless otherwise specified, references to the numbering of specific amino acid residue positions in an anti-IFNAR antibody or antigen-binding fragment, variant, or derivative thereof of the present disclosure are according to the Kabat numbering system.

As used herein, the terms "treat" or "treatment" refer to both therapeutic treatment and prophylactic or preventative measures, wherein the object is to prevent or slow down (lessen) an undesired physiological change or disorder, such as the progression of an autoimmune condition, e.g., a rheumatic condition. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The terms "effective amount" or "amount effective to" or "therapeutically effective amount" includes reference to a dosage of a therapeutic agent sufficient to produce a desired result.

By "subject" or "patient" is meant any subject, particularly a mammalian subject, for whom diagnosis, prognosis, or therapy is desired. As used herein, the terms "subject" or "patient" include any human or nonhuman animal. The term "nonhuman animal" includes all vertebrates, e.g., mammals and non-mammals, such as nonhuman primates, sheep, dogs, cats, horses, cows, bears, chickens, amphibians, reptiles, etc. As used herein, phrases such as "a patient having a type I IFN-mediated disease or disorder" includes subjects, such as mammalian subjects, that would benefit from the administration of an antibody or antigen-binding fragment thereof that modulates type I IFN activity, e.g., for detection, imaging, or other diagnostic procedure, and/or from treatment, i.e., palliation or prevention of a disease, with such antibody or antigen-binding fragment thereof.

Terms such as "treating" or "treatment" or "to treat" refer to both (1) therapeutic measures that cure, slow down, lessen symptoms of, and/or halt progression of a diagnosed pathologic condition or disorder and (2) prophylactic or preventative measures that prevent and/or slow the development of a targeted pathologic condition or disorder. Thus, those in need of treatment include those already with the disorder; those prone to have the disorder; and those in whom the disorder is to be prevented.

Pharmacokinetic Model and Translational Application

In a Phase 1 trial (MI-CP180; ClinicalTrials.gov Identifier: NCT00930683) treatment with MEDI-546 resulted in complete neutralization of the type I IFN GS in peripheral blood and skin biopsies from SSc patients in a dose-dependent manner. To our knowledge, this is the first study demonstrating normalization of the type I IFN GS in the peripheral blood and disease tissue where type I IFN is involved in the pathogenesis of the disease.

To rapidly bridge clinical indications to SLE for a Phase 2 trial, a translational model was developed that incorporated (1) the pharmacokinetics (PK) and pharmacodynamics (PD) of MEDI-546 in SSc patients, (2) the internalization kinetics of the MEDI-546/IFNAR complex as determined from confocal imaging studies, and (3) the magnitude of differences in the type I IFN GS in blood and skin between SSc and SLE patients. This model was first used to characterize the disposition properties of MEDI-546 and the suppression of the type I IFN signature in SSc patients, for which clinical data was available. Afterwards, the PK/PD model was adjusted to account for the magnitude of differences in the type I IFN GS between SSc and SLE patients, and stochastic PK-PD simulations were performed to predict type I IFN GS responses in blood and skin specimens upon multiple MEDI-546 administrations in virtual SLE patients. This approach facilitated a rapid progression of MEDI-546 clinical development and the optimal design of a Phase 2 study in SLE. Stochastic simulations predicted that once-every-four-week intravenous administrations of MEDI-546 at 100 mg, 300 mg or 1000 mg fixed doses could suppress the type I IFN GS in the blood of SLE patients to the level of healthy normal subjects (mean±2 standard).

Thus, the present disclosure provides a pharmacokinetic/pharmacodynamic (PK/PD) stochastic model for type I IFN-mediated diseases or disorders. In some aspects, the PK/PD stochastic model comprises two compartments. These two compartments can be a central compartment and a peripheral compartment. In certain aspects, the PK/PD stochastic model can comprises additional compartments, e.g., a skin compartment. The PK/PD stochastic model comprises can also comprise at least one elimination pathway. In some aspects, the PK/PD stochastic model comprises two elimination pathways. In some aspects, the two elimination pathways are a clearance pathway and a target-mediated disposition pathway. In some aspects, the clearance pathway in the PK/PD stochastic model is a reticuloendothelial system pathway.

The PK/PD stochastic model can be used, for example for translational purposes. In this respect, PK/PD data corresponding a first type I IFN-mediated disease or disorder can be used to generate the PK/PD stochastic model, and then the PK/PD stochastic model can be adjusted using inputted PK/PD data from the second type I IFN-mediated disease or disorder. This adjusted model can be used in turn to conduct simulation and infer information corresponding to the second type I IFN-mediated disease or disorder such as determining optimal dosage regimens, determining whether a candidate therapeutic agent should be selected to treat a patient, select a candidate patient for therapy, or design a personalized therapy. In some aspects, the adjusted model can be used, for example, to select candidate subjects for a clinical study.

The PK/PD data for the first or second type I IFN-mediated disease or disorder can comprise binding affinity data. For example, the binding affinity data can correspond to the binding of an antibody or antigen binding fragment thereof to a type I IFN receptor. In some aspects, the antibody or antigen binding fragment thereof is MEDI-546. In some aspects, the type I IFN receptor is IFNAR1.

In some aspects, the first type I IFN-mediated disease or disorder is SSc and the second type I IFN-mediated disease or disorder is SLE. In some other aspects, the first type I IFN-mediated disease or disorder SSc and the second type I IFN-mediated disease or disorder is myositis. In some aspects, the first type I IFN-mediated disease or disorder is SSc and the second type I IFN-mediated disease or disorder is lupus nephritis. In general, the first and second type I IFN-mediated diseases or disorders can be rheumatic diseases. One skilled in the art will appreciate that other pairs of type I IFN-mediated related diseases or disorders can be used.

In some aspects, the PK/PD data corresponding the first or second type I IFN-mediated disease or disorder comprise kinetics data, e.g., internalization kinetics of an antigen-antibody complex by cells. In some aspects, the antigen is IFNAR1. In other aspects, the antibody is MEDI-546. In some aspects, the cells are THP-1 cells. One skilled in the art would appreciate that different antibodies, antigens, and cell lines can be used.

In some aspects, the PK/PD data corresponding to the first or second type I IFN-mediated disease or disorder comprise type I IFN GS suppression data (e.g., full suppression or partial suppression). In some aspects, the type I IFN GS comprises up-regulated expression or activity of genes IF127, IF144, IF144L, and RSAD2. In some aspects, the type I IFN GS further comprises IF16. One skilled in the art would appreciate that other type I IFN GS can be used, as discussed below.

Fixed Dose Administration

The present disclosure provides a method of treating a patient having a type I IFN-mediated disease or disorder comprising administering a fixed dose of an antibody or antibody fragment thereof that modulates type I IFN activity, wherein the dose is effective to treat the disorder. In some aspects, the antibody is an anti IFNAR antibody. In some specific aspects, the antibody is an anti-IFNAR1 antibody, e.g., MEDI-546.

A "fixed dose" as used herein refers to a dose that is administered to a patient without regard for the weight (WT) or body surface area (BSA) of the patient. The fixed dose of antibody or antibody fragment thereof that modulates type I IFN activity, e.g., MEDI-546, is therefore not provided as a mg/kg dose or mg/m2 dose, but rather as an absolute amount of the therapeutic agent.

In some aspects, an antibody or antibody fragment thereof that modulates type I IFN activity is administered as a fixed dose ranging from about 100 mg to about 1000 mg. In other aspects, the fixed dose is from about 300 mg to about 1000 mg. In some aspects, the fixed dose is lower than about 300 mg. In some specific aspects, the antibody or antibody fragment thereof that modulates type I IFN activity is MEDI-546.

In some aspects, an antibody or antibody fragment thereof that modulates type I IFN activity is administered at a fixed dose of about 10 mg, or about 20 mg, or about 30 mg, or about 40 mg, or about 50 mg, or about 60 mg, or about 70 mg, or about 80 mg, or about 90 mg, or about 100 mg. In other aspects, an antibody or antibody fragment thereof that modulates type I IFN activity is administered at a fixed dose of about 100 mg, or about 150 mg, about 200 mg, or about 300 mg, or about 400 mg, or about 500 mg, or about 600 mg, or about 700 mg, or about 800 mg, or about 900 mg, or about 1000 mg, or about 1100 mg, or about 1200 mg, or about 1300 mg, or about 1400 mg, or about 1500 mg, or about 1600 mg, or about 1700 mg, or about 1800 mg, or about 1900 mg, or about 2000 mg. In certain aspects, the fixed dose is about 100 mg. In other specific aspects, the fixed dose is about 300 mg. In yet another aspect, the fixed dose is about 1000 mg.

In some aspects, the antibody or antibody fragment thereof that modulates type I IFN activity can be administered intravenously, intramuscularly, subcutaneously, or a combination thereof. The antibody or antibody fragment thereof that modulates type I IFN activity can also be administered by any means known in the art. In specific aspects, the antibody or antibody fragment thereof that modulates type I IFN activity is administered intravenously at a fixed dosage about 100 mg, or about 300 mg, or about 1000 mg. In a specific aspect, the antibody or antibody fragment thereof that modulates type I IFN activity is administered subcutaneously at a fixed dosage of about 100 mg, or about 300 mg, or about 1000 mg.

In some aspects, a loading dose of the antibody or antibody fragment thereof that modulates type I IFN activity is administered. In a specific aspect, the antibody or antibody fragment thereof that modulates type I IFN activity is administered intravenously at a fixed dosage about 100 mg, or about 300 mg, or about 1000 mg once per month. In some aspects, the antibody or antibody fragment thereof that modulates type I IFN activity can be administered subcutaneously.

When a series of fixed doses of an antibody or antibody fragment thereof that modulates type I IFN activity are administered, these doses can, for example, be administered approximately every week, approximately every 2 weeks, approximately every 3, or about every 4 weeks. In some aspects, fixed doses of an antibody or antibody fragment thereof that modulates type I IFN activity are administered approximately every day, approximately every two days, approximately every three days, approximately every 4 days, approximately every 5 days, approximately every 6 days, or approximately every seven days.

In a specific aspect, the fixed dose of antibody or antibody fragment thereof that modulates type I IFN activity is a 100 mg dose administered monthly. In another specific aspect, the fixed dose of antibody or antibody fragment thereof that modulates type I IFN activity is a 300 mg dose administered monthly. In a specific aspect, the fixed dose of antibody or antibody fragment thereof that modulates type I IFN activity is a 1000 mg dose administered monthly. In specific aspects, the fixed dose of antibody or antibody fragment thereof that modulates type I IFN activity is a 100 mg, 300 mg, or 1000 mg monthly dose of MEDI-546.

In specific aspects, fixed doses of antibody or antibody fragment thereof that modulates type I IFN activity can be administered every month. Successive doses can be administered in successive months. These fixed doses can be administered, for example, for about 1 month, or about 2 months, or about 3 months, or about 4 months, or about 5 months, or about 6 months. Such fixed doses can, for example, continue to be administered until disease progression, adverse event, or other parameter occurs as determined by a healthcare provider, e.g., suppression or lack of suppression of a type I IFN GS.

In some embodiments, patients can be administered at least one, at least 2, at least 3, at least 4, at least 5, at least 6, at least 7, at least 8, at least 9, at least 10, at least 11, at least 12, at least 13, at least 14 or at least 15 fixed doses of antibody or antibody fragment thereof that modulates type I IFN activity. In some aspects, fixed doses of antibody or antibody fragment thereof that modulates type I IFN activity are administered at equal time intervals. In other embodiment, fixed doses of antibody or antibody fragment thereof that modulates type I IFN activity are administered at varying intervals. In some aspects, all administered fixed doses are essentially identical. In other aspects, at least one fixed dose is different with respect to the other doses, e.g., in volume, concentration, route of administration, formulation, etc.

For the prevention or treatment of autoimmune diseases, e.g., SLE, SSc, myositis, or lupus nephritis the fixed dose of antibody or antibody fragment thereof that modulates type I IFN activity, e.g., MEDI-546, will depend, for example, on the type of disease to be treated, as defined above, the severity and course of the disease, whether the antibody is administered for preventive or therapeutic purposes, previous therapy, the patient's clinical history and response to the antibody, and the discretion of the attending physician.

In a specific embodiment, the disclosure provides a method of treating a type I IFN-mediated disease or disorder, such as an autoimmune disorder (e.g., SLE, SSc, lupus nephritis, myositis) in a patient comprising administering at least one intravenous or subcutaneous fixed dose of an anti-IFNAR antibody such as MEDI-546 to the patient, wherein the fixed dose is about 100 mg, about 300 mg, or about 1000 mg.

Type I Interferon Gene Signature (IFN GS)

The present disclosure also provides a type I Interferon Gene Signature (type I IFN GS) that can be specifically suppressed when a patient suffering from a type I IFN-mediated disease or disorder is treated with a fixed dose of an antibody or antigen-binding fragment thereof that modulates type I IFN activity.

In one aspect, the type I IFN GS that can be suppressed with a fixed dose of an antibody or antigen-binding fragment thereof that modulates type I IFN activity is a subset of the 21 genes used as pharmacodynamics (PD) markers for sifalimumab, an anti-IFN-α monoclonal therapy in SLE described previously (Yao et al., Arthritis Rheum. 60:1785-1796 (2009); Yao et al., Hum. Genomics Proteomics 2009: 374312 (2009); Yao et al., Arthritis Res. Ther. 12 (Suppl 1):S6 (2010)).

In some aspects, these 21 genes (see TABLE 3) are: IF127 (interferon alpha inducible protein 27) (SEQ ID NO:3), IF144 (interferon-induced protein 44) (SEQ ID NO:4), IF144L (interferon induced protein 44, like) (SEQ ID NO:5), RSAD2 (radical S-adenosyl methionine domain containing 2) (SEQ ID NO:6), IFI6 (interferon, alpha inducible protein 6) (SEQ ID NO:7), MX1 (myxovirus (influenza virus) resistance 1, interferon-inducible protein p78) (SEQ ID NO:8), IFIT1 (interferon-induced protein with tetratricopeptide repeats 1) (SEQ ID NO:9), HERC5 (hect domain and RLD 5) (SEQ ID NO:10), ISG15 (ISG15 ubiquitin-like modifier) (SEQ ID NO:11), LAMP3 (lysosomal-associated membrane protein 3) (SEQ ID NO:12), OAS3 (2'-5'-oligoadenylate synthetase 3, 100 kDa) (SEQ ID NO:13), OAS1 (2'-5'-oligoadenylate synthetase 1, 40/60 kDa) (SEQ ID NO:14), EPST1 (epithelial stromal interaction 1 (breast)) (SEQ ID NO:15), IFIT3 (interferon-induced protein with tetratricopeptide repeats 3) (SEQ ID NO:16), LY6E (lymphocyte antigen 6 complex, locus E) (SEQ ID NO:17), OAS2 (2'-5'-oligoadenylate synthetase 2, 69/71 kDa) (SEQ ID NO:18), PLSCR1 (phospholipid scramblase 1) (SEQ ID NO:19), SIGLEC1 (sialic acid binding Ig-like lectin 1, sialoadhesin) (SEQ ID NO:20), USP18 (ubiquitin specific peptidase 18) (SEQ ID NO:21), RTP4 (receptor (chemosensory) transporter protein 4) (SEQ ID NO:22), and DNAPTP6 (DNA polymerase-transactivated protein 6) (SEQ ID NO:23). See PCT Publ. No. WO 2008/070137, which is incorporated herein by reference in its entirety.

TABLE 3

<table>
<tr><td>IF127<br>(SEQ ID NO: 3)</td><td>sp|P40305|IFI27_HUMAN<br>Interferon alpha-<br>inducible protein 27</td><td>MEASALTSSAVTSVAKVVRVASGSAVVLPLARIATVVIGGVVA<br>VPMVLSAMGFTAAGIASSSIAAKMMSAAAIANGGGVASGS<br>LVATLQSLGATGLSGLTKFILGSIGSAIAAVIARFY</td></tr>
<tr><td>IF144<br>(SEQ ID NO: 4)</td><td>sp|Q8TCB0|IFI44_HUMAN<br>Interferon-induced<br>protein 44</td><td>MAVTTRLTWLHEKILQNHFGGKRLSLLYKGSVHGFRNGVLLDR<br>CCNQGPTLTVIYSEDHIIGAYAEESYQEGKYASIILFALQ<br>DTKISEWKLGLCTPETLFCCDVTKYNSPTNFQIDGRNRKV<br>IMDLKTMENLGLAQNCTISIQDYEVFRCEDSLDERKIKGV<br>IELRKSLLSALRTYEPYGSLVQQIRILLLGPIGAGKSSFF<br>NSVRSVFQGHVTHQALVGTNTTGISEKYRTYSIRDGKDGK<br>YLPFILCDSLGLSEKEGGLCRDDIFYILNGNIRDRYQFNP<br>MESIKLNHHDYIDSPSLKDRIHCVAFVFDASSIQYFSSQM<br>IVKIKRIRRELVNAGVVHVALLTHVDSMDLITKGDLIEIE<br>RCEPVRSKLEEVQRKLGFALSDISVVSNYSSEWELDPVKD<br>VLILSALRRMLWAADDFLEDLPFEQIGNLREEIINCAQGK<br>K</td></tr>
<tr><td>IFI44L<br>(SEQ ID NO: 5)</td><td>sp|Q53G44|IF44L_HUMAN<br>Interferon-induced<br>protein 44-like</td><td>MEVTTRLTWNDENHLRKLLGNVSLSLLYKSSVHGGSIEDMVER<br>CSRQGCTITMAYIDYNMIVAFMLGNYINLHESSTEPNDSL<br>WFSLQKKNDTTEIETLLLNTAPKIIDEQLVCRLSKTDIFI<br>ICRDNKIYLDKMITRNLKLRFYGHRQYLECEVFRVEGIKD<br>NLDDIKRIIKAREHRNRLLADIRDYRPYADLVSEIRILLV<br>GPVGSGKSSFFNSVKSIFHGHVTGQAVVGSDITSITERYR<br>IYSVKDGKNGKSLPFMLCDTMGLDGAEGAGLCMDDIPHIL<br>KGCMPDRYQFNSRKPITPEHSTFITSPSLKDRIHCVAYVL<br>DINSIDNLYSKMLAKVKQVHKEVLNCGIAYVALLTKVDDC<br>SEVLQDNFLNMSRSMTSQSRVMNVHKMLGIPISNILMVGN<br>YASDLELDPMKDILILSALRQMLRAADDFLEDLPLEETGA<br>IERALQPCI</td></tr>
</table>

TABLE 3-continued

| Gene | Accession | Description | Sequence |
|---|---|---|---|
| RSAD2 (SEQ ID NO: 6) | sp\|Q8WXG1\|RSAD2_HUMAN | Radical S-adenosyl methionine domain-containing protein 2 | MWVLTPAAFAGKLLSVFRQPLSSLWRSLVPLFCWLRATFWLLA TKRRKQQLVLRGPDETKEEEEDPPLPTTPTSVNYHFTRQC NYKCGFCFHTAKTSFVLPLEEAKRGLLLLKEAGMEKINFS GGEPFLQDRGEYLGKLVRFCKVELRLPSVSIVSNGSLIRE RWFQNYGEYLDILAISCDSFDEEVNVLIGRGQGKKNHVEN LQKLRRWCRDYRVAFKINSVINRFNVEEDMTEQIKALNPV RWKVFQCLLIEGENCGEDALREAERFVIGDEEFERFLERH KEVSCLVPESNQKMKDSYLILDEYMRFLNCRKGRKDPSKS ILDVGVEEAIKFSGFDEKMFLKRGGKYIWSKADLKLDW |
| IFI6 (SEQ ID NO: 7) | sp\|P09912\|IFI6_HUMAN | Interferon alpha-inducible protein 6 | MRQKAVSLFLCYLLLFTCSGVEAGKKKCSESSDSGSGFWKALT FMAVGGGLAVAGLPALGFTGAGIAANSVAASLMSWSAILN GGGVPAGGLVATLQSLGAGGSSVVIGNIGALMGYATHKYL DSEEDEE |
| MX1 (SEQ ID NO: 8) | gi\|295842578\|ref\|NP_001171517.1\| | interferon-induced GTP-binding protein Mx1 [Homo sapiens] | MVVSEVDIAKADPAAASHPLLLNGDATVAQKNPGSVAENNLCS QYEEKVRPCIDLIDSLRALGVEQDLAL PAIAVIGDQSSGKSSVLEALSGVALPRGSGIVTRCPLVLKLKK LVNEDKWRGKVSYQDYEIEISDASEVE KEINKAQNAIAGEGMGISHELITLEISSRDVPDLTLIDLPGIT RVAVGNQPADIGYKIKTLIKKYIQRQE TISLVVVPSNVDIATTEALSMAQEVDPEGDRTIGILTKPDLVD KGTEDKVVDVVRNLVFHLKKGYMIVKC RGQQEIQDQLSLSEALQREKIFFENHPYFRDLLEEGKATVPCL AEKLTSELITHICKSLPLLENQIKETH QRITEELQKYGVDIPEDENEKMFFLIDKVNAFNQDITALMQGE ETVGEEDIRLFTRLRHEFHKWSTIIEN NFQEGHKILSRKIQKFENQYRGRELPGFVNYRTFETIVKQQIK ALEEPAVDMLHTVTDMVRLAFTDVSIK NFEEFFNLHRTAKSKIEDIRAEQEREGEKLIRLHFQMEQIVYC QDQVYRGALQKVREKELEEEKKKKSWD FGAFQSSSATDSSMEEIFQHLMAYHQEASKRISSHIPLIIQFF MLQTYGQQLQKAMLQLLQDKDTYSWLL KERSDTSDKRKFLKERLARLTQARRRLAQFPG |
| IFIT1 (SEQ ID NO: 9) | gi\|116534937\|ref\|NP_001539.3\| | interferon-induced protein with tetratricopeptide repeats 1 [Homo sapiens] | MSTNGDDHQVKDSLEQLRCHFTWELSIDDDEMPDLENRVLDQI EFLDTKYSVGIHNLLAYVKHLKGQNEE ALKSLKEAENLMQEEHDNQANVRSLVTWGNFAWMYYHMGRLAE AQTYLDKVENICKKLSNPFRYRMECPE IDCEEGWALLKCGGKNYERAKACFEKVLEVDPENPESSAGYAI SAYRLDGFKLATKNHKPFSLLPRQAV RLNPDNGYIKVLLALKLQDEGQEAEGEKYIEEALANMSSQTYV FRYAAKFYRRKGSVDKALELLKKALQE TPTSVLLHHQIGLCYKAQMIQIKEATKGQPRGQNREKLDKMIR SAIFHFESAVEKKPTFEVAHLDLARMY IEAGNHRKAEENFQKLLCMKPVVEETMQDIHFHYGRFQEFQKK SDVNAIIHYLKAIKIEQASLTRDKSIN SLKKLVLRKLRRKALDLESLSLLGFVYKLEGNMNEALEYYERA LRLAADFENSVRQGP |
| HERC5 (SEQ ID NO: 10) | gi\|110825982\|ref\|NP_057407.2\| | E3 ISG15--protein ligase HERC5 [Homo sapiens] | MERRSRRKSRRNGRSTAGKAAATQPAKSPGAQLWLFPSAAGLH RALLRRVEVTRQLCCSPGRLAVLERGG AGVQVHQLLAGSGGARTPKCIKLGKNMKIHSVDQGAEHMLILS SDGKPFEYDNYSMKHLRFESILQEKKI IQITCGDYHSLALSKGGELFAWGQNLHGQLGVGRKFPSTTTPQ IVEHLAGVPLAQISAGEAHSMALSMSG NIYSWGKNECGQLGLGHTESKDDPSLIEGLDNQKVEFVACGGS HSALLTQDGLLFTFGAGKHGQLGHNST QNELRPCLVAELVGYRVTQIACGRWHTLAYVSDLGKVFSFGSG KDGQLGNGGTRDQLMPLPVKVSSSEEL KLESHTSEKELIMIAGGNQSILLWIKKENSYVNLKRTIPTLNE GTVKRWIADVETKRWQSTKREIQEIFS SPACLTGSFLRKRRTTEMMPVYLDLNKARNIFKELTQKDWITN MITTCLKDNLLKRLPFHSPPQEALEIF FLLPECPMMHISNNWESLVVPFAKVVCKMSDQSSLVLEEYWAT LQESTFSKLVQMFKTAVICQLDYWDES AEENGNVQALLEMLKKLHRVNQVKCQLPESIFQVDELLHRLNF FVEVCRRYLWKMTVDASENVQCCVIFS HPPPIFNNLSKIKLLHTDTLLKIESKKHKAYLRSAAIEEERES EFALRPTFDLTVRRNHLIEDVLNQLSQ FENEDLRKELWVSFSGEIGYDLGGVKKEFFYCLFAEMIQPEYG MFMYPEGASCMWFPVKPKFEKKRYFFF GVLCGLSLFNCNVANLPFPLALFKKLLDQMPSLEDLKELSPDL GKNLQTLLDDEGDNFEEVFYIHFNVHW DRNDTNLIPNGSSITVNQTNKRDYVSKYINYIFNDSVKAVYEE FRRGFYKMCDEDIIKLFHPEELKDVIV GNTDYDWKTFEKNARYEPGYNSSHPTIVMFWKAFHKLTLEEKK KFLVFLTGTDRLQMKDLNNMKITFCCP ESWNERDPIRALTCFSVLFLPKYSTMETVEEALQEAINNNRGF G |

TABLE 3-continued

| | | |
|---|---|---|
| ISG15 (SEQ ID NO: 11) | gi\|4826774\|ref\|NP_005092.1\| ubiquitin-like protein ISG15 precursor [Homo sapiens] | MGWDLTVKMLAGNEFQVSLSSSMSVSELKAQITQKIGVHAFQQ RLAVHPSGVALQDRVPLASQGLGPGST VLLVVDKCDEPLSILVRNNKGRSSTYEVRLTQTVAHLKQQVSG LEGVQDDLFWLTFEGKPLEDQLPLGEY GLKPLSTVFMNLRLRGGGTEPGGRS |
| LAMP3 (SEQ ID NO: 12) | gi\|38455385\|ref\|NP_055213.2\| lysosome-associated membrane glycoprotein 3 precursor [Homo sapiens] | MPRQLSAAAALFASLAVILHDGSQMRAKAFPETRDYSQPTAAA TVQDIKKPVQQPAKQAPHQTLAARFMD GHITFQTAATVKIPTTTPATTKNTATTSPITYTLVTTQATPNN SHTAPPVTEVTVGPSLAPYSLPPTITP PAHTTGTSSSTVSHTTGNTTQPSNQTTLPATLSIALHKSTTGQ KPVQPTHAPGTTAAAHNTTRTAAPAST VPGPTLAPQPSSVKTGIYQVLNGSRLCIKAEMGIQLIVQDKES VFSPRRYFNIDPNATQASGNCGTRKSN LLLNFQGGFVNLTFTKDEESYYISEVGAYLTVSDPETIYQGIK HAVVMFQTAVGHSFKCVSEQSLQLSAH LQVKTTDVQLQAFDFEDDHFGNVDECSSDYTIVLPVIGAIVVG LCLMGMGVYKIRLRCQSSGYQRI |
| OAS3 (SEQ ID NO: 13) | gi\|45007007\|ref\|NP_006178.2\| 2'-5'-oligoadenylate synthase 3 [Homo sapiens] | MDLYSTPAAALDRFVARRLQPRKEFVEKARRALGALAAALRER GGRLGAAAPRVLKTVKGGSSGRGTALK GGCDSELVIFLDCFKSYVDQRARRAEILSEMRASLESWWQNPV PGLRLTFPEQSVPGALQFRLTSVDLED WMDVSLVPAFNVLGQAGSGVKPKPQVYSTLLNSGCQGGEHAAC FTELRRNFVNIRPAKLKNLILLVKHWY HQVCLQGLWKETLPPVYALELLTIFAWEQGCKKDAFSLAEGLR TVLGLIQQHQHLCVFWTVNYGFEDPAV GQFLQRQLKRPRPVILDPADPTWDLGNGAAWHWDLLAQEAASC YDHPCFLRGMGDPVQSWKGPGLPRAGC SGLGHPIQLDPNQKTPENSKSLNAVYPRAGSKPPSCPAPGPTG AASIVPSVPGMALDLSQIPTKELDRFI QDHLKPSPQFQEQVKKAIDIILRCLHENCVHKASRVSKGGSFG RGTDLRDGCDVELIIFLNCFTDYKDQG PRRAEILDEMRAQLESWWQDQVPSLSLQFPEQNVPEALQFQLV STALKSWTDVSLLPAFDAVGQLSSGTK PNPQVYSRLLTSGCQEGEHKACFAELRRNFMNIRPVKLKNLIL LVKHWYRQVAAQNKGKGPAPASLPPAY ALELLLTIFAWEQGCRQDCFNMAQGFRTVLGLVQQHQQLCVYWT VNYSTEDPAMRMHLLGQLRKPRPLVLD PADPTWNVGHGSWELLAQEAAALGMQACFLSRDGTSVQPWDVM PALLYQTPAGDLDKFISEFLQPNRQFL AQVNKAVDTICSFLKENCFRNSPIKVIKVVKGGSSAKGTALRG RSDADLVVFLSCFSQFTEQGNKRAEII SEIRAQLEACQQERQFEVKFEVSKWENPRVLSFSLTSQTMLDQ SVDFDVLPAFDALGQLVSGSRPSSQVY VDLIHSYSNAGEYSTCFTELQRDFIISRPTKLKSLIRLVKHWY QQCTKISKGRGSLPPQHGLELLTVYAW EQGGKDSQFMNAEGFRTVLELVTQYRQLCIYWTINYNAKDKTV GDFLKQQLQKPRPIILDPADPTGNLGH NARWDLLAKEAAACTSALCCMGRNGIPIQPWPVKAAV |
| OAS1 (SEQ ID NO: 14) | gi\|74229013\|ref\|NP_058132.2\| 2'-5'-oligoadenylate synthase 1 isoform 1 [Homo sapiens] | MMDLRNTPAKSLDKFIEDYLLPDTCFRMQINHAIDIICGFLKE RCFRGSSYPVCVSKVVKGGSSGKGTTL RGRSDADLVVFLSPLTTFQDQLNRRGEFIQEIRRQLEACQRER AFSVKFEVQAPRWGNPRALSFVLSSLQ LGEGVEFDVLPAFDALGQLTGGYKPNPQIYVKLIEECTDLQKE GEFSTCFTELQRDFLKQRPTKLKSLIR LVKHWYQNCKKKLGKLPPQYALELLTVYAWERGSMKTHFNTAQ GFRTVLELVINYQQLCIYWTKYYDFKN PIIEKYLRRQLTKPRPVILDPADPTGNLGGGDPKGWRQLAQEA EAWLNYPCFKNWDGSPVSSWILLAESN SADDETDDPRRYQKYGYIGTHEYPHFSHRPSTLQAASTPQAEE DWTCTIL |
| EPSTI1 (SEQ ID NO: 15) | gi\|50428917\|ref\|NP_001002264.1\| epithelial-stromal interaction protein 1 isoform 1 [Homo sapiens] | MNTRNRVVNSGLGASPASRPTRDPQDPSGRQGELSPVEDQREG LEAAPKGPSRESVVHAGQRRTSAYTLI APNINRRNEIQRIAEQELANLEKWKEQNRAKPVHLVPRRLGGS QSETEVRQKQQLQLMQSKYKQKLKREE SVRIKKEAEEEAELQKMKAIQREKSNKLEEKKRLQENLRREAFR EHQQYKTAEFLSKLNTESPDRSACQSA VCGPQSSTWKLPILPRDHSWARSWAYRDSLKAEENRKLQKMKD EQHQKSELLELKRQQQEQERAKIHQTE HRRVNNAFLDRLQGKSQPGGLEQSGGCWNMNSGNSWGSLLVFS RHLRVYEKILTPIWPSSTDLEKPHEML FLNVILFSLTVFTLISTAHTLDRAVRSDWLLLVLIYACLEELI PELIFNLYCQGNATLFF |

TABLE 3-continued

| | | |
|---|---|---|
| IFIT3 (SEQ ID NO: 16) | gi\|31542980\|ref\| NP_001540.21 interferon-induced protein with tetratricopeptide repeats 3 [Homo sapiens] | MSEVTKNSLEKILPQLKCHFTWNLFKEDSVSRDLEDRVCNQIE FLNTEFKATMYNLLAYIKHLDGNNEAA LECLRQAEELIQQEHADQAEIRSLVTWGNYAWVYYHLGRLSDA QIYVDKVKQTCKKFSNPYSIEYSELDC EEGWTQLKCGRNERAKVCFEKALEEKPNNPEFSSGLAIAMYHL DNHPEKQFSTDVLKQAIELSPDNQYVK VLLGLKLQKMNKEAEGEQFVEEALEKSPCQTDVLRSAAKFYRR KGDLDKAIELFQRVLESTPNNGYLYHQ IGCCYKAKVRQMQNTGESEASGNKEMIEALKQYAMDYSNKALE KGLNPLNAYSDLAEFLETECYQTPFNK EVPDAEKQQSHQRYCNLQKYNGKSEDTAVQHGLEGLSISKKST DKEEIKDQPQNVSENLLPQNAPNYWYL QGLIHKQNGDLLQAAKCYEKELGRLLRDAPSGIGSIFLSASEL EDGSEEMGQGAVSSSPRELLSNSEQLN |
| LY6E (SEQ ID NO: 17) | gi\|119602691\|gb\| EAW82285.1\| lymphocyte antigen 6 complex, locus E, isoform CRA_a [Homo sapiens] | MKIFLPVLLAALLGVERASSLMCFSCLNQKSNLYCLKPTICSD QDNYCVTVSASAGIGNLVTFGHSLSKT CSPACPIPEGVNVAAS |
| OAS2 (SEQ ID NO: 18) | gi\|74229021\|ref\| NP_001027903.1\| 2'-5'-oligoadenylate synthase 2 isoform 3 [Homo sapiens] | MGNGESQLSSVPAQKLGWFIQEYLKPYEECQTLIDEMVNTICD VLQEPEQFPLVQGVAIGGSYGRKTVLR GNSDGTLVLFFSDLKQFQDQKRSQRDILDKTGDKLKFCLFTKW LKNNFEIQKSLDGFTIQVFTKNQRISF EVLAAFNALSKHCWVSGEKSQRSGCQTALCNL |
| PLSCR1 (SEQ ID NO: 19) | gi\|10863877\|ref\| NP_066928.1\| phospholipid scramblase 1 [Homo sapiens] | MDKQNSQMNASHPETNLPVGYPPQYPPTAFQGPPGYSGYPGPQ VSYPPPPAGHSGPGPAGFPVPNQPVYN QPVYNQPVGAAGVPWMPAPQPPLNCPPGLEYLSQIDQILIHQQ IELLEVLTGFETNNKYEIKNSFGQRVY FAAEDTDCCTRNCCGPSRPFTLRIIDNMGQEVITLERPLRCSS CCCPCCLQEIEIQAPPGVPIGYVIQTW HPCLPKFTIQNEKREDVLKISGPCVVCSCCGDVDFEIKSLDEQ CVVGKISKHWTGILREAFTDADNFGIQ FPLDLDVKMKAVMIGACFLIDFMFFESTGSQEQKSGVW |
| SIGLEC1 (SEQ ID NO: 20) | gi\|146424342\|gb\| AAI41885.1\| SIGLEC1 protein [Homo sapiens] | MGFLPKLLLLASFFPAGQASWGVSSPQDVQGVKGSCLLIPCIF SFPADVEVPDGITAIWYYDYSGQRVV SHSADPKLVEARFRGRTEFMGNPEHRVCNLLLKDLQPEDSGSY NFRFEISEVNRWSDVKGTLVTVTEEPR VPTIASPVELLEGTEVDFNCSTPYVCLQEQVRLQWQGQDPARS VTFNSQKFEPTGVGHLETLHMAMSWQD HGRILRCQLSMANHRAQSEIHLQVKYAPRGVKILLSPSGRNIL PGELVTLTCQVNSSYPAVSSIKWLKDG VRLQTKTGVLHLPQAAWSDAGVYTCQAENGVGSLVSPPISLHI FMAEVQVSPAGPILENQTVTLVCNTPN EAPSDLRYSWYKNHVLLEDAHSHTLRLHLATRADTGFYFCEVQ NVHGSERSGPVSVVVNHPPLTPVLTAF LETQAGLVGILHCSVVSEPLATLVLSHGGHILASTSGDSDHSP RFSGTSGPNSLRLEIRDLEETDSGEYK CSATNSLGNATSTLDFHANAARLLISPAAEVVEGQAVTLSCRS GLSPTPDARFSWYLNGALLHEGPGSSL LLPAASSTDAGSYHCRARDGHSASGPSSPAVLTVLYPPRQPTF TTRLDLDAAGAGAGRRGLLLCRVDSDP PARLQLLHKDRVVATSLPSGGGCSTCGGCSPRMKVTKAPNLLR VEIHNPLLEEEGLYLCEASNALGNAST SATFNGQATVLAIAPSHTLQEGTEANLTCNVSREAAGSPANFS WFRNGVLWAQGPLETVTLLPVARTDAA LYACRILTEAGAQLSTPVLLSVLYPPDRPKLSALLDMGQGHMA LFICTVDSRPLALLALFHGEHLLATSL GPQVPSHGRFQAKAEANSLKLEVRELGLGDSGSYRCEATNVLG SSNTSLFFQVRGAWVQVSPSPELQEGQ AVVLSCQVPTGVPEGTSYRWYRDGQPLQESTSATLRFAAITLT QAGAYHCQAQAPGSATTSLAVPISLHV SYAPRHVTLTTLMDTGPGRLGLLLCRVDSDPPAQLRLLHGDRL VASTLQGVGGPEGSSPRLHVAVAPNTL RLEIHGAMLEDEGVYICEASNTLGQASASADFDAQAVNVQVWP GATVREGQLVNLTCLVWTTHPAQLTYT WYQDGQQRLDAHSIPLPNVTVRDATSYRCGVGPPGRAPRLSRP ITLDVLYAPRNLRLTYLLESHGGQLAL VLCTVDSRPPAQLALSHAGRLLASSTAASVPNTLRLELRGPQP RDEGFYSCSARSPLGQANTSLELRLEG VRVILAPEAAVPEGAPITVTCADPAAHAPTLYTWYHNGRWLQE GPAASLSFLVATRAHAGAYSCQAQDAQ GTRSSRPAALQVLYAPQDAVLSSFRDSRARSMAVIQCTVDSEP PAELALSHDGKVLATSSGVHSLASGTG HVQVARNALRLQVQDVPAGDDTYVCTAQNLLGSISTIGRLQVE GARVVAEPGLDVPEGAALNLSCRLLGG |

TABLE 3-continued

| | | |
|---|---|---|
| | | PGPVGNSTFAWFWNDRRLHAEPVPTLAFTHVARAQAGMYHCLA<br>ELPTGAAASAPVMLRVLYPPKTPTMMV<br>FVEPEGGLRGILDCRVDSEPLASLTLHLGSRLVASSQPQGAPA<br>EPHIHVLASPNALRVDIEALRPSDQGE<br>YICSASNVLGSASTSTYFGVRALHRLHQFQQLLWVLGLLVGLL<br>LLLLGLGACYTWSSLILMQPHVRPQPV<br>PHPWAEVI |
| USP18<br>(SEQ ID NO: 21) | gi\|48146549\|emb\|<br>CAG33497.1\| USP18<br>[Homo sapiens] | MSKAFGLLRQICQSILAESSQSPADLEEKKEEDSNMKREQPRE<br>RPRAWDYPHGLVGLHNIGQTCCLNSLI<br>QVFVMNVDFTRILKRITVPRGADEQRRSVPFQMLLLLEKMQDS<br>RQKAVRPLELAYCLQKCNVPLFVQHDA<br>AQLYLKLWNLIKDQITDVHLVERLQALYMIRVKDSLICVDCAM<br>ESSRNSSMLTLPLSLFDVDSKPLKTLE<br>DALHCFFQPRELSSKSKCFCENCGKKTRGKQVLKLTHLPQTLT<br>IHLMRFSIRNSQTRKICHSLYFPQSLD<br>FSQILPMKRESCDAEEQSGGQYELFAVIAHVGMADSGHYCVYI<br>RNAVDGKWFCFNDSNICLVSWEDIQCT<br>YGNPNYHWQETAYLLVYMKMEC |
| RTP4<br>(SEQ ID NO: 22) | gi\|54607029\|ref\|<br>NP_071430.2\|<br>receptor-<br>transporting<br>protein 4 [Homo<br>sapiens] | MVVDFWTWEQTFQELIQEAKPRATWTLKLDGNLQLDCLAQGWK<br>QYQQRAFGWFRCSSCQRSWASAQVQIL<br>CHTYWEHWTSQGQVRMRLFGQRCQKCSWSQYEMPEFSSDSTMR<br>ILSNLVQHILKKYYGNGTRKSPEMPVI<br>LEVSLEGSHDTANCEACTLGICQGLKSCMTKPSKSLLPHLKT<br>GNSSPGIGAVYLANQAKNQSAEAKEAK<br>GSGYEKLGPSRDPDPLNICVFILLLVFIVVKCFTSE |
| DNAPTP6<br>(SEQ ID NO: 23) | gi\|154426310\|ref\|<br>NP_056350.2\|<br>SPATS2-like<br>protein isoform a<br>[Homo sapiens] | MAELNTHVNVKEKIYAVRSVVPNKSNNEIVLVLQQFDFNVDKA<br>VQAFVDGSAIQVLKEWNMTGKKKNNKR<br>KRSKSKQHQGNKDAKDKVERPEAGPLQPQPPQIQNGPMNGCEK<br>DSSSTDSANEKPALIPREKKISILEEP<br>SKALRGVTEGNRLLQQKLSLDGNPKPIHGTTERSDGLQWSAEQ<br>PCNPSKPKAKTSPVKSNTPAAHLEIKP<br>DELAKKRGPNIEKSVKDLQRCTVSLTRYRVMIKEEVDSSVKKI<br>KAAFAELHNCIIDKEVSLMAEMDKVKE<br>EAMEILTARQKKAEELKRLTDLASQMAEMQLAELRAEIKHFVS<br>ERKYDEELGKAARFSCDIEQLKAQIML<br>CGEITHPKNNYSSRTPCSSLLPLLNAHAATSGKQSNFSRKSST<br>HNKPSEGKAANPKMVSSLPSTADPSHQ<br>TMPANKQNGSSNQRRRFNPQYHNNRLNGPAKSQGSGNEAEPLG<br>KGNSRHEHRRQPHNGFRPKNKGGAKNQ<br>EASLGMKTPEAPAHSEKPRRRQHAADTSEARPFRGSVGRVSQC<br>NLCPTRIEVSTDAAVLSVPAVTLVA |

In some aspects, the type I IFN GS that can be suppressed with a fixed dose of an antibody or antigen-binding fragment thereof that modulates type I IFN activity comprises up-regulated expression or activity of at least 4 PD markers. In some aspects, the type I IFN GS comprises up-regulated expression or activity of at least 5 PD markers. In some aspects, the type I IFN GS comprises up-regulated expression or activity of genes IF127, IF144, IF144L, and RSAD2. In some aspects, the type I IFN GS further comprises up-regulated expression or activity of gene IF16.

In some aspects, the genes in a type I IFN GS that can be suppressed with a fixed dose of an antibody or antigen-binding fragment thereof that modulates type I IFN activity are selected based on three primary criteria: (i) prevalence and magnitude of over-expression in patients compared to healthy controls; (ii) ability to be induced in whole blood from healthy donors ex vivo by type I IFN; and, (iii) the ability to be substantially suppressed by an antibody or antigen-binding fragment thereof that modulates type I IFN activity, e.g., MEDI-546 ex vivo in healthy donor peripheral blood mononuclear cells after stimulation by SLE serum (see. e.g., Yao et al., Hum. Genomics Proteomics 2009: 374312 (2009)).

In some aspects, a type I IFN GS score corresponding to up-regulated expression of the type I IFN GS in blood and lesional skin of patients can be calculated from the expression level of the genes in the type I IFN GS. The type I IFN GS score and its suppression after treatment can be measured, for example, in whole blood (e.g., in peripheral blood) or skin samples from a patient.

A fixed dose of an antibody or antigen-binding fragment thereof that modulates type I IFN activity can suppress or neutralize a type I IFN GS of the present disclosure. This suppression can be a reduction in the expression levels in at least one, at least two, at least three, at least four, at least five, at least six, at least seven, at least eight, at least nine, at least 10, at least 11, at least 12, at least 13, at least 14, at least 15, at least 16, at least 17, at least 18, at least 19, at least 20 or at least 21 up-regulated genes in the type I IFN GS. In some specific aspects, the suppression is a reduction in the expression levels of 4 up-regulated genes in the type I IFN GS. In other specific aspects, the suppression is a reduction in the expression levels of 5 up-regulated genes in the type I IFN GS. Suppression can be partial suppression or full suppression of the expression of the genes in the type I IFN GS.

Suppression of the up-regulated expression of the type I IFN GS can be a reduction of at least 2%, at least 3%, at least 4%, at least 5%, at least 7%, at least 8%, at least 10%, at least 15%, at least 25%, at least 30%, at least 35%, at least 40%, at least 45%, at least 50%, at least 60%, at least 70%, at least 75%, at least 80%, or at least 90% of any of the at least one, at least two, at least three, at least five, at least seven, at least eight, at least 10, at least 11, at least 12, at least 13, at least 14, at least 15, at least 16, at least 17, at least 18, at least 19, at least 20 or at least 21 up-regulated genes in a type I IFN GS.

Alternatively, suppression of the up-regulated expression of the type I IFN GS refers to a reduction of expression levels of at least one, at least two, at least three, at least four, at least five, at least six, at least seven, at least eight, at least 10, at least 11, at least 12, at least 13, at least 14, at least 15, at least 16, at least 17, at least 18, at least 19, at least 20 or at least 21 genes, of at most 50%, at most 45%, at most 40%, at most 35%, at most 30%, at most 25%, at most 20%, at most 15%, at most 10%, at most 5%, at most 4%, at most 3%, at most 2%, or at most 1% of the expression levels of those genes in a control or reference. In some aspects, the antibody or antigen-binding fragment thereof that modulates type I IFN activity, e.g., an anti-IFNAR antibody such as MEDI-546 can neutralize the type I IFN GS at fixed doses of about 100 mg, about 300 mg, or about 1000 mg.

A number of controls or reference samples can be used to determine the degree of suppression of a type I IFN GS prior to treatment or after treatment with a fixed dose of an antibody or antigen-binding fragment thereof that modulates type I IFN activity. For example, a type I IFN GS after treatment with a fixed dose of an antibody or antigen-binding fragment thereof that modulates type I IFN activity agent can be compared to the type I IFN GS of the subject prior to the administration of the fixed dose. In other aspects, during a succession of treatment administrations, a type I IFN GS after treatment with a fixed dose of an antibody or antigen-binding fragment thereof that modulates type I IFN activity can be compared to the type I IFN GS of the patient analyzed prior to the administration of the fixed dose. In other aspects, other references such as the average type I IFN GS in a population, the type I IFN GS in a non-responsive patient, or the type I IFN GS in a relapsed patient can be used for comparison.

Up- or down-regulation of gene expression or activity of PD markers in a type I IFN GS can be determined by any means known in the art. For example, up- or down-regulation of gene expression can be detected by determining mRNA levels. mRNA expression may be determined, for exampler, by northern blotting, slot blotting, quantitative reverse transcriptase polymerase chain reaction, or gene chip hybridization techniques. See, e.g., U.S. Pat. Nos. 5,744,305 and 5,143,854 for examples of making nucleic acid arrays for gene chip hybridization techniques. See also Hrovat et al., Cell. Mol. Biol. Lett. 1: 55-69 (2010), Svec et al., Int. J. Exp. Pathol. 1: 44-53 (2010), and Kurokawa et al., Cancer Chemother. Pharmacol. 3: 427-436 (2010), for examples of how to use the TAQMAN® method for measuring gene expression.

Primers that selectively bind to targets in polymerase chain reactions (PCR) can be chosen based on empirically determining primers that hybridize in a PCR reaction and produce sufficient signal to detect the target over background, or can be predicted using the melting temperature of the primer:target duplex as described in Maniatis et al. Molecular Cloning, Second Edition, Section 11.46 (1989). Similarly, nucleic acid probes for detecting PCR products in a TAQMAN® or related method can be empirically chosen or predicted. Such nucleic acid primers and probes (collectively "oligonucleotides") may be between 10 and 30 nucleotides or greater in length.

Up- or down-regulation of gene expression or activity of PD markers in a type I IFN GS can also be determined by detecting protein levels. Methods for detecting protein expression levels include, for example, immuno-based assays such as enzyme-linked immunosorbant assays, western blotting, protein arrays, and silver staining. Up- or down-regulation of gene expression or activity of the PD markers in the type I IFN GS can be also determined by detecting activity of proteins including, but not limited to, detectable phosphorylation activity, de-phosphorylation activity, or cleavage activity. Furthermore, up- or down-regulation of gene expression or activity of PD markers in the type I IFN GS may be determined by detecting any combination of these gene expression levels or activities. Any combination of decreased number and decrease level of PD markers in the type I IFN GS can indicate efficacy.

The present disclosure provides specific methods of suppressing a type I IFN GS in a patient. For example, a type I IFN GS can be suppressed by measuring the type I IFN GS score in a sample taken from a patient having a type I IFN-mediated disease or disorder, relative to a baseline type I IFN GS score; and, subsequently administering to the patient a fixed dose of an antibody or antigen-binding fragment thereof that modulates type I IFN activity if the patient's type I IFN GS score is elevated, wherein the administration of the antibody or antigen-binding fragment thereof suppresses the IFN GS of the patient.

A type I IFN GS can also be suppressed by administering to a patient having a type I IFN-mediated disease or disorder a fixed dose of an antibody or antigen-binding fragment thereof that modulates type I IFN activity; measuring the patient's type I IFN GS score relative to a baseline IFN GS score; and, then increasing the amount or frequency of subsequent fixed doses if the patient's type I IFN GS score is elevated; wherein the administration of the antibody or antigen-binding fragment thereof suppresses the IFN GS of the patient.

In some aspects, a type I IFN GS can be suppressed by submitting a sample taken from a patient with a type I IFN-mediated disease or disorder for measurement of an type I IFN GS score; determining from the results of the measurement whether the patient's type I IFN GS score is elevated relative to a baseline type I IFN GS score; and, administering to the patient a fixed dose of an antibody or antigen-binding fragment thereof that modulates type I IFN activity if the patient's IFN GS score is elevated; wherein the administration of the antibody or antigen-binding fragment thereof suppresses the IFN GS of the patient.

Another way of suppressing a type I IFN GS in a patient comprises administering to a patient having a type I IFN-mediated disease or disorder a fixed dose of an antibody or antigen-binding fragment thereof that modulates type I IFN activity; submitting a sample taken from the patient for measurement of a type I IFN GS score; determining from the results of the measurement whether the patient's type I IFN GS score is elevated relative to a baseline type I IFN GS score; and, increasing the amount or frequency of subsequent fixed doses if the patient's type I IFN GS score is elevated; wherein the administration of the antibody or antigen-binding fragment thereof suppresses the type I IFN GS of the patient.

In other aspect, a type I IFN GS can be suppressed by submitting a sample taken from a patient with a type I IFN-mediated disease or disorder for measurement of a type I IFN GS score and comparison to a baseline type I IFN GS score; and administering to the patient a fixed dose of an antibody or antigen-binding fragment thereof that modulates type I IFN activity if the patient's type I IFN GS score is elevated; wherein the administration of the antibody or antigen-binding fragment thereof suppresses the type I IFN GS of the patient.

In certain aspects, a type I IFN GS can be suppressed by administering to a patient having a type I IFN-mediated disease or disorder a fixed dose of an antibody or antigen-binding fragment thereof that modulates type I IFN activity; submitting a sample taken from the patient for measurement of a type I IFN GS score and comparison to a baseline type I IFN GS score; and, increasing the amount or frequency of subsequent fixed doses if the patient's type I IFN GS score is elevated; wherein the administration of the antibody or antigen-binding fragment thereof suppresses the type I IFN GS of the patient.

In another aspect, a method of suppressing a type I IFN GS in a patient comprises measuring a type I IFN GS score from a sample taken from a patient having a type I IFN-mediated disease or disorder; determining whether the patient's type I IFN GS score is elevated relative to a baseline type I IFN GS score; and, instructing a healthcare provider to administer a fixed dose of an antibody or antigen-binding fragment thereof that modulates type I IFN activity if the patient's type I IFN GS score is elevated; wherein the administration of the antibody or antigen-binding fragment thereof suppresses the type I IFN GS of the patient. In a certain aspect, a method of suppressing a type I IFN GS in a patient comprises obtaining a sample from a patient having a type I IFN-mediated disease or disorder, where the patent has received a fixed dose of an antibody or antigen-binding fragment thereof that modulates type I IFN activity; measuring an type I IFN GS score from the sample; determining whether the patient's type I IFN GS score is elevated relative to a baseline type I IFN GS score; and, instructing a healthcare provider to increase the amount or frequency of subsequent fixed doses if the patient's type I IFN GS score is elevated; wherein the administration of the antibody or antigen-binding fragment thereof suppresses the type I IFN GS of the patient.

One skilled in the art will appreciate, for example, that samples can be obtained by different methods known in the art, that the samples can be obtained from different tissues, that samples can be obtained at different times, and that different individuals and entities can perform the different steps in the methods disclosed above, as it is discussed in the following sections.

Methods of Treatment, Monitoring, and Prognosing

The present disclosure also provides methods of treatment with an antibody or antigen-binding fragment thereof that modulates type I IFN activity and can suppress a type I IFN GS at fixed doses, thus resulting in a decrease in one or more symptoms of the type I IFN-mediated disease or disorder.

Treatment with the antibody or antigen-binding fragment thereof that modulates type I IFN activity can result in fewer flare-ups related to the type I IFN-mediated disease or disorder, improve prognosis for the patient having the type I IFN-mediated disease or disorder, provide a higher quality of life for the patient, alleviate the need to co-administer second therapeutic agents (e.g., steroids), lessen the dosage of administration of a second agent to the patient, or reduces the number of hospitalizations of the patient that are related to the type I IFN-mediated disease or disorder.

In order to treat a patient, samples from the patient can be obtained before or after the administration of an antibody or antigen-binding fragment thereof that modulates type I IFN activity. In some cases, successive samples can be obtained from the patient after treatment has commenced or after treatment has ceased. Samples can, e.g., be requested by a healthcare provider (e.g., a doctor) or healthcare benefits provider, obtained and/or processed by the same or a different healthcare provider (e.g., a nurse, a hospital) or a clinical laboratory, and after processing, the results can be forwarded to yet another healthcare provider, healthcare benefits provider or the patient. Similarly, the measuring/determination of type I IFN GS scores, comparisons between type IFN GS scores can be, evaluation of the type I IFN GS scores and treatment decisions can be performed by one or more healthcare providers, healthcare benefits providers, and/or clinical laboratories.

As used herein, the term "healthcare provider" refers individuals or institutions which directly interact and administer to living subjects, e.g., human patients. Non-limiting examples of healthcare providers include doctors, nurses, technicians, therapist, pharmacists, counselors, alternative medicine practitioners, medical facilities, doctor's offices, hospitals, emergency rooms, clinics, urgent care centers, alternative medicine clinics/facilities, and any other entity providing general and/or specialized treatment, assessment, maintenance, therapy, medication, and/or advice relating to all, or any portion of, a patient's state of health, including but not limited to general medical, specialized medical, surgical, and/or any other type of treatment, assessment, maintenance, therapy, medication and/or advice.

As used herein, the term "clinical laboratory" refers to a facility for the examination or processing of materials derived from a living subject, e.g., a human being. Non-limiting examples of processing include biological, biochemical, serological, chemical, immunohematological, hematological, biophysical, cytological, pathological, genetic, or other examination of materials derived from the human body for the purpose of providing information, e.g., for the diagnosis, prevention, or treatment of any disease or impairment of, or the assessment of the health of living subjects, e.g., human beings. These examinations can also include procedures to collect or otherwise obtain a sample, prepare, determine, measure, or otherwise describe the presence or absence of various substances in the body of a living subject, e.g., a human being, or a sample obtained from the body of a living subject, e.g., a human being.

As used herein, the term "healthcare benefits provider" encompasses individual parties, organizations, or groups providing, presenting, offering, paying for in whole or in part, or being otherwise associated with giving a patient access to one or more healthcare benefits, benefit plans, health insurance, and/or healthcare expense account programs.

In some aspects, a healthcare provider can administer or instruct another healthcare provider to administer an antibody or antigen-binding fragment thereof that modulates type I IFN activity. A healthcare provider can implement or instruct another healthcare provider or patient to perform the following actions: obtain a sample, process a sample, submit a sample, receive a sample, transfer a sample, analyze or measure a sample, quantify a sample, provide the results obtained after analyzing/measuring/quantifying a sample, receive the results obtained after analyzing/measuring/quantifying a sample, compare/score the results obtained after analyzing/measuring/quantifying one or more samples, provide the comparison/score from one or more samples, obtain the comparison/score from one or more samples, administer a therapeutic agent (e.g., an antibody or antigen-binding fragment thereof that modulates type I IFN activity), commence the administration of a therapeutic agent, cease the administration of a therapeutic agent, continue the administration of a therapeutic agent, temporarily interrupt the administration of a therapeutic agent, increase the amount of administered therapeutic agent, decrease the amount of administered therapeutic agent, continue the administration of an amount of a therapeutic agent, increase the frequency of administration of a therapeutic agent, decrease the frequency of administration of a therapeutic agent, maintain the same dosing frequency on a therapeutic agent, replace a therapeutic agent by at least another therapeutic agent, combine a therapeutic agent with at least another treatment or additional therapeutic agent.

In some aspects, a healthcare benefits provider can authorize or deny, for example, collection of a sample, processing of a sample, submission of a sample, receipt of a sample, transfer of a sample, analysis or measurement a sample, quantification a sample, provision of results obtained after analyzing/measuring/quantifying a sample, transfer of results obtained after analyzing/measuring/quantifying a sample, comparison/scoring of results obtained after analyzing/measuring/quantifying one or more samples, transfer of the comparison/score from one or more samples, administration a therapeutic agent, commencement of the administration of a therapeutic agent, cessation of the administration of a therapeutic agent, continuation of the administration of a therapeutic agent, temporary interruption of the administration of a therapeutic agent, increase of the amount of administered therapeutic agent, decrease of the amount of administered therapeutic agent, continuation of the administration of an amount of a therapeutic agent, increase in the frequency of administration of a therapeutic agent, decrease in the frequency of administration of a therapeutic agent, maintain the same dosing frequency on a therapeutic agent, replace a therapeutic agent by at least another therapeutic agent, or combine a therapeutic agent with at least another treatment or additional therapeutic agent. In addition a healthcare benefits provides can, e.g., authorize or deny the prescription of a therapy, authorize or deny coverage for therapy, authorize or deny reimbursement for the cost of therapy, determine or deny eligibility for therapy, etc.

In some aspects, a clinical laboratory can, for example, collect or obtain a sample, process a sample, submit a sample, receive a sample, transfer a sample, analyze or measure a sample, quantify a sample, provide the results obtained after analyzing/measuring/quantifying a sample, receive the results obtained after analyzing/measuring/quantifying a sample, compare/score the results obtained after analyzing/measuring/quantifying one or more samples, provide the comparison/score from one or more samples, obtain the comparison/score from one or more samples, The above enumerated actions can be performed by a healthcare provider, healthcare benefits provider, or patient automatically using a computer-implemented method (e.g., via a web service or stand-alone computer system).

Patient samples include any biological fluid or issue, such as whole blood, serum, muscle, saliva, Samples include any biological fluid or tissue, such as whole blood, serum, muscle, saliva, urine, synovial fluid, bone marrow, cerebrospinal fluid, nasal secretions, sputum, amniotic fluid, bronchoalveolar lavage fluid, peripheral blood mononuclear cells, total white blood cells, lymph node cells, spleen cells, tonsil cells, or skin. In some specific aspects, that patient sample is blood or a fraction thereof, muscle, skin, or a combination thereof. Patient samples can be obtained by any means known in the art.

Accordingly, the present disclosure provides a method of treating a patient having a type I IFN-mediated disease or disorder comprising measuring a type I IFN GS score in a sample taken from a patient having a type I IFN-mediated disease or disorder, relative to a baseline IFN GS score; and administering to the patient a fixed dose of an antibody or antigen-binding fragment thereof that modulates type I IFN activity if the patient's type I IFN GS score is elevated; wherein the fixed dose of the antibody or fragment thereof effectively treats the disease or disorder. Also provided is a method of treating a patient having a type I IFN-mediated disease or disorder comprising administering to a patient having a type I IFN-mediated disease or disorder a fixed dose of an antibody or antigen-binding fragment thereof that modulates type I IFN activity; measuring the patient's type I IFN GS score relative to a baseline IFN GS score; and increasing the amount or frequency of subsequent fixed doses if the patient's IFN GS score is elevated; wherein suppression of the type I IFN GS of the patient is indicative of treatment efficacy.

In some aspects, the present disclosure provides a method of treating a patient having a type I IFN-mediated disease or disorder comprising: submitting a sample taken from a patient with a type I IFN-mediated disease or disorder for measurement of a type I IFN GS score; determining from the results of the measurement whether the patient's type I IFN GS score is elevated relative to a baseline type I IFN GS score; and, administering to the patient a fixed dose of an antibody or antigen-binding fragment thereof that modulates type I IFN activity if the patient's type I IFN GS score is elevated; wherein the fixed dose of the antibody or fragment thereof effectively treats the disease or disorder.

In other aspects, a method of treating a patient having a type I IFN-mediated disease or disorder comprises administering to a patient having a type I IFN-mediated disease or disorder a fixed dose of an antibody or antigen-binding fragment thereof that modulates type I IFN activity; submitting a sample taken from the patient for measurement of an IFN GS score; determining from the results of the measurement whether the patient's type I IFN GS score is elevated relative to a baseline type I IFN GS score; and, increasing the amount or frequency of subsequent fixed doses if the patient's type I IFN GS score is elevated; wherein suppression of the type I IFN GS of the patient is indicative of treatment efficacy.

In some aspects, the method of treating a patient having a type I IFN-mediated disease or disorder comprises submitting a sample taken from a patient with a type I IFN-mediated disease or disorder for measurement of a type I IFN GS score and comparison to a baseline IFN GS score; and administering to the patient a fixed dose of an antibody or antigen-binding fragment thereof that modulates type I IFN activity if the patient's type I IFN GS score is elevated; wherein the fixed dose of the antibody or fragment thereof effectively treats the disease or disorder. In other aspects, the method of treating a patient having a type I IFN-mediated disease or disorder comprises administering to a patient having a type I IFN-mediated disease or disorder a fixed dose of an antibody or antigen-binding fragment thereof that modulates type I IFN activity; submitting a sample taken from the patient for measurement of a type I IFN GS score and comparison to a baseline type I IFN GS score; and increasing the amount or frequency of subsequent fixed doses if the patient's type I IFN GS score is elevated; wherein suppression of the type I IFN GS of the patient is indicative of treatment efficacy.

In some aspects, the method of treating a patient having a type I IFN-mediated disease or disorder comprises measuring a type I IFN GS score from a sample taken from a patient having a type I IFN-mediated disease or disorder; determining whether the patient's IFN GS score is elevated relative to a baseline type I IFN GS score; instructing a healthcare provider to administer a fixed dose of an antibody or antigen-binding fragment thereof that modulates type I IFN activity if the patient's type I IFN GS score is elevated; wherein the fixed dose of the antibody or fragment thereof effectively treats the disease or disorder. In some aspects, the method of treating a patient having a type I IFN-mediated disease or disorder comprises obtaining a sample from a patient having a type I IFN-mediated disease or disorder, where the patent has received a fixed dose of an antibody or antigen-binding fragment thereof that modulates type I IFN activity; measuring a type I IFN GS score from the sample; determining whether the patient's type I IFN GS score is elevated relative to a baseline type I IFN GS score; instructing a healthcare provider to increase the amount or frequency of subsequent fixed doses if the patient's type I IFN GS score is elevated; wherein suppression of the type I IFN GS of the patient is indicative of treatment efficacy.

In methods of monitoring or prognosing disease progression of a patient having a type I IFN-mediated disease or disorder, samples from the patient may be obtained before or after administration of a therapeutic agent. In some cases, the therapeutic agent can be a different antibody or other biologic (e.g., fusion protein or conjugate) or small molecule. In this respect, the methods provided in the present disclosure can be applied to a patient undergoing a first therapy, determining a type I IFN GS score, and determining according to that type I IFN GS score whether to continue or discontinue the first therapy. The methods provided in the present disclosure can be applied to a patient undergoing a first therapy, determining a type I IFN GS score, and determining according to that type I IFN GS score whether to replace or combine the first therapy with the administration of a fixed dose of an antibody or antigen-binding fragment thereof or small molecule that modulates type I IFN activity.

The sample obtained from the patient may be obtained prior to a first administration of a therapeutic agent, e.g., antibody or antigen-binding fragment thereof or small molecule that modulates type I IFN activity. In this situation, the patient is naïve to the antibody or antigen-binding fragment thereof that modulates type I IFN activity. Alternatively, the sample obtained from the patient can occur after administration of a fixed dose of the antibody or antigen-binding fragment thereof that modulates type I IFN activity in the course of treatment. For example, the therapeutic agent can be administered prior to the initiation of the monitoring protocol. Following administration a fixed dose of the antibody or antigen-binding fragment thereof that modulates type I IFN activity, additional samples can be obtained from the patient and type I IFN GS measurement be compared. The samples can be of the same type or of a different type. For example, each sample obtained can be a blood sample, or each sample obtained can be a skin or muscle sample. The type I IFN GS detected in each sample can be the same, can overlap substantially, or can be similar.

The sample can be obtained at any time before or after the administration of a fixed dose of the antibody or antigen-binding fragment thereof that modulates type I IFN activity. The sample obtained after the administration of the fixed dose of the antibody or antigen-binding fragment thereof that modulates type I IFN activity can be obtained at least 2, at least 3, at least 4, at least 5, at least 7, at least 8, at least 9, at least 10, at least 12, or at least 14 days after administration.

The sample obtained after administration of the fixed dose of antibody or antigen-binding fragment thereof that modulates type I IFN activity can be obtained at least 2, at least 3, at least 4, at least 5, at least 6, at least 7, or at least 8 weeks after administration. The sample obtained after administration of the fixed dose of antibody or antigen-binding fragment thereof that modulates type I IFN activity can be obtained at least 2, at least 3, at least 4, at least 5, or at least 6 months following administration.

Additional samples can be obtained from the patient following administration of a fixed dose of the antibody or antigen-binding fragment thereof that modulates type I IFN activity. At least 2, at least 3, at least 4, at least 5, at least 6, at least 7, at least 8, at least 9, at least 10, at least 12, at least 15, at least 20, at least 25 samples can be obtained from the patient to monitor progression or regression of the type I IFN-mediated disease or disorder over time. Progression of the type I IFN-mediated disease or disorder can be monitored over a time period of at least 1 week, at least 2 weeks, at least 3 weeks, at least 4 weeks, at least 5 weeks, at least 6 weeks, at least 7 weeks, at least 2 months, at least 3 months, at least 4 months, at least 5 months, at least 6 months, at least 1 year, at least 2 years, at least 3 years, at least 4 years, at least 5 years, at least 10 years, or over the lifetime of the patient.

Additional samples can be obtained from the patient at regular intervals such as at monthly, bi-monthly, once a quarter year, twice a year, or yearly intervals. The samples can be obtained from the patient following administration of a fixed dose of the antibody or antigen-binding fragment thereof that modulates type I IFN activity at regular intervals. For instance, the samples can be obtained from the patient at one week, or at two weeks, or at three weeks, or at one month, or at two months following each administration of the fixed dose of antibody or antigen-binding fragment thereof that modulates type I IFN activity. Alternatively, multiple samples may be obtained from the patient following each administration.

Disease progression in a patient can similarly be monitored in the absence of administration of a fixed dose of an antibody or antigen-binding fragment thereof that modulates type I IFN activity. Samples can periodically be obtained from the patient having the disease or disorder. Disease progression can be identified if the type I IFN GS score increases in a later-obtained sample relative to an earlier obtained sample. The type I IFN GS score can increase by at least 1, at least 2, at least 3, at least 4, at least 5, at least 6, at least 7, at least 8, at least 9, or at least 10. Disease progression can be identified if the type IFN GS score increases by at least 10%, at least 20%, at least 25%, at least 30%, at least 35%, at least 40%, at least 50%, at least 60%, at least 70%, at least 80%, at least 90%, or at least 95%. Disease progression may be identified if level of any given PD marker in the type I IFN GS increases by at least 10%, at least 20%, at least 25%, at least 30%, at least 35%, at least 40%, at least 50%, at least 60%, at least 70%, at least 80%, at least 90%, or at least 95%. The number of up-regulated PD markers in the type I IFN GS with increased levels may be at least 1, at least 2, at least 3, at least 4, at least 5, at least 6, at least 7, at least 8, at least 9, at least 10, at least 15, or at least 20. Any combination of increased number and increased level of up-regulated in the type I IFN GS can indicate disease progression.

Disease regression can also be identified in a patient having a disease or disorder, not treated by a therapeutic agent. In this instance, regression can be identified if the type I IFN GS score decreases in a later-obtained sample relative to an earlier obtained sample. Disease regression can be identified if the level of any given up-regulated PD marker in the type I IFN GS decreases by at least 10%, at least 20%, at least 25%, at least 30%, at least 35%, at least 40%, at least 50%, at least 60%, at least 70%, at least 80%, at least 90%, or at least 95%. The number of up-regulated PD markers in the type I IFN GS with decreased levels may be at least 1, at least 2, at least 3, at least 4, at least 5, at least 6, at least 7, at least 8, at least 9, at least 10, at least 15, or at least 20. Disease progression or disease regression can be monitored by obtaining samples over any period of time and at any interval.

Disease progression or disease regression can be monitored by obtaining samples over the course of at least 1 week, at least 2 weeks, at least 3 weeks, at least 4 weeks, at least 5 weeks, at least 6 weeks, at least 7 weeks, at least 2 months, at least 3 months, at least 4 months, at least 5 months, at least 6 months, at least 1 year, at least 2 years, at least 3 years, at least 4 years, at least 5 years, at least 10 years, or over the lifetime of the patient. Disease progression or disease regression can be monitored by obtaining samples at least monthly, bi-monthly, once a quarter year, twice a year, or yearly. The samples need not be obtained at strict intervals.

Variance in the type I IFN GS scores among the samples after administration of a fixed dose of an antibody or antigen-binding fragment thereof that modulates type I IFN activity can guide treatment strategy of the type I IFN-mediated disease or disorder. Treatment strategy can be, for example, increase or decrease in dosage of a particular therapeutic, increase or decrease the frequency of administration of a particular therapeutic, removal or addition of particular therapeutics administered to a patient, commencement or suspension or treatment, etc. Accordingly, the present disclosure provides specific methods to monitor therapeutic efficacy of an antibody or antigen-binding fragment thereof that modulates type I IFN activity in a patient having a type I IFN-mediated disease or disorder. In some aspects, the method of monitoring therapeutic efficacy of a fixed dose of an antibody or antigen-binding fragment thereof that modulates type I IFN activity in a patient having a type I IFN-mediated disease or disorder comprises measuring a first type I IFN GS score in a sample taken from a patient having a type I IFN-mediated disease or disorder; administering to the patient a fixed dose of an antibody or antigen-binding fragment thereof that modulates type I IFN activity; measuring a second type I IFN GS score in a sample taken from the patient following antibody administration; and comparing the second type I IFN GS score to the first type I IFN GS score; wherein a decrease between the first and second type I IFN GS scores indicates efficacy or good prognosis.

In one aspect, the method of monitoring therapeutic efficacy of a fixed dose of an antibody or antigen-binding fragment thereof that modulates type I IFN activity in a patient having a type I IFN-mediated disease or disorder comprises submitting a sample taken from a patient with a type I IFN-mediated disease or disorder for measurement of a first type I IFN GS score; administering to the patient a fixed dose of an antibody or antigen-binding fragment thereof that modulates type I IFN activity; submitting a sample taken from a patient with a type I IFN-mediated disease or disorder for measurement of a second type I IFN GS score; and comparing the second type I IFN GS score to the first type I IFN GS score; wherein a decrease between the first and second IFN GS scores indicates efficacy or good prognosis. In another aspect, the method of monitoring therapeutic efficacy of a fixed dose of an antibody or antigen-binding fragment thereof that modulates type I IFN activity in a patient having a type I IFN-mediated disease or disorder comprises measuring a first type I IFN GS score from a sample taken from a patient having a type I IFN-mediated disease or disorder; instructing a healthcare provider to administer a fixed dose of an antibody or antigen-binding fragment thereof that modulates type I IFN activity; measuring a second type I IFN GS score in a sample taken from the patient following antibody administration; and comparing the second type I IFN GS score to the first type I IFN GS score; wherein a decrease between the first and second type I IFN GS scores indicates efficacy or good prognosis.

In some specific aspects, the method of monitoring therapeutic efficacy further comprises, for example:
(a) measuring the patient's type I IFN GS score relative to a baseline IFN GS score, relative to the patient's earlier IFN GS score, or both, after the administration of the fixed dose;
(b) measuring the patient's type I IFN GS score relative to a baseline IFN GS score, relative to the patient's earlier type I IFN GS score, or both, after the administration of a subsequent fixed dose;
(c) submitting a sample from the patient for measurement of the patient's type I IFN GS score relative to a baseline type I IFN GS score, relative to the patient's earlier type I IFN GS score, or both, after the administration of the fixed dose;
(d) submitting a sample from the patient for measurement of the patient's type I IFN GS score relative to a baseline type I IFN GS score, relative to the patient's earlier type I IFN GS score, or both, after the administration of a subsequent fixed dose;
(e) a combination of two or more of the steps above.

In other aspect, the method of monitoring therapeutic efficacy further comprises, for example:
(a) increasing/decreasing the amount or frequency of subsequent fixed doses if the patent's IFN GS score remains elevated;
(b) increasing/decreasing the amount or frequency of subsequent fixed doses if the patent's IFN GS score remains elevated;
(c) increasing/decreasing the amount or frequency of subsequent fixed doses if the patent's IFN GS score remains elevated;
(d) a combination of two or more of the steps above.

Kits

Also provided in the present disclosure is a kit for detecting a type I IFN genetic signature (IFN GS) common to two diseases whose pathogeneses are mediated by type I IFN. The kit can comprise containers filled with nucleic acid probes (e.g., oligonucleotides) capable of hybridizing nucleic acids (e.g., mRNA) encoding the PD markers disclosed herein or fragments thereof. Specifically, the present disclosure provides a kit for detecting a type I IFN genetic signature (type I IFN GS) common to two diseases, e.g., SSc and SLE, whose pathogeneses are mediated by type I IFN comprising a set of diagnostic assays capable of measuring differentially regulated pharmacodynamic (PD) marker genes in a patient sample, wherein the type I IFN GS is suppressed by the administration of a fixed dose of an antibody or antigen-binding fragment thereof that modulates type I IFN activity.

In some aspects, the kit comprises oligonucleotide probes for at least one PD marker gene selected from the group consisting of IFI6, RSAD2, IFI44, IFI44L, IFI27, MX1, IFIT1, HERC5, ISG15, LAMP3, OAS3, OAS1, EPST1, IFIT3, LY6E, OAS2, PLSCR1, SIGLEC1, USP18, RTP4, and DNAPTP6. In other aspects, the kit can comprise 2, 3, 4, 5, 6, 7, 8, 9, 10, 11, 12, 13, 14, 15, 16, 17, 18, 19, 20, or 21 oligonucleotide probes capable of detecting the PD marker genes described above. In some aspects, a PD marker genes can be detected by two or more oligonucleotide probes. Oligonucleotide probes can be labeled by any method known in the art, e.g., using fluorescent or radioactive labels. Oligonucleotide probes in the kit can be unlabeled. In some aspects, the kit also contains controls and/or calibration standards.

In other aspects, the kit comprises oligonucleotide probes for at least five of the PD marker genes, e.g., IF127, IF144, IF144L, and RSAD2. In some aspects, the kit also comprises oligonucleotide probes for IF16.

In some aspects, the kit can be used for diagnostic or investigational purposes on patient samples such as blood or a fraction thereof, muscle, skin, or a combination thereof. The kit can comprise oligonucleotide capable of hybridizing to DNA and/or RNA. Such DNA and/or RNA can be a full gene nucleic acid, or correspond to a fragment or degradation product. In some aspects, the kit can be used the PD markers disclosed herein or fragments thereof, preferably in a purified form.

Optionally associated with the kit's container(s) can be a notice in the form prescribed by a governmental agency regulating the manufacture, use or sale of pharmaceuticals or biological products, which notice reflects approval by the agency of manufacture, use or sale for human administration.

Computer Implemented Methods and Computer-Readable Media

The present disclosure also provides computer-implemented a method for predicting an optimal dosage regimen with an antibody or antigen-binding fragment thereof that modulates type I IFN activity, a method for identifying an antibody or antigen-binding fragment thereof that modulates type I IFN activity as a candidate therapeutic agent for treating a type I IFN-mediated disease or disorder, a method for identifying a patient as a candidate for therapy with an antibody or antigen-binding fragment thereof that modulates type I IFN activity, and a method of designing a personalized therapy for treating a type I IFN-mediated disease or disorder with an antibody or antigen binding fragment thereof that modulates type I IFN activity.

In these methods, PK/PD data from a second type I IFN-mediated disease or disorder is inputted into a computer system comprising a pharmacokinetic-pharmacodynamic (PK/PD) stochastic model based on PK/PD data corresponding a first type I IFN-mediated disease or disorder, wherein the inputted PK/PD data from the second type I IFN-mediated disease or disorder is used to adjust the PK/PD stochastic model. The adjusted PK/PD stochastic model can be applied to the inputted PK/PD data from the second type I IFN-mediated disease or disorder. Based on the application of the adjusted PK/PD stochastic model to the inputted PK/PD from the second type I IFN-mediated disease or disorder, an optimal dosage regimen, a candidate therapeutic agent, a candidate patient for therapy, or a personalized therapy can be identified.

The present disclosure also provides a computer-readable medium containing program instructions for predicting an optimal dosage regimen with an antibody or antigen-binding fragment thereof that modulates type I IFN activity, program instructions for identifying an antibody or antigen-binding fragment thereof that modulates type I IFN activity as a candidate therapeutic agent for treating a type I IFN-mediated disease or disorder, instructions for identifying a patient as a candidate for therapy with an antibody or antigen-binding fragment thereof that modulates type I IFN activity, and instructions for designing a personalized therapy for treating a type I IFN-mediated disease or disorder with an antibody or antigen binding fragment thereof that modulates type I IFN activity. The execution of the program instructions by one or more processors of a computer system causes the one or more processors to carry out the steps of (a) processing inputted PK/PD data from a second type I IFN-mediated disease or disorder; (b) adjusting a PK/PD stochastic model based on PK/PD data corresponding a first type I IFN-mediated disease or disorder with the processed PK/PD data from the second type I IFN-mediated disease or disorder; and, (c) executing a stochastic simulation applying the adjusted PK/PD stochastic model to the inputted PK/PD data from the second type I IFN-mediated disease or disorder. The output of the simulation identifies, e.g., an optimal dosage of the antibody or antigen-binding fragment thereof that modulates type I IFN activity in the second type I IFN-mediated disease or disorder, an antibody or antigen-binding fragment thereof that modulates type I IFN activity as a candidate therapeutic agent for treating the second type I IFN-mediated disease or disorder, a patient with the second type I IFN-mediated disease as a candidate for therapy with an antibody or antigen-binding fragment thereof that modulates type I IFN activity, or a personalized therapy for treating the second type I IFN-mediated disease or disorder with an antibody or antigen binding fragment thereof that modulates type I IFN activity.

The computer implemented methods and computer-readable media disclosed herein can be implemented as a tool to be used by healthcare providers, either as a stand-alone tool or via a server. The tool can include computer-readable components, an input/output system, and one or more processing units. The input/output system can be any suitable interface between user and computer system, for input and output of data and other information, and for operable interaction with the one or more processing units. In one aspect, data to be inputted into the tool can be derived from in vitro or in vivo sources. In some aspects, the user can evaluate alternatives by changing one or more of the parameters and constants of the system. In a forward mode of operation, the user can predict absorption, individual parameters of absorption, as well as one or more other bioavailability parameters of a compound from relatively few input variables. Additionally, the user can evaluate alternatives by changing any of the parameters and constants of the system, and observe the ripple effect of the change in one or more parameters on all other parameters. For instance, the user can evaluate alternative absorption profiles using "What if" analysis with any parameter of the system.

In a backward mode of operation, the user can specify one or more objective parameters of a formulation of interest and the tool and method of the disclosure would generate alternatives to satisfy the objective. The user can also vary input dosing and formulation parameters for "What if" analysis. Simulated absorption profiles can then be utilized for preparing suitable formulations and/or dosing regimens. Solubility, permeability, bioavailability, doses and the like also may be estimated in the backward mode of operation.

In some aspects, the input/output system may provide direct input form measuring equipment. The input/output system preferably provides an interface for a standalone computer or integrated multi-component computer system having a data processor, a memory, and a display. Data may be entered numerically, as a mathematical expression or as a graph that represents a physiological or pharmacokinetic parameter.

All patents and publications referred to herein are expressly incorporated by reference in their entireties.

EXAMPLES

Materials and Methods

Patient Population and Study Design.

An open-label, cohort dose-escalation Phase 1 study in adult patients with diffuse scleroderma (SSc) (ClinicalTrials.gov identifier NCT00930683) was conducted in accordance with the Declaration of Helsinki (1996), the International Conference on Harmonisation Guidelines for Good Clinical Practice (Topic E6), Institutional Review Boards (21 CFR Part 56) and Investigational New Drug Application (21 CFR Part 312), to evaluate the safety, tolerability, pharmacokinetics (PK), immunogenicity and pharmacodynamics (PD) of single and multiple intravenous doses of MEDI-546, a fully human monoclonal antibody directed against subunit 1 of the type I Interferon Receptor. The protocol was reviewed and approved by the Institutional Review Board or Independent Ethics Committee of each participating center prior to study initiation. Written informed consent was obtained from each participant before the conduct of any protocol-specific activity or study entry.

A total of 34 adult diffuse SSc patients who had skin thickening in an area suitable for repeat biopsy were enrolled to receive single (0.1, 0.3, 1.0, 3.0, 10.0, or 20.0 mg/kg) or multiple doses (0.3, 1.0, or 5.0 mg/kg weekly×4) of MEDI-546, which was administered as an intravenous (IV) infusion over at least 30 minutes. The starting dose of 0.1 mg/kg was based on the human equivalence dose (HED) of primate pharmacologically active dose (PAD) and the predicted short duration of IFNAR occupancy by MEDI-546 in humans from translational simulations. Cohort designation, patient demographics, and baseline type I IFN GS status are summarized in TABLE 4.

PK Sample Collection and Bioanalytical Assays.

Serum PK samples were obtained from all patients pre-dose and at pre-designated timepoints up to Day 84 (single-dose cohorts) or Day 105 (multiple-dose cohorts) for the measurement of MEDI-546 concentrations using a validated electrochemiluminescence (ECL) assay on the Meso Scale Discovery (MSD) platform. In brief, MEDI-546 was captured by biotinylated soluble interferon alpha receptor (sIFNAR1) bound to streptavidin-coated MSD plates. The captured MEDI-546 was detected with a sulfo-TAG labeled monoclonal antibody specifically targeting distinct amino acids within the Fc region of MEDI-546, which was mutated to eliminate antibody-dependent cell-mediated cytotoxicity (ADCC) and complement-dependent cytotoxicity (CDC). An MSD read buffer was added and the plates were placed on a MSD Sector™ Imager Model 6000 reader for the generation and measurement of ECL signals. The assay had a measurement range of 20 to 1,280 ng/mL of MEDI-546 in human serum.

Total RNA Extraction and Microarray Processing.

Whole blood samples were collected from all patients at screening and pre-designated PK visits to determine levels of mRNA for type I IFN-inducible genes. Skin biopsies were also collected pre-dose (Day 0) and on Day 7 (single-dose) or Day 28 (multiple-dose). The Human Genome U133 Plus 2.0 array platform (Affymetrix, Santa Clara, Calif.) was used to evaluate the effects of MEDI-546 in whole blood and in lesional skin from matched SSc patient specimens from whom skin biopsy samples were collected. The general procedures for sample processing and data analysis for microarray studies have been described previously (Yao et al., Hum. Genomics Proteomics 2009:374312 (2009); Yao et al., PLoS One 3:e2737 (2008)).

Calculation of the type I Interferon (IFN) Gene Signature (GS).

The type I IFN GS score, a quantity used to express the amount of type I IFN activity present in an individual, was measured in the whole blood or skin. The type I IFN GS score was calculated using a set of five genes (IFI27, IFI44, IFI44L, RSAD2, and IFI6) for each subject. On a log 2 scale, the arithmetic means were calculated for each gene in a set of 24 normal control samples and the difference for each gene was calculated between each individual disease subject and the mean vector of the normal control samples.

The five type I IFN-inducible genes were used to generate subsets of the fold change (FC) data matrix calculated above (dimensions=X*n, where n was the number of total subject samples). The median value across the five genes for each

TABLE 4

Summary of Patient Demographics for MEDI-546 First Time in Human (FTIH) Study in Adult Patients with SSc. Values are shown as median (range) or count (percentage).

| | N | Age, y | Weight, kg | Gender, Female | Race, white | $GS_{IFN}$ Blood, Positive | $GS_{IFN}$ Skin, Positive |
|---|---|---|---|---|---|---|---|
| Single-Dose (mg/kg) | | | | | | | |
| 0.1 | 1 | 41 (41-41) | 64 (64-64) | 1 (100%) | 1 (100%) | 0 (0%) | 0 (0%) |
| 0.3 | 4 | 59.5 (45-69) | 60 (50-61) | 3 (75%) | 3 (75%) | 4 (100%) | 2 (50%) |
| 1 | 4 | 44 (38-54) | 71 (42-103) | 4 (100%) | 2 (50%) | 2 (50%) | 2 (50%) |
| 3 | 4 | 34.5 (19-44) | 66 (48-112) | 3 (75%) | 2 (50%) | 3 (75%) | 1 (25%) |
| 10 | 4 | 46 (35-65) | 65 (50-114) | 4 (100%) | 2 (50%) | 3 (75%) | 2 (50%) |
| 20 | 4 | 46.5 (35-54) | 70 (54-81) | 3 (75%) | 3 (75%) | 3 (75%) | 1 (25%) |
| Multiple-Dose (mg/kg, QW × 4) | | | | | | | |
| 0.3 | 4 | 46 (27-51) | 86 (78-102) | 2 (50%) | 4 (100%) | 1 (25%) | 0 (0%) |
| 1.0 | 4 | 46.5 (42-62) | 65 (50-124) | 3 (75%) | 4 (100%) | 3 (75%) | 2 (50%) |
| 5.0 | 4 | 55 (43-77) | 66 (48-107) | 4 (80%) | 4 (80%) | 3 (60%) | 1 (20%) |
| Total | 34 | 46 (19-77) | 65 (42-124) | 27 (79%) | 25 (74%) | 22 (65%) | 11 (32%) | subject was calculated as the FC score. The FC values were then transposed to a linear scale using the formula $2^{Fc}$, and denoted as the type I IFN GS score. For each subject, the type I IFN GS score was calculated at both baseline and each time point post dose. Then the median type I IFN GS scores for each dose cohort were plotted across time to indicate the degree of suppression of type I IFN activity at different dosage levels.

Target modulation was then calculated as the ratio of the type I IFN GS score post dose to the type I IFN GS score pre-dose ($GS_0$). This quantity was represented as a percentage and for each dose cohort, scaled to the $GS_0$ value. Then this quantity was subtracted from 100% to indicate the remaining percentage of type I IFN GS, so all patients at day 0 (pre-dose) started with 100% target modulation.

Only patients with a positive type I IFN GS score at baseline had PD data calculated using both methods described above. The distribution of type I IFN GS scores at baseline varied for different disease indications and specimen source. For example, the baseline median type I IFN GS scores for SLE patient blood specimens were higher than those of SSc patients (FIG. 1). This same pattern was reinforced in the skin specimens of these two diseases. In SLE patients, the median baseline type I IFN GS scores in skin were slightly higher than in blood specimens. In SSc patients, the median type I IFN GS scores in blood were higher than those in skin specimens. As compared to normal healthy controls, the type I IFN GS scores were higher in both disease and specimen source distributions.

Receptor Internalization Kinetics.

The internalization of MEDI-546 upon binding to IFNAR1 was assessed using live-cell confocal fluorescent imaging technology. MEDI-546 and an isotype control IgG were fluorescently tagged with Alexa647 using a dye-conjugation kit (A-20186) from Invitrogen (Life Technologies Corp, Carlsbad, Calif.). Reaction mixtures were purified from unincorporated fluorescent molecules using size-exclusion mini-columns provided in the kit. IFNAR1-expressing THP-1 cells were maintained in suspension using RPMI growth medium containing 10% FBS, and seeded in a fresh growth medium at 2×105 cells/mL overnight prior to the experiments. On the day of experiments, THP-1 cells were washed and resuspended to a concentration of $3 \times 10^6$ cells/mL.

Cell suspensions were first stained for 10-20 min with cytosol dye, CFSE, from Invitrogen (Life Technologies Corp, Carlsbad, Calif.) in a $CO_2$ incubator at 37° C. Excess CFSE was removed by two washes with 1×PBS. Cells were then pre-chilled, blocked with FcR blockers to prevent FcR-mediated binding, and stained on ice with 1 µg/mL of MEDI-546-Alexa647 or IgG-Alexa647 for 1-2 hours. Following the removal of unincorporated antibodies by centrifugation, cells were resuspended to initial volumes, and dispensed into the wells of 384-well imaging plates.

Cells were then transferred to the environmental control chamber (37° C., 5% CO2 and 70% humidity) of the confocal fluorescent imager, Opera (Perkin Elmer, Waltham, Mass.), where fluorescence images were acquired using a 40× objective lens with a numerical aperture of 0.9 at designated time points to monitor the kinetics of MEDI-546-Alexa647 internalization. The acquired kinetic images were analyzed using an internally-developed algorithm that quantifies fluorescence intensity in the membrane and cytoplasmic compartments of the cells. Accumulation of MEDI-546-Alexa647 fluorescence in the cytoplasm region over time was normalized by the total fluorescence (membrane plus cytoplasm) and the normalized data was used for the assessment of the internalization rate.

PK-PD Model Structure

A 2-compartment PK model with parallel first-order and IFNAR-mediated elimination pathways was developed to describe the observed serum concentration profiles of MEDI-546 in SSc patients (FIG. 4). The first-order elimination pathway represented the clearance of MEDI-546 by the reticulo-endothelial system (CLres), in the same way as for an endogenous IgG. The nonlinear elimination pathway was presumably associated with the IFNAR-mediated clearance (antigen-sink effect). R represented the target receptor (IFNAR1) and AbR was the antibody-receptor complex.

MEDI-546 bound to the receptor ($k_{on}$, $k_{off}$), and the antibody-receptor complex was subsequently internalized and degraded ($k_{int}$) inside the cells. Parameters $k_{syn}$ and $k_{deg}$ represented the endogenous production and degradation of IFNAR1, respectively.

The 2 compartmental PK model with first-order elimination and target-mediated drug disposition with quasi-steady-state approximation was described by the following set of differential equations:

$$k_{on}C \cdot R - (k_{off} + k_{int})RC = 0 \quad \text{(Equation 1)}$$

$$\frac{C \cdot R}{RC} = \frac{k_{off} + k_{int}}{k_{on}} = K_D + \frac{k_{int}}{k_{on}} = K_s \quad \text{(Equation 2)}$$

$$C = \frac{1}{2}\left[(C_{tot} - R_{tot} - K_{ss}) + \sqrt{(C_{tot} - R_{tot} - K_s)^2 + 4K_s C_{tot}}\right] \quad \text{(Equation 3)}$$

$$RC = \frac{R_{tot}C}{K_s + C}; \quad \text{(Equation 4)}$$

$$C_{tot} = \frac{R_{tot}C}{K_s + C} + C$$

$$\frac{dC_{tot}}{dt} = \frac{\text{input}}{V} - k_{el}C - k_{int}RC - k_{SerumTissue}C + \frac{k_{TissueSerum}A_{Tissue}}{V} \quad \text{(Equation 5)}$$

$$\frac{dC}{dt} = -\frac{\frac{\text{input}}{V} + k_{el}C - k_{int}\frac{R_{tot}C}{K_s + C} - k_{SerumTissue}C + \frac{k_{TissueSerum}A_{Tissue}}{V}}{1 + R_{tot}\frac{K_s}{(C + K_s)^2}} \quad \text{(Equation 6)}$$

$$\frac{dA_{Tissue}}{dt} = k_{SerumTissue}C \cdot V - k_{TissueSerum}A_{Tissue} \quad \text{(Equation 7)}$$

$$\frac{dR_{tot}}{dt} = k_{syn} - k_{deg}R_{tot} - (k_{int} - k_{deg})\left(\frac{R_{tot}C}{K_s + C}\right) \quad \text{(Equation 8)}$$

whereas, $A_{Tissue}$ amount of MEDI-546 in the peripheral tissue compartment;

C=concentration of the free (unbound MEDI-546) in the central compartment;

$C_{tot}$=total (free and bound) MEDI-546 in the central compartment;

RC=concentration of the drug-receptor complex (Ab·R);

$R_{tot}$=concentration of the total (free and bound) receptors, R+Ab·R;

$k_{el}$=first-order elimination constant;

$k_{int}$=internalization (elimination of the complex) rate constant;

$k_{deg}$=degradation (elimination of the free receptor) rate constant;

$k_{syn}$=receptor production rate;
$k_{on}$=binding rate constant;
$k_{off}$=dissociation rate constant;
$K_s$=steady-state rate constant;
$k_{SerumTissue}$, $k_{TissueSerum}$=rate constant for inter-compartmental transfer between central serum compartment and peripheral tissue compartment;
Input=intravenous infusion rate; and,
V=central distribution volume of MEDI-546.

Change of free drug concentrations in central and peripheral compartments over time was expressed by Equations 6 and 7. Equation 8 expressed the change of total receptor concentration over time in terms of free drug and $R_{tot}$.

To avoid model over-parameterization, rate constants $k_{deg}$ and $k_{int}$ were assumed the same and fixed to a value experimentally determined by confocal imaging studies.

The initial conditions for each compartment were as follows:

$$C(0)=D/V;$$

$$A_{Tissue}(0)=0;$$

$$RC(0)=0;$$

$$R(0)=k_{syn}/k_{deg}; \text{ and,}$$

$$GS(0)=k_{in}/k_{out}$$

For translational simulation purposes an additional compartment representing the skin tissues was included in the PK-PD model (FIG. 4). The partitioning of MEDI-546 to the skin compartment was described by the following equation:

$$\frac{dC_{skin}}{dt} = k_{bs} \cdot C - k_{sb} \cdot C_{skin} \quad \text{(Equation 9)}$$

The partitioning of MEDI-546 from the central compartment to skin was characterized by a skin-to-blood rate constant ($k_{sb}$) of 0.27 $d^{-1}$, which corresponds to the estimated absorption rate of CAT-354, a monoclonal antibody against IL-13, in healthy volunteers (Oh et al., Br. J. Clin. Pharmacol. 69:645-655 (2010)), and a distribution rate constant (blood to skin, $k_{bs}$) of 0.25·$k_{sb}$. The $k_{bs}$ rate constant was scaled to reflect a 0.25 skin:serum MEDI-546 concentration ratio at equilibrium. In this model, no mass loss in the central compartment was assumed due to MEDI-546 partitioning to the skin.

MEDI-546 blocked the interaction of interferons with IFNAR1 and inhibited the production of type I IFN genes ($k_{in}$) according to the formula:

$$\frac{dGS}{dt} = k_{in} * \left(1 - \frac{I_{max} * C_1}{IC50 + C_1}\right) - k_{out} * GS$$

where:
GS=Type I IFN gene signature score;
$I_{max}$=Maximum fractional extent of inhibition;
$IC_{50}$=Potency, MEDI-546 concentration corresponding to half-maximum inhibition of GS production;
$k_{in}$=Endogenous GS production rate; and,
$k_{out}$=GS elimination rate constant.

The initial condition at time zero for the PD compartment (GS in peripheral blood) was GS(0)=$k_{in}/k_{out}$.

To simulate the type I IFN GS response in skin tissues, it was assumed that type I IFN genes were locally produced and suppressed by MEDI-546 in a similar manner. The production rate of skin IFN gene signature ($k_{in,skin}$) was adjusted to reflect a baseline value lower than or equal to the type I IFN GS in whole blood.

Population PK-PD Modeling of MEDI-546 in SSc Patients.

Data analysis was performed using a pharmacostatistical software package NONMEM (Version 7.1, ICON Development Solutions, Elliott City, Md.). The model development was based on the NONMEM objective function value (−2 times the log of the likelihood) and the randomness of weighted residuals. The first-order conditional estimation with interaction (FOCEI) method was used for model development.

The total dose that each subject received (mg) was calculated according to the weight-based dosage (mg/kg) and recorded body weight of that subject. Interindividual variability was modeled as a multiplicative random effect: θ·exp(η), where θ represented a typical value of a structural parameter and η was an individual-specific normally distributed random effect. The residual variability was modeled as:

$$Y=F+F*\epsilon_{proportional}+\epsilon_{additive},$$

where Y was a PK or PD observation and F was the corresponding model predicted value.

The residual error $\epsilon$ was assumed to be normally distributed with mean 0 and unknown variances to be estimated. An exploratory covariate analysis was performed to evaluate the effects of body weight on $CL_{res}$ and $V_c$. Both parameters were allometrically scaled to a typical body weight of 70 kg, (body weight/70)$^\theta$, where θ represented the power coefficient.

Model stability and performance were assessed by a visual predictive check procedure (Holford, in 14th meeting of the Population Approach Group in Europe. (Pamplona, Spain, 2005)) and bootstrap resampling technique (Ette, J. Clin. Pharmacol. 37:486-495 (1997)) using the PsN-Toolkit (Lindbom et al., Comput Methods Programs Biomed. 79:241-257 (2005)). For VPC, the final fixed- and random-effect model parameters, along with original dataset as the simulation template, were used to generate the 90% intervals of 1,000 simulated profiles. Median, 5th, 10th, 90th, and 95th percentiles of the simulated concentrations at each time point were calculated and plotted.

Graphical comparison was made between the observed data and prediction intervals derived from the simulated profiles. The bootstrap resampling technique was used to validate parameter estimates. This model evaluation consisted of repeatedly fitting the model to 1,000 bootstrap replicates of the dataset. The datasets were replicated by randomly sampling the patient data with replacement up to the total number of patients in the original dataset. The median of the 1,000 parameter estimates was compared with the estimates obtained with the original dataset. The 95% confidence interval (CI) of each parameter was computed as the 2.5 to 97.5 percentile range of the bootstrapped parameter estimates.

Stochastic Simulations for MEDI-546 in SLE Patients

The PK-PD model developed for SSc was subsequently used to simulate type I IFN GS and target modulation profiles in SLE patients upon multiple MEDI-546 administrations. An additional compartment representing the skin tissue was added to the PK-PD model. It was assumed that PK of MEDI-546 in patients with SLE was the same as in SSc patients. The production rate (kin) of IFN-related GS score was increased for SLE patients to reflect a higher baseline value than in SSc patients. Stochastic simulations were performed using resampled actual observed baseline GS scores and body weight of patients with SLE enrolled in a prior clinical study for an anti-IFNα mAb (Higgs et al., Ann. Rheum. Dis. 70:2029-2036 (2011); Yao et al., Arthritis Rheum. 60:1785-1796 (2009); Yao et al., PLoS One 3:e2737 (2008); Yao et al., Hum. Genomics Proteomics 2009:374312 (2009); Yao et al., Arthritis Res. Ther. 12 (Suppl 1):S6 (2010); Merrill et al., Ann. Rheum. Dis. 70:1905-1913 (2011)). To simulate skin tissue GS scores, the partition of the MEDI-546 from serum to tissues was assumed to be 25% (Paquet et al., Exp. Dermatol. 15:381-386 (2006)).

Example 1

Type I IFN Signature as a PD Marker

A composite PD biomarker was developed using a five gene type I IFN GS shared by SLE and SSc, both in blood and in disease tissue (skin). The five gene type I IFN GS is a reliable surrogate of type I IFN activity in the blood as well as a correlate with baseline disease activity in SLE and SSc. There is also a strong concordance in this GS score between blood and skin specimens from SLE or SSc patients (Higgs et al., Ann. Rheum. Dis. 70:2029-2036 (2011), allowing the use of this type I IFN signature in blood as a PD biomarker to measure pharmacological effect of MEDI-546.

The five type I IFN-inducible genes (IFI27, IFI44, IFI44L, RSAD2, and IFI6) used to measure the PD of MEDI-546 are a subset of the 21 genes used as PD markers for sifalimumab, an anti-IFN-α mAb therapy in SLE described previously (Yao et al., Arthritis Rheum. 60:1785-1796 (2009); Yao et al., Hum. Genomics Proteomics 2009: 374312 (2009); Yao et al., Arthritis Res. Ther. 12 (Suppl 1):S6 (2010)). These 21 genes are: IFI6 (interferon, alpha inducible protein 6), RSAD2 (radical S-adenosyl methionine domain containing 2), IFI44 (interferon-induced protein 44), IFI44L (interferon induced protein 44, like), IFI27 (interferon alpha inducible protein 27), MX1 (myxovirus (influenza virus) resistance 1, interferon-inducible protein p78), IFIT1 (interferon-induced protein with tetratricopeptide repeats 1), HERC5 (hect domain and RLD 5), ISG15 (ISG15 ubiquitin-like modifier), LAMP3 (lysosomal-associated membrane protein 3), OAS3 (2'-5'-oligoadenylate synthetase 3, 100 kDa), OAS1 (2'-5'-oligoadenylate synthetase 1, 40/60 kDa), EPSTI1 (epithelial stromal interaction 1 (breast)), IFIT3 (interferon-induced protein with tetratricopeptide repeats 3), LY6E (lymphocyte antigen 6 complex, locus E), OAS2 (2'-5'-oligoadenylate synthetase 2, 69/71 kDa), PLSCR1 (phospholipid scramblase 1), SIGLEC1 (sialic acid binding Ig-like lectin 1, sialoadhesin), USP18 (ubiquitin specific peptidase 18), RTP4 (receptor (chemosensory) transporter protein 4), and DNAPTP6 (DNA polymerase-transactivated protein 6) (see PCT Publ. No. WO 2008/070137, which is incorporated herein by reference in its entirety).

The 21 type I IFN gene signature (GS) was shown to be neutralized in a dose-dependent manner following treatment with sifalimumab in mild-to-moderate SLE patients in a Phase 1a clinical trial (Yao et al., Arthritis Rheum. 60:1785-1796 (2009); Merrill et al., Ann. Rheum. Dis. 70:1905-1913 (2011)). There was a strong correlation between the five and 21 gene type I IFN gene signatures in SLE (Higgs et al., Ann. Rheum. Dis. 70:2029-2036 (2011)). While both type I IFN gene signatures were suitable PD markers for MEDI-546 in SLE, the five gene PD markers were used in the MEDI-546 trial in SSc.

Briefly, the five genes in the type I IFN GS were selected based on three primary criteria:
(1) prevalence and magnitude of over-expression in SSc and SLE patients compared to healthy controls;
(2) ability to be induced in whole blood from healthy donors ex vivo by type I IFN; and,
(3) the ability to be substantially suppressed by MEDI-546 ex vivo in healthy donor peripheral blood mononuclear cells after stimulation by SLE serum (Yao et al., Hum. Genomics Proteomics 2009:374312 (2009)).

The magnitude of overexpression of the type I IFN GS score in blood and lesional skin of SLE and SSc patients was calculated by the expression level of the five genes described (statistically significant in all cases) (FIG. 1). Baseline levels of the type I IFN GS score were concordant between blood and lesional skin in both SSc and SLE patients (see, e.g., Higgs et al., Ann. Rheum. Dis. 70:2029-2036 (2011)).

Example 2

MEDI-546 Completely Suppressed the Type I IFN Signature in SSc Patients in a Dose-dependent Manner The type I IFN GS described above was used in a FTIH study for MEDI-546 in SSc. Besides observing a dosing dependent PD effect, this study showed for the first time that an antibody that targets the type I IFN signaling pathway had the ability to normalize the type I IFN signature in both blood and disease tissue in a disease where type I IFN might play a role in the disease pathogenesis. Furthermore, for several SSc patients that had comparable level of the type I IFN signature with that in SLE, a near complete suppression of the type I IFN signature (duration of suppression varied in response to difference in dosing) was observed following MEDI-546 treatment.

TABLE 4, supra, shows the summaries of baseline demographic and type I IFN GS status as determined by type I IFN GS score for SSc patients enrolled in the FTIH study (MI-CP180) before they received MEDI-546 treatment ($GS_0$; baseline; pretreatment). The cutoffs for type I IFN GS positivity in blood and skin of SSc patients were $GS_0 > 2.9$ and $GS_0 > 1.8$, respectively. These type I IFN GS thresholds represented the upper boundary of mean±2 standard deviations of the distribution of the type I IFN GS in the blood and skin of 54 and 30 healthy donors (1.2±1.7 in blood, 1.0±0.8 in skin; FIG. 1). The median observed type I IFN GS score for each single- or multiple-dose cohort was calculated and plotted across time for all SSc patients that were positive for type I IFN GS score at baseline in both blood and skin (FIG. 2). Those dose cohorts with type I IFN GS modulated to or below values of mean for blood and skin in healthy donors respectively during the study period achieved complete suppression of the type I IFN GS.

Durable and nearly complete modulation of the type I IFN GS in SSc patients was observed in blood in three high exposure cohorts: 20.0 mg/kg single dose, 1.0 mg/kg and 5.0 mg/kg multiple doses. Complete suppression of type I IFN GS in skin was observed in two cohorts: 20.0 mg/kg single dose and 1.0 mg/kg multiple doses. The 5.0 mg/kg multi-dose cohort contained only a single $GS_0$ positive patient. The small sample size in this cohort likely was not able to provide an accurate evaluation of the PD effect, although the percentage of type I IFN GS suppression represented in FIG. 2D for this patient was consistent with the overall trend.

The minimum type I IFN GS score among this pool of healthy controls shown as the dashed line (FIGS. 2A and 2B)

indicated the lowest boundary of type I IFN GS values in the healthy control population, of which no type I IFN GS positive patients in the MEDI-546 treated cohort went below. Overall, a dose-dependent target modulation (see Methods, supra) of the type I IFN GS with MEDI-546 (i.e., PD effect) in SSc patients was observed in both whole blood and skin.

With the exception of the 0.3 mg/kg (both single and multi-dose) cohorts, a normalization of the type I IFN GS up to two weeks was observed in blood in all other cohorts. As mentioned above, the three highest exposure dose cohorts provided more durable PD effect. It should be noted that several SSc patients in the trial had high baseline type I IFN GS that is comparable to that of SLE patients. A near complete target modulation following MEDI-546 treatment was observed in these patients following initial dosing, and the duration of response varied based on dosing schedules (FIG. 7).

Example 3

Receptor Internalization Kinetics

Kinetics of MEDI-546 internalization in IFNAR1 expressing THP-1 cells was assessed quantitatively using live-cell confocal fluorescent imaging technology (FIG. 3). Fluorescently labeled MEDI-546 (MEDI-546-Alexa647) bound to THP-1 cells, while no binding of IgG-Alexa647, the isotype control of MEDI-546, was observed. This result demonstrated specific binding to THP-1 cells by MEDI-546 (FIG. 8). The translocation of MEDI-546-Alexa647 from the cell surface to the cytoplasm was monitored over time using a confocal fluorescent imager. Overlays of fluorescence images for cytoplasm (CFSE) and antibody (Alexa647) signals prior to and after the internalization of MEDI-546-Alexa647 are shown in FIGS. 3A and 3B, respectively.

While initially MEDI-546-associated fluorescence was predominantly localized on the cell surface (FIG. 3A), at 40 min, MEDI-546-Alexa647 signals were seen in punctuated spots located in the cytoplasm (FIG. 3B). Kinetic images recorded over the time course were analyzed using a quantitative algorithm. A time course of MEDI-546-Alexa647 internalization into cytoplasm was constructed from the data obtained from four independent experiments (FIG. 3C). The internalization half-life was estimated to be 12.9±1.2 (standard deviations) minutes.

Example 4

Population PK-PD Modeling of MEDI-546 in SSc Patients

The PD biomarker data and the target receptor internalization kinetics as determined from confocal imaging studies, along with prior knowledge from a previous clinical study evaluating an anti-IFN-α mAb in SLE (Yao et al., Arthritis Rheum. 60:1785-1796 (2009); Merrill et al., Ann. Rheum. Dis. 70:1905-1913 (2011)) were integrated into a PK-PD model for the population analysis of MEDI-546 SSc data and stochastic simulations for SLE.

A mechanistic PK-PD model for MEDI-546 was generated (see FIG. 4). According to this model, following intravenous (IV) administration, MEDI-546 (Ab) bound to IFNAR1 (R) and the antibody-receptor complex was subsequently internalized and degraded ($k_{int}$) inside the cells. The PD of MEDI-546 (type I IFN GS score) was best described by an indirect response model, in which the type I IFN-inducible gene production ($k_{in}$) was inhibited by MEDI-546. A total of 202 quantifiable PK observations from all 34 patients receiving MEDI-546 and 147 type I IFN GS score observations in peripheral blood from 22 type I IFN GS positive patients were included in the modeling dataset. Four outlier PD observations from different patients, identified during the model development with exaggerated weight residual values (absolute value greater than 5), were excluded from the final analysis.

The estimated PK-PD structural and variance parameters are summarized in TABLE 5.

TABLE 5

Summary of estimated population PK-PD parameters, interindividual and residual error variance of MEDI-546 in SSc patients following single IV administration.

| Parameter | Original Estimates (RSE, %)[a] | Bootstrap (n = 1,000) Median | 95% CI |
|---|---|---|---|
| Fixed effect | | | |
| $CL_{RES}$ (L/d) | 0.198 (14) | 0.192 | 0.141-0.234 |
| $V_c$ (L) | 3.46 (8.3) | 3.46 | 3.19-3.83 |
| Q (L/d) | 0.926 (16) | 0.919 | 0.327-1.18 |
| $V_p$ (L) | 2.52 (18) | 2.54 | 2.18-3.24 |
| $K_{ss}$ (nM) | 1.17 (16) | 1.30 | 0.555-3.08 |
| $R_0$ (nM) | 0.0882 (10) | 0.0907 | 0.0758-0.107 |
| $k_{int}$ (d$^{-1}$) | 77.4 Fixed (NA) | N.E. | N.E. |
| $I_{max}$ | 0.939 (1.3) | 0.938 | 0.920-0.966 |
| $IC_{50}$ (nM) | 0.978 (52) | 0.772 | 0.248-1.96 |
| $GS_0$ | 7.30 (21) | 7.66 | 5.96-10.1 |
| $k_{GS}$ (d$^{-1}$) | 1.92 (9.4) | 2.00 | 1.65-2.57 |
| $GS_{FLOOR}$ | 0.764 (4.4) | 0.746 | 0.521-0.874 |
| Interindividual variability [b] | | | |
| $\eta_{CLRES}$ | 29.1 (23) | 27.8 | 12.6-64.0 |
| $\eta_{Vc}$ | 19.6 (16) | 18.7 | 12.6-24.4 |
| $\eta_{R0}$ | 18.9 (28) | 17.6 | 7.21-39.5 |
| $\eta_{IC50}$ | 93.8 (48) | 98.6 | 85.5-270 |
| $\eta_{GS0}$ | 55.8 (3.6) | 51.2 | 29.8-58.6 |
| Residual variability | | | |
| PK proportional error (% CV) | 15.6 (12) | 15.2 | 11.4-18.3 |
| PK additive error (SD, µg/mL) | 0.0263 SD (10) | 0.0257 | 0.0023-0.0305 |
| PD proportional error (% CV) | 40.5 (4.5) | 39.0 | 32.7-46.8 |

[a] Relative standard error of the parameter estimate
[b] Expressed as percent coefficient of variation (CV %).
NA = not available; and N.E. = not estimated.

The parameters included in the table are: $CL_{RES}$=MEDI-546 clearance corresponding to the first-order elimination pathway; $V_c$=central distribution volume; Q=inter-compartmental clearance corresponding to the transfer of mavrilimumab between central serum compartment and peripheral tissue compartment; $V_p$=peripheral distribution volume; $K_{ss}$=steady-state constant, apparent equilibrium dissociation constant; $R_0$=baseline IFNAR1 level; $k_{int}$=internalization rate constant; $I_{max}$=maximum fractional extent of inhibition; $IC_{50}$=Potency, MEDI-546 concentration corresponding to half-maximum inhibition of GS production; $GS_0$=baseline type I IFN GS; $k_{GS}$=GS elimination (degradation) rate constant; and $GS_{FLOOR}$=theoretical lower limit of GS measurement.

The first-order clearance ($CL_{RES}$, 0.198 L/d) was close to that of an endogenous IgG not subject to the antigen-sink effect. The central distribution volume ($V_c$, 3.46 L) was slightly greater than the serum volume in humans, while the smaller peripheral distribution volume ($V_p$, 2.52 L) suggested restricted extravascular distribution of MEDI-546, as expected for a monoclonal antibody. The internalization rate of the MEDI-546/IFNAR1 complex ($k_{int}$) was fixed to a value determined from in vitro confocal imaging experiments. The population baseline type I IFN GS in peripheral blood, $GS_0$, was 7.30 with an $IC_{50}$ (potency) of 0.978 nM. The elimination constant of type I IFN GS score ($k_{out}$) was 1.92 $d^{-1}$, corresponding to a half-life of 8.7 hours for IFNAR-associated mRNAs in whole blood. The floor parameter $f_{Gs}$ (0.764) represented the theoretical analytical lower boundary of the PD assay.

Interindividual PK variability was moderate in SSc patients following IV administration. Both $CL_{RES}$ and $V_c$ increased with body weight. From a pharmacostatistical assessment, the covariate effect of weight on PK was not significantly different from the typical value for IgG, thus in the final PK model, the exponents corresponding to the body weight effect were fixed to the default values of 0.75 ($CL_{RES}$) and 1.0 ($V_c$). When body weight effect was incorporated, interindividual variability decreased from 54.1% to 29.1% for $CL_{RES}$, and from 35.1% to 19.6% for $V_c$. The estimated variance of proportional error for MEDI-546 concentrations was 0.0242, which corresponds to an assay precision of 15.6% CV. The estimated standard error of the additive residual component was 0.0263 µg/mL, close to the assay lower limit of quantitation (0.02 µg/mL).

Comparing with MEDI-546 PK, the type I IFN GS data was more variable. The interindividual variability (% CV) was 93.8% for IC50 and 55.8% for baseline GS score. The estimated proportional residual error for the PD assay was 40.5% CV.

The PK and PD profiles from four representative patients (two from the single-dose cohorts and two from the multiple-dose cohorts) are presented in FIG. 5. The solid circles represent PK or type I IFN GS scores observed in peripheral blood, while the solid lines represent the population (gray line) and individual (black line) model predictions, respectively. All the observed and model-predicted individual PK and PD profiles are shown in FIGS. 9A, 9B, 10A and 10B. Target modulation was calculated from model-predicted type I IFN GS scores, and compared with the observed values (FIGS. 11A and 11B). Doses greater than or equal to 1.0 mg/kg achieved complete target modulation in SSc patients. The duration of target modulation response was dose-dependent: higher doses prolonged the duration of complete target modulation.

The performance of the PK-PD model was evaluated by visual predictive check, in which the observations were overlaid with the simulated profiles from 1,000 replicates (FIGS. 12 and 13). Most observations centered around the medians of the simulated profiles and were encapsulated within the 5th and 95th percentiles, demonstrating that the pharmacostatistical model sufficiently captured the PK and PD properties of MEDI-546 and interindividual variabilities In the MI-CP180 clinical trial skin biopsies were only collected pre-dose and at one time point post dosing (Day 7 for single-dose cohorts and Day 28 for multiple-dose cohorts). Given the limited information of the type I IFN signature in skin, its GS scores were not modeled for this Phase 1 study in SSc patients. These data were used to assess the utility of the PK-PD model in predicting the GS response in skin tissues after MEDI-546 treatment. The skin GS predictions were made by assuming a 25% tissue:serum ratio distribution of IgG (Paquet et al., Exp. Dermatol. 15:381-386 (2006)) and a skin-to-blood rate constant of 0.27 $d^{-1}$, which is typical for the absorption of subcutaneously administered IgG from the dosing site (Oh et al., Br. J. Clin. Pharmacol. 69:645-655 (2010)).

In patients with toxic epidermal necrolysis the median IgG concentration in cutaneous blister fluid was approximately 24% of that in serum (Paquet et al., Exp. Dermatol. 15:381-386 (2006)). The subcutaneous absorption rate of an IgG was well characterized in a Phase 1 study in heathy volunteers with intensive PK sampling schedule (Oh et al., Br. J. Clin. Pharmacol. 69:645-655 (2010)). When both assumptions were incorporated in the mechanistic model, the trend and magnitude of observed skin GS response in SSc patients after MEDI-546 administration were adequately captured by the model.

No regression or curve-fitting was conducted, and the primary interest was to evaluae whether the PK-PD model sufficiently captured the trend and range of the type I GS response in skin tissues (FIG. 14).

Although the baseline skin GS data were highly variable, following MEDI-546 treatment the simulated type I GS in skin were close to the actual observations, especially for doses ≥1 mg/kg, for SSc patients. One subject in Cohort 2 (0.3 mg/kg, SID=2) had a relatively high baseline type I IFN GS in peripheral blood, resulting in a higher projected skin type I IFN GS score in this subject. The trend and extent of skin type I IFN GS responses in SSc patients following MEDI-546 administration were adequately projected by the PK-PD model, especially for doses ≥1 mg/kg (SID≥6). This provided additional evidence of the applicability of the PK-PD model to simulate and predict the skin IFN GS response in SLE patients upon multiple MEDI-546 administrations. Accordingly, the pharmacostatistical model was subsequently used to simulate the PK and PD profiles of MEDI-546 in SLE. In healthy donors (n=30) the observed upper boundary (mean+2 standard deviations) of type I IFN GS was 1.8 in skin.

The antigen of MEDI-546 is a cell-membrane associated receptor (IFNAR1), which is widely expressed on most nucleated cells. From in vitro confocal imaging studies, upon MEDI-546 binding to IFNAR1 the antibody-receptor complex was rapidly internalized with a typical half-life of 12.9 minutes (FIG. 3). Therefore the PK of MEDI-546 was subject to the target-receptor mediated clearance, or the antigen-sink effect (more rapid drug clearance at lower concentration levels). The estimated distribution volumes and the first-order clearance by the reticuloendothelial system were typical for IgG not subject to the antigen sink effect (Oh et al., Br. J. Clin. Pharmacol. 69:645-655 (2010); Tabrizi et al., Inflamm. Allergy Drug Targets 9:229-237 (2010)).

Despite the small sample size of this Phase 1 study, both $CL_{RES}$ and Vc were found to increase with body weight as observed with other IgGs. The systemic expression level of IFNAR1 in SSc patients was 88 pM. Overall the model appeared robust as the PK parameter estimates were close to the median of bootstrap replicates shown in TABLE 5.

Example 5

Stochastic Simulations for SLE Patients

To support the program transition from a FTIH study in SSc patients to a large Proof-of-Concept (PoC) study in SLE, we used translational simulations to bridge across the two patient populations in lieu of an additional Phase 1 trial in SLE. The recorded SLE patient body weight and baseline type I IFN GS from a clinical study of sifalimumab were used as the basis for a simulation of type I IFN GS responses in virtual SLE patients upon multiple MEDI-546 administrations.

To ease the dose preparation and reduce theoretical dosing error for the PoC study in SLE patients, MEDI-546 dosing was switched from weight-based (mg/kg) to fixed-dose (mg) based on translational simulations. Although from stochastic simulations a 300 mg monthly fixed-dose could maintain the suppression of peripheral-blood GS to the normal level (≤2.9) in a typical SLE subject (FIG. 6A, median), a higher dose (1000 mg) was also recommended for the PoC trial to ensure adequate drug exposure and GS suppression in skin especially for SLE patients with substantially elevated type I IFN GS at baseline.

In addition, the 1000 mg dose would insure against potential divergence of the SLE simulation assumptions (e.g., the potency and efficacy of MEDI-546 in SLE could be different from in SSc). Suboptimal doses lower than 300 mg were not recommended for the PoC trial, as it would be unlikely for SLE patients to receive much MEDI-546 treatment benefits assuming that substantial target modulation is essential for observing clinical benefit. On the other hand, the improvement in efficacy was predicted to be incremental at doses greater than 1000 mg. Based on above considerations, both 300 and 1000 mg monthly doses were recommended for the PoC trial in SLE.

Accordingly, the modulation of the type I IFN GS in whole blood (FIG. 6A) and skin tissues (FIG. 6B) were simulated in virtual SLE patients (n=1,200 for each dose) following repeated every-four-week IV administrations of MEDI-546 at 300- or 1,000-mg fixed dose level.

The virtual SLE patients were generated by repetitive sampling from recorded type I IFN GS at baseline and body weight of SLE patients previously enrolled in a study for sifalimumab, an anti-IFNα mAb. The median baseline whole blood GS score was 37 in SLE patients ($GS_0$ range: 3 to 86; FIG. 1). The median body weight of SLE patients was 74 kg, with a range of 39.4 to 141 kg. FIGS. 6A and 6B show the median (solid line), lower and upper quartiles (dotted lines) of simulated type I IFN GS responses in these patients.

According to the simulations, the whole-blood type I IFN GS scores in SLE patients could be neutralized to the range of 1 to 5 (median 2 to 3) with monthly MEDI-546 dosing. This represented approximately 94% suppression of the type I IFN signature from the baseline level at steady-state of MEDI-546 treatment. The higher dose (1,000 mg) would allow for increased MEDI-546 tissue exposure, resulting in more substantial type I IFN GS suppression in skin tissues than the lower dose (300 mg). In addition, the simulated type I IFN GS responses in both whole blood and skin tissues fluctuated with the 300 mg monthly dose administration, while remaining relatively flat for the 1000 mg dose during the treatment period.

More SLE patients were simulated (n=12,000 for each dose level) for the calculation of overall target modulation after 6 months of MEDI-546 treatment. In peripheral blood, type I IFN GS was suppressed to the level of that of healthy normal patients (2.9, the upper boundary of mean±2 standard deviations from 54 normal controls as described above) in 68% of the simulated SLE patients dosed at 1000 mg (53% at 300 mg level). In skin tissues the projected percentage of SLE patients with over 90% IFN GS suppression were 20% and 30% for the 300 and 1000 mg dose levels, respectively.

Example 6

Treatment of SLE, Myositis, and Lupus Nephritis Patients with Fixed Dosage Regimens Determined Using Translational Simulations Translational simulations are used to identify effective dosages and to design dosage regimens to treat SLE, myositis or lupus nephritis patients based on SSc clinical data. Type I IFN GS signatures are identified that are common to SSc and SLE, SSc and myositis, or SSc and lupus nephritis. PK/PD models based on SSc data are generated as described above and adjusted based on PK/PD data corresponding to SLE, myositis, or lupus nephritis. Stochastic simulations on virtual patients are conducted on the adjusted SSc/SLE, SSc/myositis, or SSc/lupus nephritis PK/PD models.

Fixed doses predicted to suppress the type I IFN GS in the virtual patients are identified through the simulations. The fixed dose amounts of therapeutic agents identified in the simulations are administered to actual SLE, myositis, or lupus nephritis patients. The administration of the fixed dose of therapeutic agent effectively suppresses the type I IFN GS in the actual patients and effectively treats SLE, myositis, or lupus nephritis.

The foregoing description of the specific aspects will so fully reveal the general nature of the disclosure that others can, by applying knowledge within the skill of the art, readily modify and/or adapt for various applications such specific aspects, without undue experimentation, without departing from the general concepts provided. Therefore, such adaptations and modifications are intended to be within the meaning and range of equivalents of the disclosed aspects, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary aspects, but should be defined only in accordance with the following claims and their equivalents.

What is claimed is:

1. A method of treating an adult patient having a systemic lupus erythematosus (SLE) comprising intravenously administering monthly to the adult patient a fixed dose comprising 300 mg or 1000 mg of an antibody or antigen-binding fragment thereof comprising the amino acid sequences of SEQ ID NO: 1 and SEQ ID No: 2.

* * * * *

UNITED STATES PATENT AND TRADEMARK OFFICE
CERTIFICATE OF CORRECTION

PATENT NO. : 9,493,570 B2  
APPLICATION NO. : 14/407156  
DATED : November 15, 2016  
INVENTOR(S) : Higgs et al.

Page 1 of 1

It is certified that error appears in the above-identified patent and that said Letters Patent is hereby corrected as shown below:

In the Specification

In particular, SEQ ID NO: 1 in Table 1 at Column 18, should read:
--EVQLVQSGAEVKKPGESLKISCKGSGYIFTNYWIAWVRQMPGKGLESMGIIYPGDSDIRY
SPSFQGQVTISADKSITTAYLQWSSLKASDTAMYYCARHDIEGFDYWGRGTLVTVSS--.

Additionally, SEQ ID NO: 1 in the Sequence Listing at Column 61, should read as follows:
```
    Glu Val Gln Leu Val Gln Ser Gly Ala Glu Val Lys Lys Pro Gly Glu
     1               5                  10                  15
    Ser Leu Lys Ile Ser Cys Lys Gly Ser Gly Tyr Ile Phe Thr Asn Tyr
                    20                  25                  30
    Trp Ile Ala Trp Val Arg Gln Met Pro Gly Lys Gly Leu Glu Ser Met
                35                  40                  45
    Gly Ile Ile Tyr Pro Gly Asp Ser Asp Ile Arg Tyr Ser Pro Ser Phe
            50                  55                  60
    Gln Gly Gln Val Thr Ile Ser Ala Asp Lys Ser Ile Thr Thr Ala Tyr
     65                  70                  75                  80
    Leu Gln Trp Ser Ser Leu Lys Ala Ser Asp Thr Ala Met Tyr Tyr Cys
                    85                  90                  95
    Ala Arg His Asp Ile Glu Gly Phe Asp Tyr Trp Gly Arg Gly Thr Leu
                    100                 105                 110
    Val Thr Val Ser Ser
                    115
 --                                                                --.
```

Signed and Sealed this  
First Day of March, 2022

Drew Hirshfeld  
*Performing the Functions and Duties of the*  
*Under Secretary of Commerce for Intellectual Property and*  
*Director of the United States Patent and Trademark Office*

SEQUENCE LISTING

<160> NUMBER OF SEQ ID NOS: 23

<210> SEQ ID NO 1
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ile Phe Thr Asn Tyr
            20                  25                  30

Trp Ile Ala Trp Val Arg Gln Met Pro Gly Lys Cys Leu Glu Ser Met
        35                  40                  45

Gly Ile Ile Tyr Pro Gly Asp Ser Asp Ile Arg Tyr Ser Pro Ser Phe
    50                  55                  60

Gln Gly Gln Val Thr Ile Ser Ala Asp Lys Ser Ile Thr Thr Ala Tyr
65                  70                  75                  80

Leu Gln Trp Ser Ser Leu Lys Ala Ser Asp Thr Ala Met Tyr Tyr Cys
                85                  90                  95

Ala Arg His Asp Ile Glu Gly Phe Asp Tyr Trp Gly Arg Gly Thr Leu
            100                 105                 110

Val Thr Val Ser Ser
            115

<210> SEQ ID NO 2
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Phe Phe Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Leu Ser
    50                  55                  60

Gly Ser Gly Ser Gly Thr Asp Phe Thr Leu Thr Ile Thr Arg Leu Glu
65                  70                  75                  80

Pro Glu Asp Phe Ala Val Tyr Tyr Cys Gln Gln Tyr Asp Ser Ser Ala
                85                  90                  95

Ile Thr Phe Gly Gln Gly Thr Arg Leu Glu Ile Lys
            100                 105

<210> SEQ ID NO 3
<211> LENGTH: 119
<212> TYPE: PRT
<213> ORGANISM: Homo sapiens

<400> SEQUENCE: 3

Met Glu Ala Ser Ala Leu Thr Ser Ser Ala Val Thr Ser Val Ala Lys
1               5                   10                  15

Val Val Arg Val Ala Ser Gly Ser Ala Val Val Leu Pro Leu Ala Arg
            20                  25                  30

Ile Ala Thr Val Val Ile Gly Gly Val Val Ala Val Pro Met Val Leu
        35                  40                  45

Ser Ala Met Gly Phe Thr Ala Ala Gly Ile Ala Ser Ser Ser Ile Ala
    50                  55                  60

Ala Lys Met Met Ser Ala Ala Ala Ile Ala Asn Gly Gly Gly Val Ala

```
                65                  70                  75                  80
Ser Gly Ser Leu Val Ala Thr Leu Gln Ser Leu Gly Ala Thr Gly Leu
                85                  90                  95

Ser Gly Leu Thr Lys Phe Ile Leu Gly Ser Ile Gly Ser Ala Ile Ala
                100                 105                 110

Ala Val Ile Ala Arg Phe Tyr
        115

<210> SEQ ID NO 4
<211> LENGTH: 444
<212> TYPE: PRT
<213> ORGANISM: Homo sapiens

<400> SEQUENCE: 4

Met Ala Val Thr Thr Arg Leu Thr Trp Leu His Glu Lys Ile Leu Gln
1               5                   10                  15

Asn His Phe Gly Gly Lys Arg Leu Ser Leu Leu Tyr Lys Gly Ser Val
                20                  25                  30

His Gly Phe Arg Asn Gly Val Leu Leu Asp Arg Cys Cys Asn Gln Gly
            35                  40                  45

Pro Thr Leu Thr Val Ile Tyr Ser Glu Asp His Ile Ile Gly Ala Tyr
    50                  55                  60

Ala Glu Glu Ser Tyr Gln Glu Gly Lys Tyr Ala Ser Ile Ile Leu Phe
65                  70                  75                  80

Ala Leu Gln Asp Thr Lys Ile Ser Glu Trp Lys Leu Gly Leu Cys Thr
                85                  90                  95

Pro Glu Thr Leu Phe Cys Cys Asp Val Thr Lys Tyr Asn Ser Pro Thr
                100                 105                 110

Asn Phe Gln Ile Asp Gly Arg Asn Arg Lys Val Ile Met Asp Leu Lys
            115                 120                 125

Thr Met Glu Asn Leu Gly Leu Ala Gln Asn Cys Thr Ile Ser Ile Gln
    130                 135                 140

Asp Tyr Glu Val Phe Arg Cys Glu Asp Ser Leu Asp Glu Arg Lys Ile
145                 150                 155                 160

Lys Gly Val Ile Glu Leu Arg Lys Ser Leu Leu Ser Ala Leu Arg Thr
                165                 170                 175

Tyr Glu Pro Tyr Gly Ser Leu Val Gln Gln Ile Arg Ile Leu Leu Leu
                180                 185                 190

Gly Pro Ile Gly Ala Gly Lys Ser Ser Phe Phe Asn Ser Val Arg Ser
            195                 200                 205

Val Phe Gln Gly His Val Thr His Gln Ala Leu Val Gly Thr Asn Thr
    210                 215                 220

Thr Gly Ile Ser Glu Lys Tyr Arg Thr Tyr Ser Ile Arg Asp Gly Lys
225                 230                 235                 240

Asp Gly Lys Tyr Leu Pro Phe Ile Leu Cys Asp Ser Leu Gly Leu Ser
                245                 250                 255

Glu Lys Glu Gly Gly Leu Cys Arg Asp Asp Ile Phe Tyr Ile Leu Asn
                260                 265                 270

Gly Asn Ile Arg Asp Arg Tyr Gln Phe Asn Pro Met Glu Ser Ile Lys
            275                 280                 285

Leu Asn His His Asp Tyr Ile Asp Ser Pro Ser Leu Lys Asp Arg Ile
    290                 295                 300

His Cys Val Ala Phe Val Phe Asp Ala Ser Ser Ile Gln Tyr Phe Ser
305                 310                 315                 320
```

```
Ser Gln Met Ile Val Lys Ile Lys Arg Ile Arg Arg Glu Leu Val Asn
                325                 330                 335

Ala Gly Val Val His Val Ala Leu Leu Thr His Val Asp Ser Met Asp
            340                 345                 350

Leu Ile Thr Lys Gly Asp Leu Ile Glu Ile Glu Arg Cys Glu Pro Val
            355                 360                 365

Arg Ser Lys Leu Glu Glu Val Gln Arg Lys Leu Gly Phe Ala Leu Ser
370                 375                 380

Asp Ile Ser Val Val Ser Asn Tyr Ser Ser Glu Trp Glu Leu Asp Pro
385                 390                 395                 400

Val Lys Asp Val Leu Ile Leu Ser Ala Leu Arg Arg Met Leu Trp Ala
            405                 410                 415

Ala Asp Asp Phe Leu Glu Asp Leu Pro Phe Glu Gln Ile Gly Asn Leu
            420                 425                 430

Arg Glu Glu Ile Ile Asn Cys Ala Gln Gly Lys Lys
            435                 440

<210> SEQ ID NO 5
<211> LENGTH: 452
<212> TYPE: PRT
<213> ORGANISM: Homo sapiens

<400> SEQUENCE: 5

Met Glu Val Thr Thr Arg Leu Thr Trp Asn Asp Glu Asn His Leu Arg
1               5                   10                  15

Lys Leu Leu Gly Asn Val Ser Leu Ser Leu Tyr Lys Ser Ser Val
            20                  25                  30

His Gly Gly Ser Ile Glu Asp Met Val Glu Arg Cys Ser Arg Gln Gly
        35                  40                  45

Cys Thr Ile Thr Met Ala Tyr Ile Asp Tyr Asn Met Ile Val Ala Phe
    50                  55                  60

Met Leu Gly Asn Tyr Ile Asn Leu His Glu Ser Ser Thr Glu Pro Asn
65              70                  75                  80

Asp Ser Leu Trp Phe Ser Leu Gln Lys Lys Asn Asp Thr Thr Glu Ile
                85                  90                  95

Glu Thr Leu Leu Leu Asn Thr Ala Pro Lys Ile Ile Asp Glu Gln Leu
            100                 105                 110

Val Cys Arg Leu Ser Lys Thr Asp Ile Phe Ile Ile Cys Arg Asp Asn
            115                 120                 125

Lys Ile Tyr Leu Asp Lys Met Ile Thr Arg Asn Leu Lys Leu Arg Phe
130                 135                 140

Tyr Gly His Arg Gln Tyr Leu Glu Cys Glu Val Phe Arg Val Glu Gly
145                 150                 155                 160

Ile Lys Asp Asn Leu Asp Asp Ile Lys Arg Ile Lys Ala Arg Glu
            165                 170                 175

His Arg Asn Arg Leu Leu Ala Asp Ile Arg Asp Tyr Arg Pro Tyr Ala
            180                 185                 190

Asp Leu Val Ser Glu Ile Arg Ile Leu Leu Val Gly Pro Val Gly Ser
            195                 200                 205

Gly Lys Ser Ser Phe Phe Asn Ser Val Lys Ser Ile Phe His Gly His
        210                 215                 220

Val Thr Gly Gln Ala Val Val Gly Ser Asp Ile Thr Ser Ile Thr Glu
225                 230                 235                 240

Arg Tyr Arg Ile Tyr Ser Val Lys Asp Gly Lys Asn Gly Lys Ser Leu
                245                 250                 255
```

```
Pro Phe Met Leu Cys Asp Thr Met Gly Leu Asp Gly Ala Glu Gly Ala
            260                 265                 270

Gly Leu Cys Met Asp Asp Ile Pro His Ile Leu Lys Gly Cys Met Pro
            275                 280                 285

Asp Arg Tyr Gln Phe Asn Ser Arg Lys Pro Ile Thr Pro Glu His Ser
            290                 295                 300

Thr Phe Ile Thr Ser Pro Ser Leu Lys Asp Arg Ile His Cys Val Ala
305                 310                 315                 320

Tyr Val Leu Asp Ile Asn Ser Ile Asp Asn Leu Tyr Ser Lys Met Leu
                325                 330                 335

Ala Lys Val Lys Gln Val His Lys Glu Val Leu Asn Cys Gly Ile Ala
            340                 345                 350

Tyr Val Ala Leu Leu Thr Lys Val Asp Asp Cys Ser Glu Val Leu Gln
            355                 360                 365

Asp Asn Phe Leu Asn Met Ser Arg Ser Met Thr Ser Gln Ser Arg Val
            370                 375                 380

Met Asn Val His Lys Met Leu Gly Ile Pro Ile Ser Asn Ile Leu Met
385                 390                 395                 400

Val Gly Asn Tyr Ala Ser Asp Leu Glu Leu Asp Pro Met Lys Asp Ile
                405                 410                 415

Leu Ile Leu Ser Ala Leu Arg Gln Met Leu Arg Ala Ala Asp Asp Phe
            420                 425                 430

Leu Glu Asp Leu Pro Leu Glu Glu Thr Gly Ala Ile Glu Arg Ala Leu
            435                 440                 445

Gln Pro Cys Ile
    450

<210> SEQ ID NO 6
<211> LENGTH: 361
<212> TYPE: PRT
<213> ORGANISM: Homo sapiens

<400> SEQUENCE: 6

Met Trp Val Leu Thr Pro Ala Ala Phe Ala Gly Lys Leu Leu Ser Val
1               5                   10                  15

Phe Arg Gln Pro Leu Ser Ser Leu Trp Arg Ser Leu Val Pro Leu Phe
            20                  25                  30

Cys Trp Leu Arg Ala Thr Phe Trp Leu Leu Ala Thr Lys Arg Arg Lys
            35                  40                  45

Gln Gln Leu Val Leu Arg Gly Pro Asp Glu Thr Lys Glu Glu Glu Glu
        50                  55                  60

Asp Pro Pro Leu Pro Thr Thr Pro Thr Ser Val Asn Tyr His Phe Thr
65                  70                  75                  80

Arg Gln Cys Asn Tyr Lys Cys Gly Phe Cys Phe His Thr Ala Lys Thr
                85                  90                  95

Ser Phe Val Leu Pro Leu Glu Glu Ala Lys Arg Gly Leu Leu Leu Leu
            100                 105                 110

Lys Glu Ala Gly Met Glu Lys Ile Asn Phe Ser Gly Gly Glu Pro Phe
            115                 120                 125

Leu Gln Asp Arg Gly Glu Tyr Leu Gly Lys Leu Val Arg Phe Cys Lys
        130                 135                 140

Val Glu Leu Arg Leu Pro Ser Val Ser Ile Val Ser Asn Gly Ser Leu
145                 150                 155                 160

Ile Arg Glu Arg Trp Phe Gln Asn Tyr Gly Glu Tyr Leu Asp Ile Leu
```

```
                        165                 170                 175
Ala Ile Ser Cys Asp Ser Phe Asp Glu Glu Val Asn Val Leu Ile Gly
                180                 185                 190

Arg Gly Gln Gly Lys Lys Asn His Val Glu Asn Leu Gln Lys Leu Arg
            195                 200                 205

Arg Trp Cys Arg Asp Tyr Arg Val Ala Phe Lys Ile Asn Ser Val Ile
    210                 215                 220

Asn Arg Phe Asn Val Glu Glu Asp Met Thr Glu Gln Ile Lys Ala Leu
225                 230                 235                 240

Asn Pro Val Arg Trp Lys Val Phe Gln Cys Leu Leu Ile Gly Glu
                245                 250                 255

Asn Cys Gly Glu Asp Ala Leu Arg Glu Ala Glu Arg Phe Val Ile Gly
            260                 265                 270

Asp Glu Glu Phe Glu Arg Phe Leu Glu Arg His Lys Glu Val Ser Cys
        275                 280                 285

Leu Val Pro Glu Ser Asn Gln Lys Met Lys Asp Ser Tyr Leu Ile Leu
    290                 295                 300

Asp Glu Tyr Met Arg Phe Leu Asn Cys Arg Lys Gly Arg Lys Asp Pro
305                 310                 315                 320

Ser Lys Ser Ile Leu Asp Val Gly Val Glu Glu Ala Ile Lys Phe Ser
                325                 330                 335

Gly Phe Asp Glu Lys Met Phe Leu Lys Arg Gly Gly Lys Tyr Ile Trp
            340                 345                 350

Ser Lys Ala Asp Leu Lys Leu Asp Trp
        355                 360

<210> SEQ ID NO 7
<211> LENGTH: 130
<212> TYPE: PRT
<213> ORGANISM: Homo sapiens

<400> SEQUENCE: 7

Met Arg Gln Lys Ala Val Ser Leu Phe Leu Cys Tyr Leu Leu Leu Phe
1               5                   10                  15

Thr Cys Ser Gly Val Glu Ala Gly Lys Lys Cys Ser Glu Ser Ser
            20                  25                  30

Asp Ser Gly Ser Gly Phe Trp Lys Ala Leu Thr Phe Met Ala Val Gly
        35                  40                  45

Gly Gly Leu Ala Val Ala Gly Leu Pro Ala Leu Gly Phe Thr Gly Ala
    50                  55                  60

Gly Ile Ala Ala Asn Ser Val Ala Ala Ser Leu Met Ser Trp Ser Ala
65                  70                  75                  80

Ile Leu Asn Gly Gly Gly Val Pro Ala Gly Gly Leu Val Ala Thr Leu
                85                  90                  95

Gln Ser Leu Gly Ala Gly Gly Ser Ser Val Val Ile Gly Asn Ile Gly
            100                 105                 110

Ala Leu Met Gly Tyr Ala Thr His Lys Tyr Leu Asp Ser Glu Glu Asp
        115                 120                 125

Glu Glu
    130

<210> SEQ ID NO 8
<211> LENGTH: 662
<212> TYPE: PRT
<213> ORGANISM: Homo sapiens
```

```
<400> SEQUENCE: 8

Met Val Val Ser Glu Val Asp Ile Ala Lys Ala Asp Pro Ala Ala
1               5                   10                  15

Ser His Pro Leu Leu Asn Gly Asp Ala Thr Val Ala Gln Lys Asn
                20                  25                  30

Pro Gly Ser Val Ala Glu Asn Leu Cys Ser Gln Tyr Glu Glu Lys
            35                  40                  45

Val Arg Pro Cys Ile Asp Leu Ile Asp Ser Leu Arg Ala Leu Gly Val
    50                  55                  60

Glu Gln Asp Leu Ala Leu Pro Ala Ile Ala Val Ile Gly Asp Gln Ser
65                  70                  75                  80

Ser Gly Lys Ser Ser Val Leu Glu Ala Leu Ser Gly Val Ala Leu Pro
                85                  90                  95

Arg Gly Ser Gly Ile Val Thr Arg Cys Pro Leu Val Leu Lys Leu Lys
            100                 105                 110

Lys Leu Val Asn Glu Asp Lys Trp Arg Gly Lys Val Ser Tyr Gln Asp
            115                 120                 125

Tyr Glu Ile Glu Ile Ser Asp Ala Ser Glu Val Glu Lys Glu Ile Asn
            130                 135                 140

Lys Ala Gln Asn Ala Ile Ala Gly Glu Gly Met Gly Ile Ser His Glu
145                 150                 155                 160

Leu Ile Thr Leu Glu Ile Ser Ser Arg Asp Val Pro Asp Leu Thr Leu
                165                 170                 175

Ile Asp Leu Pro Gly Ile Thr Arg Val Ala Val Gly Asn Gln Pro Ala
            180                 185                 190

Asp Ile Gly Tyr Lys Ile Lys Thr Leu Ile Lys Lys Tyr Ile Gln Arg
            195                 200                 205

Gln Glu Thr Ile Ser Leu Val Val Pro Ser Asn Val Asp Ile Ala
210                 215                 220

Thr Thr Glu Ala Leu Ser Met Ala Gln Glu Val Asp Pro Glu Gly Asp
225                 230                 235                 240

Arg Thr Ile Gly Ile Leu Thr Lys Pro Asp Leu Val Asp Lys Gly Thr
            245                 250                 255

Glu Asp Lys Val Val Asp Val Val Arg Asn Leu Val Phe His Leu Lys
            260                 265                 270

Lys Gly Tyr Met Ile Val Lys Cys Arg Gly Gln Gln Glu Ile Gln Asp
            275                 280                 285

Gln Leu Ser Leu Ser Glu Ala Leu Gln Arg Glu Lys Ile Phe Phe Glu
            290                 295                 300

Asn His Pro Tyr Phe Arg Asp Leu Leu Glu Glu Gly Lys Ala Thr Val
305                 310                 315                 320

Pro Cys Leu Ala Glu Lys Leu Thr Ser Glu Leu Ile Thr His Ile Cys
            325                 330                 335

Lys Ser Leu Pro Leu Leu Glu Asn Gln Ile Lys Glu Thr His Gln Arg
            340                 345                 350

Ile Thr Glu Glu Leu Gln Lys Tyr Gly Val Asp Ile Pro Glu Asp Glu
            355                 360                 365

Asn Glu Lys Met Phe Phe Leu Ile Asp Lys Val Asn Ala Phe Asn Gln
370                 375                 380

Asp Ile Thr Ala Leu Met Gln Gly Glu Glu Thr Val Gly Glu Glu Asp
385                 390                 395                 400

Ile Arg Leu Phe Thr Arg Leu Arg His Glu Phe His Lys Trp Ser Thr
            405                 410                 415
```

Ile Ile Glu Asn Asn Phe Gln Glu Gly His Lys Ile Leu Ser Arg Lys
            420                 425                 430

Ile Gln Lys Phe Glu Asn Gln Tyr Arg Gly Arg Glu Leu Pro Gly Phe
            435                 440                 445

Val Asn Tyr Arg Thr Phe Glu Thr Ile Val Lys Gln Gln Ile Lys Ala
450                 455                 460

Leu Glu Glu Pro Ala Val Asp Met Leu His Thr Val Thr Asp Met Val
465                 470                 475                 480

Arg Leu Ala Phe Thr Asp Val Ser Ile Lys Asn Phe Glu Glu Phe Phe
                485                 490                 495

Asn Leu His Arg Thr Ala Lys Ser Lys Ile Glu Asp Ile Arg Ala Glu
            500                 505                 510

Gln Glu Arg Glu Gly Glu Lys Leu Ile Arg Leu His Phe Gln Met Glu
        515                 520                 525

Gln Ile Val Tyr Cys Gln Asp Gln Val Tyr Arg Gly Ala Leu Gln Lys
    530                 535                 540

Val Arg Glu Lys Glu Leu Glu Glu Lys Lys Lys Ser Trp Asp
545                 550                 555                 560

Phe Gly Ala Phe Gln Ser Ser Ala Thr Asp Ser Ser Met Glu Glu
                565                 570                 575

Ile Phe Gln His Leu Met Ala Tyr His Gln Glu Ala Ser Lys Arg Ile
            580                 585                 590

Ser Ser His Ile Pro Leu Ile Ile Gln Phe Phe Met Leu Gln Thr Tyr
        595                 600                 605

Gly Gln Gln Leu Gln Lys Ala Met Leu Gln Leu Gln Asp Lys Asp
    610                 615                 620

Thr Tyr Ser Trp Leu Leu Lys Glu Arg Ser Asp Thr Ser Asp Lys Arg
625                 630                 635                 640

Lys Phe Leu Lys Glu Arg Leu Ala Arg Leu Thr Gln Ala Arg Arg
                645                 650                 655

Leu Ala Gln Phe Pro Gly
            660

<210> SEQ ID NO 9
<211> LENGTH: 478
<212> TYPE: PRT
<213> ORGANISM: Homo sapiens

<400> SEQUENCE: 9

Met Ser Thr Asn Gly Asp Asp His Gln Val Lys Asp Ser Leu Glu Gln
1               5                   10                  15

Leu Arg Cys His Phe Thr Trp Glu Leu Ser Ile Asp Asp Glu Met
            20                  25                  30

Pro Asp Leu Glu Asn Arg Val Leu Asp Gln Ile Glu Phe Leu Asp Thr
        35                  40                  45

Lys Tyr Ser Val Gly Ile His Asn Leu Leu Ala Tyr Val Lys His Leu
    50                  55                  60

Lys Gly Gln Asn Glu Glu Ala Leu Lys Ser Leu Lys Glu Ala Glu Asn
65                  70                  75                  80

Leu Met Gln Glu Glu His Asp Asn Gln Ala Asn Val Arg Ser Leu Val
                85                  90                  95

Thr Trp Gly Asn Phe Ala Trp Met Tyr Tyr His Met Gly Arg Leu Ala
            100                 105                 110

Glu Ala Gln Thr Tyr Leu Asp Lys Val Glu Asn Ile Cys Lys Lys Leu

```
                      115                 120                 125
        Ser Asn Pro Phe Arg Tyr Arg Met Glu Cys Pro Glu Ile Asp Cys Glu
        130                 135                 140

Glu Gly Trp Ala Leu Leu Lys Cys Gly Gly Lys Asn Tyr Glu Arg Ala
        145                 150                 155                 160

Lys Ala Cys Phe Glu Lys Val Leu Glu Val Asp Pro Glu Asn Pro Glu
                        165                 170                 175

Ser Ser Ala Gly Tyr Ala Ile Ser Ala Tyr Arg Leu Asp Gly Phe Lys
                    180                 185                 190

Leu Ala Thr Lys Asn His Lys Pro Phe Ser Leu Leu Pro Leu Arg Gln
                195                 200                 205

Ala Val Arg Leu Asn Pro Asp Asn Gly Tyr Ile Lys Val Leu Leu Ala
        210                 215                 220

Leu Lys Leu Gln Asp Glu Gly Gln Glu Ala Gly Glu Lys Tyr Ile
        225                 230                 235                 240

Glu Glu Ala Leu Ala Asn Met Ser Ser Gln Thr Tyr Val Phe Arg Tyr
                        245                 250                 255

Ala Ala Lys Phe Tyr Arg Arg Lys Gly Ser Val Asp Lys Ala Leu Glu
                    260                 265                 270

Leu Leu Lys Lys Ala Leu Gln Glu Thr Pro Thr Ser Val Leu Leu His
                275                 280                 285

His Gln Ile Gly Leu Cys Tyr Lys Ala Gln Met Ile Gln Ile Lys Glu
        290                 295                 300

Ala Thr Lys Gly Gln Pro Arg Gly Gln Asn Arg Glu Lys Leu Asp Lys
        305                 310                 315                 320

Met Ile Arg Ser Ala Ile Phe His Phe Glu Ser Ala Val Glu Lys Lys
                        325                 330                 335

Pro Thr Phe Glu Val Ala His Leu Asp Leu Ala Arg Met Tyr Ile Glu
                    340                 345                 350

Ala Gly Asn His Arg Lys Ala Glu Glu Asn Phe Gln Lys Leu Leu Cys
                355                 360                 365

Met Lys Pro Val Val Glu Glu Thr Met Gln Asp Ile His Phe His Tyr
        370                 375                 380

Gly Arg Phe Gln Glu Phe Gln Lys Lys Ser Asp Val Asn Ala Ile Ile
        385                 390                 395                 400

His Tyr Leu Lys Ala Ile Lys Ile Glu Gln Ala Ser Leu Thr Arg Asp
                        405                 410                 415

Lys Ser Ile Asn Ser Leu Lys Lys Leu Val Leu Arg Lys Leu Arg Arg
                    420                 425                 430

Lys Ala Leu Asp Leu Glu Ser Leu Ser Leu Leu Gly Phe Val Tyr Lys
                435                 440                 445

Leu Glu Gly Asn Met Asn Glu Ala Leu Glu Tyr Tyr Glu Arg Ala Leu
            450                 455                 460

Arg Leu Ala Ala Asp Phe Glu Asn Ser Val Arg Gln Gly Pro
        465                 470                 475

<210> SEQ ID NO 10
<211> LENGTH: 1024
<212> TYPE: PRT
<213> ORGANISM: Homo sapiens

<400> SEQUENCE: 10

Met Glu Arg Arg Ser Arg Arg Lys Ser Arg Arg Asn Gly Arg Ser Thr
1               5                   10                  15
```

```
Ala Gly Lys Ala Ala Ala Thr Gln Pro Ala Lys Ser Pro Gly Ala Gln
            20                  25                  30

Leu Trp Leu Phe Pro Ser Ala Ala Gly Leu His Arg Ala Leu Leu Arg
        35                  40                  45

Arg Val Glu Val Thr Arg Gln Leu Cys Cys Ser Pro Gly Arg Leu Ala
    50                  55                  60

Val Leu Glu Arg Gly Gly Ala Gly Val Gln Val His Gln Leu Leu Ala
65                  70                  75                  80

Gly Ser Gly Gly Ala Arg Thr Pro Lys Cys Ile Lys Leu Gly Lys Asn
                85                  90                  95

Met Lys Ile His Ser Val Asp Gln Gly Ala Glu His Met Leu Ile Leu
            100                 105                 110

Ser Ser Asp Gly Lys Pro Phe Glu Tyr Asp Asn Tyr Ser Met Lys His
        115                 120                 125

Leu Arg Phe Glu Ser Ile Leu Gln Glu Lys Lys Ile Ile Gln Ile Thr
    130                 135                 140

Cys Gly Asp Tyr His Ser Leu Ala Leu Ser Lys Gly Gly Glu Leu Phe
145                 150                 155                 160

Ala Trp Gly Gln Asn Leu His Gly Gln Leu Gly Val Gly Arg Lys Phe
                165                 170                 175

Pro Ser Thr Thr Thr Pro Gln Ile Val Glu His Leu Ala Gly Val Pro
            180                 185                 190

Leu Ala Gln Ile Ser Ala Gly Glu Ala His Ser Met Ala Leu Ser Met
        195                 200                 205

Ser Gly Asn Ile Tyr Ser Trp Gly Lys Asn Glu Cys Gly Gln Leu Gly
    210                 215                 220

Leu Gly His Thr Glu Ser Lys Asp Asp Pro Ser Leu Ile Glu Gly Leu
225                 230                 235                 240

Asp Asn Gln Lys Val Glu Phe Val Ala Cys Gly Gly Ser His Ser Ala
                245                 250                 255

Leu Leu Thr Gln Asp Gly Leu Leu Phe Thr Phe Gly Ala Gly Lys His
            260                 265                 270

Gly Gln Leu Gly His Asn Ser Thr Gln Asn Glu Leu Arg Pro Cys Leu
        275                 280                 285

Val Ala Glu Leu Val Gly Tyr Arg Val Thr Gln Ile Ala Cys Gly Arg
    290                 295                 300

Trp His Thr Leu Ala Tyr Val Ser Asp Leu Gly Lys Val Phe Ser Phe
305                 310                 315                 320

Gly Ser Gly Lys Asp Gly Gln Leu Gly Asn Gly Gly Thr Arg Asp Gln
                325                 330                 335

Leu Met Pro Leu Pro Val Lys Val Ser Ser Ser Glu Glu Leu Lys Leu
            340                 345                 350

Glu Ser His Thr Ser Glu Lys Glu Leu Ile Met Ile Ala Gly Gly Asn
        355                 360                 365

Gln Ser Ile Leu Leu Trp Ile Lys Lys Glu Asn Ser Tyr Val Asn Leu
    370                 375                 380

Lys Arg Thr Ile Pro Thr Leu Asn Glu Gly Thr Val Lys Arg Trp Ile
385                 390                 395                 400

Ala Asp Val Glu Thr Lys Arg Trp Gln Ser Thr Lys Arg Glu Ile Gln
                405                 410                 415

Glu Ile Phe Ser Ser Pro Ala Cys Leu Thr Gly Ser Phe Leu Arg Lys
            420                 425                 430

Arg Arg Thr Thr Glu Met Met Pro Val Tyr Leu Asp Leu Asn Lys Ala
```

-continued

```
            435                 440                 445
Arg Asn Ile Phe Lys Glu Leu Thr Gln Lys Asp Trp Ile Thr Asn Met
450                 455                 460
Ile Thr Thr Cys Leu Lys Asp Asn Leu Leu Lys Arg Leu Pro Phe His
465                 470                 475                 480
Ser Pro Pro Gln Glu Ala Leu Glu Ile Phe Phe Leu Leu Pro Glu Cys
                485                 490                 495
Pro Met Met His Ile Ser Asn Asn Trp Glu Ser Leu Val Val Pro Phe
                500                 505                 510
Ala Lys Val Val Cys Lys Met Ser Asp Gln Ser Ser Leu Val Leu Glu
            515                 520                 525
Glu Tyr Trp Ala Thr Leu Gln Glu Ser Thr Phe Ser Lys Leu Val Gln
530                 535                 540
Met Phe Lys Thr Ala Val Ile Cys Gln Leu Asp Tyr Trp Asp Glu Ser
545                 550                 555                 560
Ala Glu Glu Asn Gly Asn Val Gln Ala Leu Leu Glu Met Leu Lys Lys
                565                 570                 575
Leu His Arg Val Asn Gln Val Lys Cys Gln Leu Pro Glu Ser Ile Phe
                580                 585                 590
Gln Val Asp Glu Leu Leu His Arg Leu Asn Phe Phe Val Glu Val Cys
            595                 600                 605
Arg Arg Tyr Leu Trp Lys Met Thr Val Asp Ala Ser Glu Asn Val Gln
610                 615                 620
Cys Cys Val Ile Phe Ser His Phe Pro Phe Ile Phe Asn Asn Leu Ser
625                 630                 635                 640
Lys Ile Lys Leu Leu His Thr Asp Thr Leu Leu Lys Ile Glu Ser Lys
                645                 650                 655
Lys His Lys Ala Tyr Leu Arg Ser Ala Ala Ile Glu Glu Glu Arg Glu
                660                 665                 670
Ser Glu Phe Ala Leu Arg Pro Thr Phe Asp Leu Thr Val Arg Arg Asn
            675                 680                 685
His Leu Ile Glu Asp Val Leu Asn Gln Leu Ser Gln Phe Glu Asn Glu
        690                 695                 700
Asp Leu Arg Lys Glu Leu Trp Val Ser Phe Ser Gly Glu Ile Gly Tyr
705                 710                 715                 720
Asp Leu Gly Gly Val Lys Lys Glu Phe Phe Tyr Cys Leu Phe Ala Glu
                725                 730                 735
Met Ile Gln Pro Glu Tyr Gly Met Phe Met Tyr Pro Glu Gly Ala Ser
            740                 745                 750
Cys Met Trp Phe Pro Val Lys Pro Lys Phe Glu Lys Arg Tyr Phe
            755                 760                 765
Phe Phe Gly Val Leu Cys Gly Leu Ser Leu Phe Asn Cys Asn Val Ala
            770                 775                 780
Asn Leu Pro Phe Pro Leu Ala Leu Phe Lys Lys Leu Leu Asp Gln Met
785                 790                 795                 800
Pro Ser Leu Glu Asp Leu Lys Glu Leu Ser Pro Asp Leu Gly Lys Asn
                805                 810                 815
Leu Gln Thr Leu Leu Asp Asp Glu Gly Asp Asn Phe Glu Glu Val Phe
            820                 825                 830
Tyr Ile His Phe Asn Val His Trp Asp Arg Asn Asp Thr Asn Leu Ile
            835                 840                 845
Pro Asn Gly Ser Ser Ile Thr Val Asn Gln Thr Asn Lys Arg Asp Tyr
850                 855                 860
```

Val Ser Lys Tyr Ile Asn Tyr Ile Phe Asn Asp Ser Val Lys Ala Val
865                 870                 875                 880

Tyr Glu Glu Phe Arg Arg Gly Phe Tyr Lys Met Cys Asp Glu Asp Ile
            885                 890                 895

Ile Lys Leu Phe His Pro Glu Glu Leu Lys Asp Val Ile Val Gly Asn
            900                 905                 910

Thr Asp Tyr Asp Trp Lys Thr Phe Glu Lys Asn Ala Arg Tyr Glu Pro
            915                 920                 925

Gly Tyr Asn Ser Ser His Pro Thr Ile Val Met Phe Trp Lys Ala Phe
            930                 935                 940

His Lys Leu Thr Leu Glu Glu Lys Lys Lys Phe Leu Val Phe Leu Thr
945                 950                 955                 960

Gly Thr Asp Arg Leu Gln Met Lys Asp Leu Asn Asn Met Lys Ile Thr
            965                 970                 975

Phe Cys Cys Pro Glu Ser Trp Asn Glu Arg Asp Pro Ile Arg Ala Leu
            980                 985                 990

Thr Cys Phe Ser Val Leu Phe Leu  Pro Lys Tyr Ser Thr  Met Glu Thr
            995                 1000                1005

Val Glu  Glu Ala Leu Gln Glu  Ala Ile Asn Asn Asn  Arg Gly Phe
    1010                 1015                1020

Gly

<210> SEQ ID NO 11
<211> LENGTH: 165
<212> TYPE: PRT
<213> ORGANISM: Homo sapiens

<400> SEQUENCE: 11

Met Gly Trp Asp Leu Thr Val Lys Met Leu Ala Gly Asn Glu Phe Gln
1               5                   10                  15

Val Ser Leu Ser Ser Ser Met Ser Val Ser Glu Leu Lys Ala Gln Ile
            20                  25                  30

Thr Gln Lys Ile Gly Val His Ala Phe Gln Gln Arg Leu Ala Val His
            35                  40                  45

Pro Ser Gly Val Ala Leu Gln Asp Arg Val Pro Leu Ala Ser Gln Gly
        50                  55                  60

Leu Gly Pro Gly Ser Thr Val Leu Leu Val Val Asp Lys Cys Asp Glu
65                  70                  75                  80

Pro Leu Ser Ile Leu Val Arg Asn Asn Lys Gly Arg Ser Ser Thr Tyr
            85                  90                  95

Glu Val Arg Leu Thr Gln Thr Val Ala His Leu Lys Gln Gln Val Ser
            100                 105                 110

Gly Leu Glu Gly Val Gln Asp Asp Leu Phe Trp Leu Thr Phe Glu Gly
            115                 120                 125

Lys Pro Leu Glu Asp Gln Leu Pro Leu Gly Glu Tyr Gly Leu Lys Pro
            130                 135                 140

Leu Ser Thr Val Phe Met Asn Leu Arg Leu Arg Gly Gly Gly Thr Glu
145                 150                 155                 160

Pro Gly Gly Arg Ser
                165

<210> SEQ ID NO 12
<211> LENGTH: 416
<212> TYPE: PRT
<213> ORGANISM: Homo sapiens

<400> SEQUENCE: 12

```
Met Pro Arg Gln Leu Ser Ala Ala Ala Leu Phe Ala Ser Leu Ala
1               5                   10                  15

Val Ile Leu His Asp Gly Ser Gln Met Arg Ala Lys Ala Phe Pro Glu
            20                  25                  30

Thr Arg Asp Tyr Ser Gln Pro Thr Ala Ala Thr Val Gln Asp Ile
        35                  40                  45

Lys Lys Pro Val Gln Gln Pro Ala Lys Gln Ala Pro His Gln Thr Leu
    50                  55                  60

Ala Ala Arg Phe Met Asp Gly His Ile Thr Phe Gln Thr Ala Ala Thr
65              70                  75                  80

Val Lys Ile Pro Thr Thr Thr Pro Ala Thr Lys Asn Thr Ala Thr
                85                  90                  95

Thr Ser Pro Ile Thr Tyr Thr Leu Val Thr Thr Gln Ala Thr Pro Asn
                100                 105                 110

Asn Ser His Thr Ala Pro Pro Val Thr Glu Val Thr Val Gly Pro Ser
            115                 120                 125

Leu Ala Pro Tyr Ser Leu Pro Pro Thr Ile Pro Pro Ala His Thr
130                 135                 140

Thr Gly Thr Ser Ser Ser Thr Val Ser His Thr Thr Gly Asn Thr Thr
145                 150                 155                 160

Gln Pro Ser Asn Gln Thr Thr Leu Pro Ala Thr Leu Ser Ile Ala Leu
                165                 170                 175

His Lys Ser Thr Thr Gly Gln Lys Pro Val Gln Pro Thr His Ala Pro
            180                 185                 190

Gly Thr Thr Ala Ala Ala His Asn Thr Thr Arg Thr Ala Ala Pro Ala
            195                 200                 205

Ser Thr Val Pro Gly Pro Thr Leu Ala Pro Gln Pro Ser Ser Val Lys
    210                 215                 220

Thr Gly Ile Tyr Gln Val Leu Asn Gly Ser Arg Leu Cys Ile Lys Ala
225                 230                 235                 240

Glu Met Gly Ile Gln Leu Ile Val Gln Asp Lys Glu Ser Val Phe Ser
                245                 250                 255

Pro Arg Arg Tyr Phe Asn Ile Asp Pro Asn Ala Thr Gln Ala Ser Gly
            260                 265                 270

Asn Cys Gly Thr Arg Lys Ser Asn Leu Leu Leu Asn Phe Gln Gly Gly
            275                 280                 285

Phe Val Asn Leu Thr Phe Thr Lys Asp Glu Glu Ser Tyr Tyr Ile Ser
    290                 295                 300

Glu Val Gly Ala Tyr Leu Thr Val Ser Asp Pro Glu Thr Ile Tyr Gln
305                 310                 315                 320

Gly Ile Lys His Ala Val Val Met Phe Gln Thr Ala Val Gly His Ser
                325                 330                 335

Phe Lys Cys Val Ser Glu Gln Ser Leu Gln Leu Ser Ala His Leu Gln
            340                 345                 350

Val Lys Thr Thr Asp Val Gln Leu Gln Ala Phe Asp Phe Glu Asp Asp
            355                 360                 365

His Phe Gly Asn Val Asp Glu Cys Ser Ser Asp Tyr Thr Ile Val Leu
            370                 375                 380

Pro Val Ile Gly Ala Ile Val Val Gly Leu Cys Leu Met Gly Met Gly
385                 390                 395                 400

Val Tyr Lys Ile Arg Leu Arg Cys Gln Ser Ser Gly Tyr Gln Arg Ile
```

-continued

```
                405                 410                 415

<210> SEQ ID NO 13
<211> LENGTH: 1087
<212> TYPE: PRT
<213> ORGANISM: Homo sapiens

<400> SEQUENCE: 13

Met Asp Leu Tyr Ser Thr Pro Ala Ala Leu Asp Arg Phe Val Ala
1               5                   10                  15

Arg Arg Leu Gln Pro Arg Lys Glu Phe Val Glu Lys Ala Arg Arg Ala
            20                  25                  30

Leu Gly Ala Leu Ala Ala Leu Arg Glu Arg Gly Gly Arg Leu Gly
        35                  40                  45

Ala Ala Ala Pro Arg Val Leu Lys Thr Val Lys Gly Gly Ser Ser Gly
    50                  55                  60

Arg Gly Thr Ala Leu Lys Gly Gly Cys Asp Ser Glu Leu Val Ile Phe
65                  70                  75                  80

Leu Asp Cys Phe Lys Ser Tyr Val Asp Gln Arg Ala Arg Arg Ala Glu
                85                  90                  95

Ile Leu Ser Glu Met Arg Ala Ser Leu Glu Ser Trp Trp Gln Asn Pro
            100                 105                 110

Val Pro Gly Leu Arg Leu Thr Phe Pro Glu Gln Ser Val Pro Gly Ala
        115                 120                 125

Leu Gln Phe Arg Leu Thr Ser Val Asp Leu Glu Asp Trp Met Asp Val
    130                 135                 140

Ser Leu Val Pro Ala Phe Asn Val Leu Gly Gln Ala Gly Ser Gly Val
145                 150                 155                 160

Lys Pro Lys Pro Gln Val Tyr Ser Thr Leu Leu Asn Ser Gly Cys Gln
                165                 170                 175

Gly Gly Glu His Ala Ala Cys Phe Thr Glu Leu Arg Arg Asn Phe Val
            180                 185                 190

Asn Ile Arg Pro Ala Lys Leu Lys Asn Leu Ile Leu Val Lys His
        195                 200                 205

Trp Tyr His Gln Val Cys Leu Gln Gly Leu Trp Lys Glu Thr Leu Pro
    210                 215                 220

Pro Val Tyr Ala Leu Glu Leu Leu Thr Ile Phe Ala Trp Glu Gln Gly
225                 230                 235                 240

Cys Lys Lys Asp Ala Phe Ser Leu Ala Glu Gly Leu Arg Thr Val Leu
                245                 250                 255

Gly Leu Ile Gln Gln His Gln His Leu Cys Val Phe Trp Thr Val Asn
            260                 265                 270

Tyr Gly Phe Glu Asp Pro Ala Val Gly Gln Phe Leu Gln Arg Gln Leu
        275                 280                 285

Lys Arg Pro Arg Pro Val Ile Leu Asp Pro Ala Asp Pro Thr Trp Asp
    290                 295                 300

Leu Gly Asn Gly Ala Ala Trp His Trp Asp Leu Leu Ala Gln Glu Ala
305                 310                 315                 320

Ala Ser Cys Tyr Asp His Pro Cys Phe Leu Arg Gly Met Gly Asp Pro
                325                 330                 335

Val Gln Ser Trp Lys Gly Pro Gly Leu Pro Arg Ala Gly Cys Ser Gly
            340                 345                 350

Leu Gly His Pro Ile Gln Leu Asp Pro Asn Gln Lys Thr Pro Glu Asn
        355                 360                 365
```

-continued

```
Ser Lys Ser Leu Asn Ala Val Tyr Pro Arg Ala Gly Ser Lys Pro Pro
370                 375                 380

Ser Cys Pro Ala Pro Gly Pro Thr Gly Ala Ala Ser Ile Val Pro Ser
385                 390                 395                 400

Val Pro Gly Met Ala Leu Asp Leu Ser Gln Ile Pro Thr Lys Glu Leu
                405                 410                 415

Asp Arg Phe Ile Gln Asp His Leu Lys Pro Ser Pro Gln Phe Gln Glu
            420                 425                 430

Gln Val Lys Lys Ala Ile Asp Ile Ile Leu Arg Cys Leu His Glu Asn
                435                 440                 445

Cys Val His Lys Ala Ser Arg Val Ser Lys Gly Gly Ser Phe Gly Arg
450                 455                 460

Gly Thr Asp Leu Arg Asp Gly Cys Asp Val Glu Leu Ile Ile Phe Leu
465                 470                 475                 480

Asn Cys Phe Thr Asp Tyr Lys Asp Gln Gly Pro Arg Ala Glu Ile
                485                 490                 495

Leu Asp Glu Met Arg Ala Gln Leu Glu Ser Trp Trp Gln Asp Gln Val
                500                 505                 510

Pro Ser Leu Ser Leu Gln Phe Pro Glu Gln Asn Val Pro Glu Ala Leu
515                 520                 525

Gln Phe Gln Leu Val Ser Thr Ala Leu Lys Ser Trp Thr Asp Val Ser
530                 535                 540

Leu Leu Pro Ala Phe Asp Ala Val Gly Gln Leu Ser Ser Gly Thr Lys
545                 550                 555                 560

Pro Asn Pro Gln Val Tyr Ser Arg Leu Leu Thr Ser Gly Cys Gln Glu
                565                 570                 575

Gly Glu His Lys Ala Cys Phe Ala Glu Leu Arg Arg Asn Phe Met Asn
                580                 585                 590

Ile Arg Pro Val Lys Leu Lys Asn Leu Ile Leu Leu Val Lys His Trp
            595                 600                 605

Tyr Arg Gln Val Ala Ala Gln Asn Lys Gly Lys Gly Pro Ala Pro Ala
            610                 615                 620

Ser Leu Pro Pro Ala Tyr Ala Leu Glu Leu Leu Thr Ile Phe Ala Trp
625                 630                 635                 640

Glu Gln Gly Cys Arg Gln Asp Cys Phe Asn Met Ala Gln Gly Phe Arg
                645                 650                 655

Thr Val Leu Gly Leu Val Gln Gln His Gln Gln Leu Cys Val Tyr Trp
                660                 665                 670

Thr Val Asn Tyr Ser Thr Glu Asp Pro Ala Met Arg Met His Leu Leu
            675                 680                 685

Gly Gln Leu Arg Lys Pro Arg Pro Leu Val Leu Asp Pro Ala Asp Pro
690                 695                 700

Thr Trp Asn Val Gly His Gly Ser Trp Glu Leu Leu Ala Gln Glu Ala
705                 710                 715                 720

Ala Ala Leu Gly Met Gln Ala Cys Phe Leu Ser Arg Asp Gly Thr Ser
                725                 730                 735

Val Gln Pro Trp Asp Val Met Pro Ala Leu Leu Tyr Gln Thr Pro Ala
                740                 745                 750

Gly Asp Leu Asp Lys Phe Ile Ser Glu Phe Leu Gln Pro Asn Arg Gln
                755                 760                 765

Phe Leu Ala Gln Val Asn Lys Ala Val Asp Thr Ile Cys Ser Phe Leu
770                 775                 780

Lys Glu Asn Cys Phe Arg Asn Ser Pro Ile Lys Val Ile Lys Val Val
```

```
            785                 790                 795                 800
Lys Gly Gly Ser Ser Ala Lys Gly Thr Ala Leu Arg Gly Arg Ser Asp
                    805                 810                 815

Ala Asp Leu Val Val Phe Leu Ser Cys Phe Ser Gln Phe Thr Glu Gln
                820                 825                 830

Gly Asn Lys Arg Ala Glu Ile Ile Ser Glu Ile Arg Ala Gln Leu Glu
                835                 840                 845

Ala Cys Gln Gln Glu Arg Gln Phe Glu Val Lys Phe Glu Val Ser Lys
            850                 855                 860

Trp Glu Asn Pro Arg Val Leu Ser Phe Ser Leu Thr Ser Gln Thr Met
865                 870                 875                 880

Leu Asp Gln Ser Val Asp Phe Asp Val Leu Pro Ala Phe Asp Ala Leu
                885                 890                 895

Gly Gln Leu Val Ser Gly Ser Arg Pro Ser Ser Gln Val Tyr Val Asp
                900                 905                 910

Leu Ile His Ser Tyr Ser Asn Ala Gly Glu Tyr Ser Thr Cys Phe Thr
                915                 920                 925

Glu Leu Gln Arg Asp Phe Ile Ile Ser Arg Pro Thr Lys Leu Lys Ser
            930                 935                 940

Leu Ile Arg Leu Val Lys His Trp Tyr Gln Gln Cys Thr Lys Ile Ser
945                 950                 955                 960

Lys Gly Arg Gly Ser Leu Pro Pro Gln His Gly Leu Glu Leu Leu Thr
                965                 970                 975

Val Tyr Ala Trp Glu Gln Gly Gly Lys Asp Ser Gln Phe Asn Met Ala
                980                 985                 990

Glu Gly Phe Arg Thr Val Leu Glu Leu Val Thr Gln Tyr Arg Gln Leu
            995                 1000                1005

Cys Ile Tyr Trp Thr Ile Asn Tyr Asn Ala Lys Asp Lys Thr Val
            1010                1015                1020

Gly Asp Phe Leu Lys Gln Gln Leu Gln Lys Pro Arg Pro Ile Ile
            1025                1030                1035

Leu Asp Pro Ala Asp Pro Thr Gly Asn Leu Gly His Asn Ala Arg
            1040                1045                1050

Trp Asp Leu Leu Ala Lys Glu Ala Ala Ala Cys Thr Ser Ala Leu
            1055                1060                1065

Cys Cys Met Gly Arg Asn Gly Ile Pro Ile Gln Pro Trp Pro Val
            1070                1075                1080

Lys Ala Ala Val
            1085

<210> SEQ ID NO 14
<211> LENGTH: 400
<212> TYPE: PRT
<213> ORGANISM: Homo sapiens

<400> SEQUENCE: 14

Met Met Asp Leu Arg Asn Thr Pro Ala Lys Ser Leu Asp Lys Phe Ile
1               5                   10                  15

Glu Asp Tyr Leu Leu Pro Asp Thr Cys Phe Arg Met Gln Ile Asn His
                20                  25                  30

Ala Ile Asp Ile Ile Cys Gly Phe Leu Lys Glu Arg Cys Phe Arg Gly
            35                  40                  45

Ser Ser Tyr Pro Val Cys Val Ser Lys Val Val Lys Gly Gly Ser Ser
        50                  55                  60
```

Gly Lys Gly Thr Thr Leu Arg Gly Arg Ser Asp Ala Asp Leu Val Val
65                  70                  75                  80

Phe Leu Ser Pro Leu Thr Thr Phe Gln Asp Gln Leu Asn Arg Arg Gly
                85                  90                  95

Glu Phe Ile Gln Glu Ile Arg Arg Gln Leu Glu Ala Cys Gln Arg Glu
            100                 105                 110

Arg Ala Phe Ser Val Lys Phe Glu Val Gln Ala Pro Arg Trp Gly Asn
        115                 120                 125

Pro Arg Ala Leu Ser Phe Val Leu Ser Ser Leu Gln Leu Gly Glu Gly
    130                 135                 140

Val Glu Phe Asp Val Leu Pro Ala Phe Asp Ala Leu Gly Gln Leu Thr
145                 150                 155                 160

Gly Gly Tyr Lys Pro Asn Pro Gln Ile Tyr Val Lys Leu Ile Glu Glu
                165                 170                 175

Cys Thr Asp Leu Gln Lys Glu Gly Glu Phe Ser Thr Cys Phe Thr Glu
                180                 185                 190

Leu Gln Arg Asp Phe Leu Lys Gln Arg Pro Thr Lys Leu Lys Ser Leu
            195                 200                 205

Ile Arg Leu Val Lys His Trp Tyr Gln Asn Cys Lys Lys Lys Leu Gly
    210                 215                 220

Lys Leu Pro Pro Gln Tyr Ala Leu Glu Leu Leu Thr Val Tyr Ala Trp
225                 230                 235                 240

Glu Arg Gly Ser Met Lys Thr His Phe Asn Thr Ala Gln Gly Phe Arg
                245                 250                 255

Thr Val Leu Glu Leu Val Ile Asn Tyr Gln Gln Leu Cys Ile Tyr Trp
            260                 265                 270

Thr Lys Tyr Tyr Asp Phe Lys Asn Pro Ile Ile Glu Lys Tyr Leu Arg
        275                 280                 285

Arg Gln Leu Thr Lys Pro Arg Pro Val Ile Leu Asp Pro Ala Asp Pro
    290                 295                 300

Thr Gly Asn Leu Gly Gly Gly Asp Pro Lys Gly Trp Arg Gln Leu Ala
305                 310                 315                 320

Gln Glu Ala Glu Ala Trp Leu Asn Tyr Pro Cys Phe Lys Asn Trp Asp
                325                 330                 335

Gly Ser Pro Val Ser Ser Trp Ile Leu Leu Ala Glu Ser Asn Ser Ala
            340                 345                 350

Asp Asp Glu Thr Asp Asp Pro Arg Arg Tyr Gln Lys Tyr Gly Tyr Ile
        355                 360                 365

Gly Thr His Glu Tyr Pro His Phe Ser His Arg Pro Ser Thr Leu Gln
    370                 375                 380

Ala Ala Ser Thr Pro Gln Ala Glu Glu Asp Trp Thr Cys Thr Ile Leu
385                 390                 395                 400

<210> SEQ ID NO 15
<211> LENGTH: 410
<212> TYPE: PRT
<213> ORGANISM: Homo sapiens

<400> SEQUENCE: 15

Met Asn Thr Arg Asn Arg Val Val Asn Ser Gly Leu Gly Ala Ser Pro
1               5                   10                  15

Ala Ser Arg Pro Thr Arg Asp Pro Gln Asp Pro Ser Gly Arg Gln Gly
            20                  25                  30

Glu Leu Ser Pro Val Glu Asp Gln Arg Glu Gly Leu Glu Ala Ala Pro
        35                  40                  45

Lys Gly Pro Ser Arg Glu Ser Val His Ala Gly Gln Arg Arg Thr
            50                  55                  60

Ser Ala Tyr Thr Leu Ile Ala Pro Asn Ile Asn Arg Arg Asn Glu Ile
 65                  70                  75                  80

Gln Arg Ile Ala Glu Gln Glu Leu Ala Asn Leu Glu Lys Trp Lys Glu
                 85                  90                  95

Gln Asn Arg Ala Lys Pro Val His Leu Val Pro Arg Arg Leu Gly Gly
                100                 105                 110

Ser Gln Ser Glu Thr Glu Val Arg Gln Lys Gln Leu Gln Leu Met
            115                 120                 125

Gln Ser Lys Tyr Lys Gln Lys Leu Lys Arg Glu Ser Val Arg Ile
            130                 135                 140

Lys Lys Glu Ala Glu Glu Ala Glu Leu Gln Lys Met Lys Ala Ile Gln
145                 150                 155                 160

Arg Glu Lys Ser Asn Lys Leu Glu Glu Lys Lys Arg Leu Gln Glu Asn
                165                 170                 175

Leu Arg Arg Glu Ala Phe Arg Glu His Gln Gln Tyr Lys Thr Ala Glu
            180                 185                 190

Phe Leu Ser Lys Leu Asn Thr Glu Ser Pro Asp Arg Ser Ala Cys Gln
            195                 200                 205

Ser Ala Val Cys Gly Pro Gln Ser Ser Thr Trp Lys Leu Pro Ile Leu
210                 215                 220

Pro Arg Asp His Ser Trp Ala Arg Ser Trp Ala Tyr Arg Asp Ser Leu
225                 230                 235                 240

Lys Ala Glu Glu Asn Arg Lys Leu Gln Lys Met Lys Asp Glu Gln His
                245                 250                 255

Gln Lys Ser Glu Leu Leu Glu Leu Lys Arg Gln Gln Gln Glu Gln Glu
            260                 265                 270

Arg Ala Lys Ile His Gln Thr Glu His Arg Arg Val Asn Asn Ala Phe
            275                 280                 285

Leu Asp Arg Leu Gln Gly Lys Ser Gln Pro Gly Gly Leu Glu Gln Ser
            290                 295                 300

Gly Gly Cys Trp Asn Met Asn Ser Gly Asn Ser Trp Gly Ser Leu Leu
305                 310                 315                 320

Val Phe Ser Arg His Leu Arg Val Tyr Glu Lys Ile Leu Thr Pro Ile
                325                 330                 335

Trp Pro Ser Ser Thr Asp Leu Glu Lys Pro His Glu Met Leu Phe Leu
            340                 345                 350

Asn Val Ile Leu Phe Ser Leu Thr Val Phe Thr Leu Ile Ser Thr Ala
            355                 360                 365

His Thr Leu Asp Arg Ala Val Arg Ser Asp Trp Leu Leu Leu Val Leu
            370                 375                 380

Ile Tyr Ala Cys Leu Glu Glu Leu Ile Pro Glu Leu Ile Phe Asn Leu
385                 390                 395                 400

Tyr Cys Gln Gly Asn Ala Thr Leu Phe Phe
                405                 410

<210> SEQ ID NO 16
<211> LENGTH: 490
<212> TYPE: PRT
<213> ORGANISM: Homo sapiens

<400> SEQUENCE: 16

Met Ser Glu Val Thr Lys Asn Ser Leu Glu Lys Ile Leu Pro Gln Leu

```
1               5                   10                  15
Lys Cys His Phe Thr Trp Asn Leu Phe Lys Glu Asp Ser Val Ser Arg
                    20                  25                  30

Asp Leu Glu Asp Arg Val Cys Asn Gln Ile Glu Phe Leu Asn Thr Glu
                    35                  40                  45

Phe Lys Ala Thr Met Tyr Asn Leu Leu Ala Tyr Ile Lys His Leu Asp
            50                  55                  60

Gly Asn Asn Glu Ala Ala Leu Glu Cys Leu Arg Gln Ala Glu Glu Leu
65                      70                  75                  80

Ile Gln Gln Glu His Ala Asp Gln Ala Glu Ile Arg Ser Leu Val Thr
                    85                  90                  95

Trp Gly Asn Tyr Ala Trp Val Tyr Tyr His Leu Gly Arg Leu Ser Asp
                    100                 105                 110

Ala Gln Ile Tyr Val Asp Lys Val Lys Gln Thr Cys Lys Lys Phe Ser
                115                 120                 125

Asn Pro Tyr Ser Ile Glu Tyr Ser Glu Leu Asp Cys Glu Glu Gly Trp
        130                 135                 140

Thr Gln Leu Lys Cys Gly Arg Asn Glu Arg Ala Lys Val Cys Phe Glu
145                 150                 155                 160

Lys Ala Leu Glu Glu Lys Pro Asn Asn Pro Glu Phe Ser Ser Gly Leu
                165                 170                 175

Ala Ile Ala Met Tyr His Leu Asp Asn His Pro Glu Lys Gln Phe Ser
                180                 185                 190

Thr Asp Val Leu Lys Gln Ala Ile Glu Leu Ser Pro Asp Asn Gln Tyr
                195                 200                 205

Val Lys Val Leu Leu Gly Leu Lys Leu Gln Lys Met Asn Lys Glu Ala
            210                 215                 220

Glu Gly Glu Gln Phe Val Glu Glu Ala Leu Glu Lys Ser Pro Cys Gln
225                 230                 235                 240

Thr Asp Val Leu Arg Ser Ala Ala Lys Phe Tyr Arg Arg Lys Gly Asp
                245                 250                 255

Leu Asp Lys Ala Ile Glu Leu Phe Gln Arg Val Leu Glu Ser Thr Pro
            260                 265                 270

Asn Asn Gly Tyr Leu Tyr His Gln Ile Gly Cys Cys Tyr Lys Ala Lys
            275                 280                 285

Val Arg Gln Met Gln Asn Thr Gly Glu Ser Ala Ser Gly Asn Lys
            290                 295                 300

Glu Met Ile Glu Ala Leu Lys Gln Tyr Ala Met Asp Tyr Ser Asn Lys
305                 310                 315                 320

Ala Leu Glu Lys Gly Leu Asn Pro Leu Asn Ala Tyr Ser Asp Leu Ala
                325                 330                 335

Glu Phe Leu Glu Thr Glu Cys Tyr Gln Thr Pro Phe Asn Lys Glu Val
                340                 345                 350

Pro Asp Ala Glu Lys Gln Gln Ser His Gln Arg Tyr Cys Asn Leu Gln
                355                 360                 365

Lys Tyr Asn Gly Lys Ser Glu Asp Thr Ala Val Gln His Gly Leu Glu
            370                 375                 380

Gly Leu Ser Ile Ser Lys Lys Ser Thr Asp Lys Glu Glu Ile Lys Asp
385                 390                 395                 400

Gln Pro Gln Asn Val Ser Glu Asn Leu Leu Pro Gln Asn Ala Pro Asn
                405                 410                 415

Tyr Trp Tyr Leu Gln Gly Leu Ile His Lys Gln Asn Gly Asp Leu Leu
            420                 425                 430
```

```
Gln Ala Ala Lys Cys Tyr Glu Lys Glu Leu Gly Arg Leu Leu Arg Asp
        435                 440                 445

Ala Pro Ser Gly Ile Gly Ser Ile Phe Leu Ser Ala Ser Glu Leu Glu
    450                 455                 460

Asp Gly Ser Glu Glu Met Gly Gln Gly Ala Val Ser Ser Pro Arg
465                 470                 475                 480

Glu Leu Leu Ser Asn Ser Glu Gln Leu Asn
                485                 490

<210> SEQ ID NO 17
<211> LENGTH: 86
<212> TYPE: PRT
<213> ORGANISM: Homo sapiens

<400> SEQUENCE: 17

Met Lys Ile Phe Leu Pro Val Leu Leu Ala Leu Leu Gly Val Glu
1               5                   10                  15

Arg Ala Ser Ser Leu Met Cys Phe Ser Cys Leu Asn Gln Lys Ser Asn
                20                  25                  30

Leu Tyr Cys Leu Lys Pro Thr Ile Cys Ser Asp Gln Asp Asn Tyr Cys
            35                  40                  45

Val Thr Val Ser Ala Ser Ala Gly Ile Gly Asn Leu Val Thr Phe Gly
        50                  55                  60

His Ser Leu Ser Lys Thr Cys Ser Pro Ala Cys Pro Ile Pro Glu Gly
65                  70                  75                  80

Val Asn Val Ala Ala Ser
                85

<210> SEQ ID NO 18
<211> LENGTH: 172
<212> TYPE: PRT
<213> ORGANISM: Homo sapiens

<400> SEQUENCE: 18

Met Gly Asn Gly Glu Ser Gln Leu Ser Ser Val Pro Ala Gln Lys Leu
1               5                   10                  15

Gly Trp Phe Ile Gln Glu Tyr Leu Lys Pro Tyr Glu Glu Cys Gln Thr
                20                  25                  30

Leu Ile Asp Glu Met Val Asn Thr Ile Cys Asp Val Leu Gln Glu Pro
            35                  40                  45

Glu Gln Phe Pro Leu Val Gln Gly Val Ala Ile Gly Gly Ser Tyr Gly
        50                  55                  60

Arg Lys Thr Val Leu Arg Gly Asn Ser Asp Gly Thr Leu Val Leu Phe
65                  70                  75                  80

Phe Ser Asp Leu Lys Gln Phe Gln Asp Gln Lys Arg Ser Gln Arg Asp
                85                  90                  95

Ile Leu Asp Lys Thr Gly Asp Lys Leu Lys Phe Cys Leu Phe Thr Lys
            100                 105                 110

Trp Leu Lys Asn Asn Phe Glu Ile Gln Lys Ser Leu Asp Gly Phe Thr
        115                 120                 125

Ile Gln Val Phe Thr Lys Asn Gln Arg Ile Ser Phe Glu Val Leu Ala
    130                 135                 140

Ala Phe Asn Ala Leu Ser Lys His Cys Trp Val Ser Gly Glu Lys Ser
145                 150                 155                 160

Gln Arg Ser Gly Cys Gln Thr Ala Leu Cys Asn Leu
                165                 170
```

<210> SEQ ID NO 19
<211> LENGTH: 318
<212> TYPE: PRT
<213> ORGANISM: Homo sapiens

<400> SEQUENCE: 19

Met Asp Lys Gln Asn Ser Gln Met Asn Ala Ser His Pro Glu Thr Asn
1               5                   10                  15

Leu Pro Val Gly Tyr Pro Pro Gln Tyr Pro Pro Thr Ala Phe Gln Gly
            20                  25                  30

Pro Pro Gly Tyr Ser Gly Tyr Pro Gly Pro Gln Val Ser Tyr Pro Pro
        35                  40                  45

Pro Pro Ala Gly His Ser Gly Pro Gly Pro Ala Gly Phe Pro Val Pro
    50                  55                  60

Asn Gln Pro Val Tyr Asn Gln Pro Val Tyr Asn Gln Pro Val Gly Ala
65                  70                  75                  80

Ala Gly Val Pro Trp Met Pro Ala Pro Gln Pro Pro Leu Asn Cys Pro
                85                  90                  95

Pro Gly Leu Glu Tyr Leu Ser Gln Ile Asp Gln Ile Leu Ile His Gln
            100                 105                 110

Gln Ile Glu Leu Leu Glu Val Leu Thr Gly Phe Glu Thr Asn Asn Lys
        115                 120                 125

Tyr Glu Ile Lys Asn Ser Phe Gly Gln Arg Val Tyr Phe Ala Ala Glu
    130                 135                 140

Asp Thr Asp Cys Cys Thr Arg Asn Cys Cys Gly Pro Ser Arg Pro Phe
145                 150                 155                 160

Thr Leu Arg Ile Ile Asp Asn Met Gly Gln Glu Val Ile Thr Leu Glu
                165                 170                 175

Arg Pro Leu Arg Cys Ser Ser Cys Cys Cys Pro Cys Cys Leu Gln Glu
            180                 185                 190

Ile Glu Ile Gln Ala Pro Pro Gly Val Pro Ile Gly Tyr Val Ile Gln
        195                 200                 205

Thr Trp His Pro Cys Leu Pro Lys Phe Thr Ile Gln Asn Glu Lys Arg
    210                 215                 220

Glu Asp Val Leu Lys Ile Ser Gly Pro Cys Val Val Cys Ser Cys Cys
225                 230                 235                 240

Gly Asp Val Asp Phe Glu Ile Lys Ser Leu Asp Glu Gln Cys Val Val
                245                 250                 255

Gly Lys Ile Ser Lys His Trp Thr Gly Ile Leu Arg Glu Ala Phe Thr
            260                 265                 270

Asp Ala Asp Asn Phe Gly Ile Gln Phe Pro Leu Asp Leu Asp Val Lys
        275                 280                 285

Met Lys Ala Val Met Ile Gly Ala Cys Phe Leu Ile Asp Phe Met Phe
    290                 295                 300

Phe Glu Ser Thr Gly Ser Gln Glu Gln Lys Ser Gly Val Trp
305                 310                 315

<210> SEQ ID NO 20
<211> LENGTH: 1688
<212> TYPE: PRT
<213> ORGANISM: Homo sapiens

<400> SEQUENCE: 20

Met Gly Phe Leu Pro Lys Leu Leu Leu Leu Ala Ser Phe Phe Pro Ala
1               5                   10                  15

-continued

```
Gly Gln Ala Ser Trp Gly Val Ser Pro Gln Asp Val Gln Gly Val
            20                  25                  30

Lys Gly Ser Cys Leu Leu Ile Pro Cys Ile Phe Ser Phe Pro Ala Asp
        35                  40                  45

Val Glu Val Pro Asp Gly Ile Thr Ala Ile Trp Tyr Tyr Asp Tyr Ser
 50                  55                  60

Gly Gln Arg Gln Val Val Ser His Ser Ala Asp Pro Lys Leu Val Glu
 65                  70                  75                  80

Ala Arg Phe Arg Gly Arg Thr Glu Phe Met Gly Asn Pro Glu His Arg
                85                  90                  95

Val Cys Asn Leu Leu Leu Lys Asp Leu Gln Pro Glu Asp Ser Gly Ser
            100                 105                 110

Tyr Asn Phe Arg Phe Glu Ile Ser Glu Val Asn Arg Trp Ser Asp Val
            115                 120                 125

Lys Gly Thr Leu Val Thr Val Thr Glu Glu Pro Arg Val Pro Thr Ile
130                 135                 140

Ala Ser Pro Val Glu Leu Leu Glu Gly Thr Glu Val Asp Phe Asn Cys
145                 150                 155                 160

Ser Thr Pro Tyr Val Cys Leu Gln Glu Gln Val Arg Leu Gln Trp Gln
                165                 170                 175

Gly Gln Asp Pro Ala Arg Ser Val Thr Phe Asn Ser Gln Lys Phe Glu
            180                 185                 190

Pro Thr Gly Val Gly His Leu Glu Thr Leu His Met Ala Met Ser Trp
            195                 200                 205

Gln Asp His Gly Arg Ile Leu Arg Cys Gln Leu Ser Met Ala Asn His
            210                 215                 220

Arg Ala Gln Ser Glu Ile His Leu Gln Val Lys Tyr Ala Pro Arg Gly
225                 230                 235                 240

Val Lys Ile Leu Leu Ser Pro Ser Gly Arg Asn Ile Leu Pro Gly Glu
                245                 250                 255

Leu Val Thr Leu Thr Cys Gln Val Asn Ser Ser Tyr Pro Ala Val Ser
                260                 265                 270

Ser Ile Lys Trp Leu Lys Asp Gly Val Arg Leu Gln Thr Lys Thr Gly
            275                 280                 285

Val Leu His Leu Pro Gln Ala Ala Trp Ser Asp Ala Gly Val Tyr Thr
            290                 295                 300

Cys Gln Ala Glu Asn Gly Val Gly Ser Leu Val Ser Pro Pro Ile Ser
305                 310                 315                 320

Leu His Ile Phe Met Ala Glu Val Gln Val Ser Pro Ala Gly Pro Ile
                325                 330                 335

Leu Glu Asn Gln Thr Val Thr Leu Val Cys Asn Thr Pro Asn Glu Ala
            340                 345                 350

Pro Ser Asp Leu Arg Tyr Ser Trp Tyr Lys Asn His Val Leu Leu Glu
            355                 360                 365

Asp Ala His Ser His Thr Leu Arg Leu His Leu Ala Thr Arg Ala Asp
            370                 375                 380

Thr Gly Phe Tyr Phe Cys Glu Val Gln Asn Val His Gly Ser Glu Arg
385                 390                 395                 400

Ser Gly Pro Val Ser Val Val Asn His Pro Leu Thr Pro Val
                405                 410                 415

Leu Thr Ala Phe Leu Glu Thr Gln Ala Gly Leu Val Gly Ile Leu His
            420                 425                 430
```

```
Cys Ser Val Ser Glu Pro Leu Ala Thr Leu Val Leu Ser His Gly
        435                 440                 445

Gly His Ile Leu Ala Ser Thr Ser Gly Asp Ser Asp His Ser Pro Arg
    450                 455                 460

Phe Ser Gly Thr Ser Gly Pro Asn Ser Leu Arg Leu Glu Ile Arg Asp
465                 470                 475                 480

Leu Glu Glu Thr Asp Ser Gly Glu Tyr Lys Cys Ser Ala Thr Asn Ser
                485                 490                 495

Leu Gly Asn Ala Thr Ser Thr Leu Asp Phe His Ala Asn Ala Ala Arg
            500                 505                 510

Leu Leu Ile Ser Pro Ala Ala Glu Val Val Glu Gly Gln Ala Val Thr
            515                 520                 525

Leu Ser Cys Arg Ser Gly Leu Ser Pro Thr Pro Asp Ala Arg Phe Ser
        530                 535                 540

Trp Tyr Leu Asn Gly Ala Leu Leu His Glu Gly Pro Gly Ser Ser Leu
545                 550                 555                 560

Leu Leu Pro Ala Ala Ser Ser Thr Asp Ala Gly Ser Tyr His Cys Arg
                565                 570                 575

Ala Arg Asp Gly His Ser Ala Ser Gly Pro Ser Ser Pro Ala Val Leu
            580                 585                 590

Thr Val Leu Tyr Pro Pro Arg Gln Pro Thr Phe Thr Thr Arg Leu Asp
        595                 600                 605

Leu Asp Ala Ala Gly Ala Gly Ala Arg Arg Gly Leu Leu Leu Cys
            610                 615                 620

Arg Val Asp Ser Asp Pro Pro Ala Arg Leu Gln Leu Leu His Lys Asp
625                 630                 635                 640

Arg Val Val Ala Thr Ser Leu Pro Ser Gly Gly Gly Cys Ser Thr Cys
                645                 650                 655

Gly Gly Cys Ser Pro Arg Met Lys Val Thr Lys Ala Pro Asn Leu Leu
            660                 665                 670

Arg Val Glu Ile His Asn Pro Leu Leu Glu Glu Gly Leu Tyr Leu
        675                 680                 685

Cys Glu Ala Ser Asn Ala Leu Gly Asn Ala Ser Thr Ser Ala Thr Phe
    690                 695                 700

Asn Gly Gln Ala Thr Val Leu Ala Ile Ala Pro Ser His Thr Leu Gln
705                 710                 715                 720

Glu Gly Thr Glu Ala Asn Leu Thr Cys Asn Val Ser Arg Glu Ala Ala
                725                 730                 735

Gly Ser Pro Ala Asn Phe Ser Trp Phe Arg Asn Gly Val Leu Trp Ala
            740                 745                 750

Gln Gly Pro Leu Glu Thr Val Thr Leu Leu Pro Val Ala Arg Thr Asp
        755                 760                 765

Ala Ala Leu Tyr Ala Cys Arg Ile Leu Thr Glu Ala Gly Ala Gln Leu
    770                 775                 780

Ser Thr Pro Val Leu Leu Ser Val Leu Tyr Pro Pro Asp Arg Pro Lys
785                 790                 795                 800

Leu Ser Ala Leu Leu Asp Met Gly Gln Gly His Met Ala Leu Phe Ile
                805                 810                 815

Cys Thr Val Asp Ser Arg Pro Leu Ala Leu Leu Ala Leu Phe His Gly
            820                 825                 830

Glu His Leu Leu Ala Thr Ser Leu Gly Pro Gln Val Pro Ser His Gly
        835                 840                 845

Arg Phe Gln Ala Lys Ala Glu Ala Asn Ser Leu Lys Leu Glu Val Arg
```

-continued

```
            850                 855                 860
Glu Leu Gly Leu Gly Asp Ser Gly Ser Tyr Arg Cys Glu Ala Thr Asn
865                 870                 875                 880

Val Leu Gly Ser Ser Asn Thr Ser Leu Phe Phe Gln Val Arg Gly Ala
                    885                 890                 895

Trp Val Gln Val Ser Pro Ser Pro Glu Leu Gln Glu Gly Gln Ala Val
                900                 905                 910

Val Leu Ser Cys Gln Val Pro Thr Gly Val Pro Glu Gly Thr Ser Tyr
            915                 920                 925

Arg Trp Tyr Arg Asp Gly Gln Pro Leu Gln Glu Ser Thr Ser Ala Thr
        930                 935                 940

Leu Arg Phe Ala Ala Ile Thr Leu Thr Gln Ala Gly Ala Tyr His Cys
945                 950                 955                 960

Gln Ala Gln Ala Pro Gly Ser Ala Thr Thr Ser Leu Ala Val Pro Ile
                    965                 970                 975

Ser Leu His Val Ser Tyr Ala Pro Arg His Val Thr Leu Thr Thr Leu
                980                 985                 990

Met Asp Thr Gly Pro Gly Arg Leu  Gly Leu Leu Leu Cys  Arg Val Asp
            995                 1000                1005

Ser Asp  Pro Pro Ala Gln Leu  Arg Leu Leu His Gly  Asp Arg Leu
    1010                 1015                1020

Val Ala  Ser Thr Leu Gln Gly  Val Gly Gly Pro Glu  Gly Ser Ser
    1025                 1030                1035

Pro Arg  Leu His Val Ala Val  Ala Pro Asn Thr Leu  Arg Leu Glu
    1040                 1045                1050

Ile His  Gly Ala Met Leu Glu  Asp Glu Gly Val Tyr  Ile Cys Glu
    1055                 1060                1065

Ala Ser  Asn Thr Leu Gly Gln  Ala Ser Ala Ser Ala  Asp Phe Asp
    1070                 1075                1080

Ala Gln  Ala Val Asn Val Gln  Val Trp Pro Gly Ala  Thr Val Arg
    1085                 1090                1095

Glu Gly  Gln Leu Val Asn Leu  Thr Cys Leu Val Trp  Thr Thr His
    1100                 1105                1110

Pro Ala  Gln Leu Thr Tyr Thr  Trp Tyr Gln Asp Gly  Gln Gln Arg
    1115                 1120                1125

Leu Asp  Ala His Ser Ile Pro  Leu Pro Asn Val Thr  Val Arg Asp
    1130                 1135                1140

Ala Thr  Ser Tyr Arg Cys Gly  Val Gly Pro Pro Gly  Arg Ala Pro
    1145                 1150                1155

Arg Leu  Ser Arg Pro Ile Thr  Leu Asp Val Leu Tyr  Ala Pro Arg
    1160                 1165                1170

Asn Leu  Arg Leu Thr Tyr Leu  Leu Glu Ser His Gly  Gly Gln Leu
    1175                 1180                1185

Ala Leu  Val Leu Cys Thr Val  Asp Ser Arg Pro Pro  Ala Gln Leu
    1190                 1195                1200

Ala Leu  Ser His Ala Gly Arg  Leu Leu Ala Ser Ser  Thr Ala Ala
    1205                 1210                1215

Ser Val  Pro Asn Thr Leu Arg  Leu Glu Leu Arg Gly  Pro Gln Pro
    1220                 1225                1230

Arg Asp  Glu Gly Phe Tyr Ser  Cys Ser Ala Arg Ser  Pro Leu Gly
    1235                 1240                1245

Gln Ala  Asn Thr Ser Leu Glu  Leu Arg Leu Glu Gly  Val Arg Val
    1250                 1255                1260
```

```
Ile Leu Ala Pro Glu Ala Ala Val Pro Glu Gly Ala Pro Ile Thr
    1265                1270                1275

Val Thr Cys Ala Asp Pro Ala Ala His Ala Pro Thr Leu Tyr Thr
    1280                1285                1290

Trp Tyr His Asn Gly Arg Trp Leu Gln Glu Gly Pro Ala Ala Ser
    1295                1300                1305

Leu Ser Phe Leu Val Ala Thr Arg Ala His Ala Gly Ala Tyr Ser
    1310                1315                1320

Cys Gln Ala Gln Asp Ala Gln Gly Thr Arg Ser Ser Arg Pro Ala
    1325                1330                1335

Ala Leu Gln Val Leu Tyr Ala Pro Gln Asp Ala Val Leu Ser Ser
    1340                1345                1350

Phe Arg Asp Ser Arg Ala Arg Ser Met Ala Val Ile Gln Cys Thr
    1355                1360                1365

Val Asp Ser Glu Pro Pro Ala Glu Leu Ala Leu Ser His Asp Gly
    1370                1375                1380

Lys Val Leu Ala Thr Ser Ser Gly Val His Ser Leu Ala Ser Gly
    1385                1390                1395

Thr Gly His Val Gln Val Ala Arg Asn Ala Leu Arg Leu Gln Val
    1400                1405                1410

Gln Asp Val Pro Ala Gly Asp Asp Thr Tyr Val Cys Thr Ala Gln
    1415                1420                1425

Asn Leu Leu Gly Ser Ile Ser Thr Ile Gly Arg Leu Gln Val Glu
    1430                1435                1440

Gly Ala Arg Val Val Ala Glu Pro Gly Leu Asp Val Pro Glu Gly
    1445                1450                1455

Ala Ala Leu Asn Leu Ser Cys Arg Leu Leu Gly Gly Pro Gly Pro
    1460                1465                1470

Val Gly Asn Ser Thr Phe Ala Trp Phe Trp Asn Asp Arg Arg Leu
    1475                1480                1485

His Ala Glu Pro Val Pro Thr Leu Ala Phe Thr His Val Ala Arg
    1490                1495                1500

Ala Gln Ala Gly Met Tyr His Cys Leu Ala Glu Leu Pro Thr Gly
    1505                1510                1515

Ala Ala Ala Ser Ala Pro Val Met Leu Arg Val Leu Tyr Pro Pro
    1520                1525                1530

Lys Thr Pro Thr Met Met Val Phe Val Glu Pro Glu Gly Gly Leu
    1535                1540                1545

Arg Gly Ile Leu Asp Cys Arg Val Asp Ser Glu Pro Leu Ala Ser
    1550                1555                1560

Leu Thr Leu His Leu Gly Ser Arg Leu Val Ala Ser Ser Gln Pro
    1565                1570                1575

Gln Gly Ala Pro Ala Glu Pro His Ile His Val Leu Ala Ser Pro
    1580                1585                1590

Asn Ala Leu Arg Val Asp Ile Glu Ala Leu Arg Pro Ser Asp Gln
    1595                1600                1605

Gly Glu Tyr Ile Cys Ser Ala Ser Asn Val Leu Gly Ser Ala Ser
    1610                1615                1620

Thr Ser Thr Tyr Phe Gly Val Arg Ala Leu His Arg Leu His Gln
    1625                1630                1635

Phe Gln Gln Leu Leu Trp Val Leu Gly Leu Leu Val Gly Leu Leu
    1640                1645                1650
```

-continued

```
Leu Leu  Leu Leu Gly Leu Gly  Ala Cys Tyr Thr Trp  Ser Ser Leu
    1655              1660                 1665

Ile Leu  Met Gln Pro His Val  Arg Pro Gln Pro Val  Pro His Pro
    1670              1675                 1680

Trp Ala  Glu Val Ile
    1685

<210> SEQ ID NO 21
<211> LENGTH: 372
<212> TYPE: PRT
<213> ORGANISM: Homo sapiens

<400> SEQUENCE: 21

Met Ser Lys Ala Phe Gly Leu Leu Arg Gln Ile Cys Gln Ser Ile Leu
1               5                   10                  15

Ala Glu Ser Ser Gln Ser Pro Ala Asp Leu Glu Lys Lys Glu Glu
            20                  25                  30

Asp Ser Asn Met Lys Arg Glu Gln Pro Arg Glu Arg Pro Arg Ala Trp
        35                  40                  45

Asp Tyr Pro His Gly Leu Val Gly Leu His Asn Ile Gly Gln Thr Cys
    50                  55                  60

Cys Leu Asn Ser Leu Ile Gln Val Phe Val Met Asn Val Asp Phe Thr
65                  70                  75                  80

Arg Ile Leu Lys Arg Ile Thr Val Pro Arg Gly Ala Asp Glu Gln Arg
                85                  90                  95

Arg Ser Val Pro Phe Gln Met Leu Leu Leu Leu Glu Lys Met Gln Asp
            100                 105                 110

Ser Arg Gln Lys Ala Val Arg Pro Leu Glu Leu Ala Tyr Cys Leu Gln
        115                 120                 125

Lys Cys Asn Val Pro Leu Phe Val Gln His Asp Ala Ala Gln Leu Tyr
    130                 135                 140

Leu Lys Leu Trp Asn Leu Ile Lys Asp Gln Ile Thr Asp Val His Leu
145                 150                 155                 160

Val Glu Arg Leu Gln Ala Leu Tyr Met Ile Arg Val Lys Asp Ser Leu
                165                 170                 175

Ile Cys Val Asp Cys Ala Met Glu Ser Ser Arg Asn Ser Ser Met Leu
            180                 185                 190

Thr Leu Pro Leu Ser Leu Phe Asp Val Asp Ser Lys Pro Leu Lys Thr
        195                 200                 205

Leu Glu Asp Ala Leu His Cys Phe Phe Gln Pro Arg Glu Leu Ser Ser
    210                 215                 220

Lys Ser Lys Cys Phe Cys Glu Asn Cys Gly Lys Lys Thr Arg Gly Lys
225                 230                 235                 240

Gln Val Leu Lys Leu Thr His Leu Pro Gln Thr Leu Thr Ile His Leu
                245                 250                 255

Met Arg Phe Ser Ile Arg Asn Ser Gln Thr Arg Lys Ile Cys His Ser
            260                 265                 270

Leu Tyr Phe Pro Gln Ser Leu Asp Phe Ser Gln Ile Leu Pro Met Lys
        275                 280                 285

Arg Glu Ser Cys Asp Ala Glu Glu Gln Ser Gly Gly Gln Tyr Glu Leu
    290                 295                 300

Phe Ala Val Ile Ala His Val Gly Met Ala Asp Ser Gly His Tyr Cys
305                 310                 315                 320

Val Tyr Ile Arg Asn Ala Val Asp Gly Lys Trp Phe Cys Phe Asn Asp
                325                 330                 335
```

```
Ser Asn Ile Cys Leu Val Ser Trp Glu Asp Ile Gln Cys Thr Tyr Gly
                340                 345                 350

Asn Pro Asn Tyr His Trp Gln Glu Thr Ala Tyr Leu Leu Val Tyr Met
                355                 360                 365

Lys Met Glu Cys
        370

<210> SEQ ID NO 22
<211> LENGTH: 246
<212> TYPE: PRT
<213> ORGANISM: Homo sapiens

<400> SEQUENCE: 22

Met Val Val Asp Phe Trp Thr Trp Glu Gln Thr Phe Gln Glu Leu Ile
1               5                   10                  15

Gln Glu Ala Lys Pro Arg Ala Thr Trp Thr Leu Lys Leu Asp Gly Asn
                20                  25                  30

Leu Gln Leu Asp Cys Leu Ala Gln Gly Trp Lys Gln Tyr Gln Gln Arg
            35                  40                  45

Ala Phe Gly Trp Phe Arg Cys Ser Ser Cys Gln Arg Ser Trp Ala Ser
50                  55                  60

Ala Gln Val Gln Ile Leu Cys His Thr Tyr Trp Glu His Trp Thr Ser
65                  70                  75                  80

Gln Gly Gln Val Arg Met Arg Leu Phe Gly Arg Cys Gln Lys Cys
                85                  90                  95

Ser Trp Ser Gln Tyr Glu Met Pro Glu Phe Ser Ser Asp Ser Thr Met
                100                 105                 110

Arg Ile Leu Ser Asn Leu Val Gln His Ile Leu Lys Lys Tyr Tyr Gly
            115                 120                 125

Asn Gly Thr Arg Lys Ser Pro Glu Met Pro Val Ile Leu Glu Val Ser
130                 135                 140

Leu Glu Gly Ser His Asp Thr Ala Asn Cys Glu Ala Cys Thr Leu Gly
145                 150                 155                 160

Ile Cys Gly Gln Gly Leu Lys Ser Cys Met Thr Lys Pro Ser Lys Ser
                165                 170                 175

Leu Leu Pro His Leu Lys Thr Gly Asn Ser Ser Pro Gly Ile Gly Ala
            180                 185                 190

Val Tyr Leu Ala Asn Gln Ala Lys Asn Gln Ser Ala Glu Ala Lys Glu
        195                 200                 205

Ala Lys Gly Ser Gly Tyr Glu Lys Leu Gly Pro Ser Arg Asp Pro Asp
    210                 215                 220

Pro Leu Asn Ile Cys Val Phe Ile Leu Leu Val Phe Ile Val Val
225                 230                 235                 240

Lys Cys Phe Thr Ser Glu
                245

<210> SEQ ID NO 23
<211> LENGTH: 558
<212> TYPE: PRT
<213> ORGANISM: Homo sapiens

<400> SEQUENCE: 23

Met Ala Glu Leu Asn Thr His Val Asn Val Lys Glu Lys Ile Tyr Ala
1               5                   10                  15

Val Arg Ser Val Val Pro Asn Lys Ser Asn Asn Glu Ile Val Leu Val
                20                  25                  30
```

```
Leu Gln Gln Phe Asp Phe Asn Val Asp Lys Ala Val Gln Ala Phe Val
            35                  40                  45

Asp Gly Ser Ala Ile Gln Val Leu Lys Glu Trp Asn Met Thr Gly Lys
 50                  55                  60

Lys Lys Asn Asn Lys Arg Lys Ser Lys Ser Lys Gln His Gln Gly
 65                  70                  75                  80

Asn Lys Asp Ala Lys Asp Lys Val Glu Arg Pro Glu Ala Gly Pro Leu
                    85                  90                  95

Gln Pro Gln Pro Pro Gln Ile Gln Asn Gly Pro Met Asn Gly Cys Glu
                    100                 105                 110

Lys Asp Ser Ser Ser Thr Asp Ser Ala Asn Glu Lys Pro Ala Leu Ile
                    115                 120                 125

Pro Arg Glu Lys Lys Ile Ser Ile Leu Glu Glu Pro Ser Lys Ala Leu
            130                 135                 140

Arg Gly Val Thr Glu Gly Asn Arg Leu Leu Gln Gln Lys Leu Ser Leu
145                 150                 155                 160

Asp Gly Asn Pro Lys Pro Ile His Gly Thr Thr Glu Arg Ser Asp Gly
                    165                 170                 175

Leu Gln Trp Ser Ala Glu Gln Pro Cys Asn Pro Ser Lys Pro Lys Ala
            180                 185                 190

Lys Thr Ser Pro Val Lys Ser Asn Thr Pro Ala Ala His Leu Glu Ile
            195                 200                 205

Lys Pro Asp Glu Leu Ala Lys Lys Arg Gly Pro Asn Ile Glu Lys Ser
    210                 215                 220

Val Lys Asp Leu Gln Arg Cys Thr Val Ser Leu Thr Arg Tyr Arg Val
225                 230                 235                 240

Met Ile Lys Glu Glu Val Asp Ser Ser Val Lys Lys Ile Lys Ala Ala
                    245                 250                 255

Phe Ala Glu Leu His Asn Cys Ile Ile Asp Lys Glu Val Ser Leu Met
            260                 265                 270

Ala Glu Met Asp Lys Val Lys Glu Glu Ala Met Glu Ile Leu Thr Ala
            275                 280                 285

Arg Gln Lys Lys Ala Glu Glu Leu Lys Arg Leu Thr Asp Leu Ala Ser
    290                 295                 300

Gln Met Ala Glu Met Gln Leu Ala Glu Leu Arg Ala Glu Ile Lys His
305                 310                 315                 320

Phe Val Ser Glu Arg Lys Tyr Asp Glu Glu Leu Gly Lys Ala Ala Arg
                    325                 330                 335

Phe Ser Cys Asp Ile Glu Gln Leu Lys Ala Gln Ile Met Leu Cys Gly
            340                 345                 350

Glu Ile Thr His Pro Lys Asn Asn Tyr Ser Ser Arg Thr Pro Cys Ser
            355                 360                 365

Ser Leu Leu Pro Leu Leu Asn Ala His Ala Ala Thr Ser Gly Lys Gln
    370                 375                 380

Ser Asn Phe Ser Arg Lys Ser Ser Thr His Asn Lys Pro Ser Glu Gly
385                 390                 395                 400

Lys Ala Ala Asn Pro Lys Met Val Ser Ser Leu Pro Ser Thr Ala Asp
                    405                 410                 415

Pro Ser His Gln Thr Met Pro Ala Asn Lys Gln Asn Gly Ser Ser Asn
            420                 425                 430

Gln Arg Arg Arg Phe Asn Pro Gln Tyr His Asn Asn Arg Leu Asn Gly
    435                 440                 445
```

-continued

```
Pro Ala Lys Ser Gln Gly Ser Gly Asn Glu Ala Glu Pro Leu Gly Lys
    450                 455                 460
Gly Asn Ser Arg His Glu His Arg Arg Gln Pro His Asn Gly Phe Arg
465                 470                 475                 480
Pro Lys Asn Lys Gly Gly Ala Lys Asn Gln Glu Ala Ser Leu Gly Met
            485                 490                 495
Lys Thr Pro Glu Ala Pro Ala His Ser Glu Lys Pro Arg Arg Arg Gln
            500                 505                 510
His Ala Ala Asp Thr Ser Glu Ala Arg Pro Phe Arg Gly Ser Val Gly
        515                 520                 525
Arg Val Ser Gln Cys Asn Leu Cys Pro Thr Arg Ile Glu Val Ser Thr
530                 535                 540
Asp Ala Ala Val Leu Ser Val Pro Ala Val Thr Leu Val Ala
545                 550                 555
```